(12) United States Patent
Look et al.

(10) Patent No.: US 10,357,559 B2
(45) Date of Patent: Jul. 23, 2019

(54) TEMPERATURE STABLE VACCINE FORMULATIONS

(71) Applicant: EMERGENT PRODUCT DEVELOPMENT GAITHERSBURG INC., Gaithersburg, MD (US)

(72) Inventors: Jee Look, Boyds, MD (US); Christian Fernando Ruiz, Germantown, MD (US); Aaron Paul Miles, Potomac, MD (US); Richard William Welch, Gaithersburg, MD (US)

(73) Assignee: Emergent Product Development Gaithersburg Inc., Gaithersburg, MD (US)

( * ) Notice: Subject to any disclaimer, the term of this patent is extended or adjusted under 35 U.S.C. 154(b) by 0 days.

(21) Appl. No.: 15/108,244

(22) PCT Filed: Dec. 23, 2014

(86) PCT No.: PCT/US2014/072193
§ 371 (c)(1),
(2) Date: Jun. 24, 2016

(87) PCT Pub. No.: WO2015/100344
PCT Pub. Date: Jul. 2, 2015

(65) Prior Publication Data
US 2016/0324957 A1 Nov. 10, 2016

Related U.S. Application Data

(60) Provisional application No. 61/921,281, filed on Dec. 27, 2013.

(51) Int. Cl.
| | |
|---|---|
| A61K 39/39 | (2006.01) |
| A61K 47/26 | (2006.01) |
| A61K 9/19 | (2006.01) |
| A61K 39/07 | (2006.01) |
| A61K 39/12 | (2006.01) |
| A61K 39/145 | (2006.01) |
| C12N 7/00 | (2006.01) |
| A61K 39/00 | (2006.01) |

(52) U.S. Cl.
CPC ............... *A61K 39/39* (2013.01); *A61K 9/19* (2013.01); *A61K 39/07* (2013.01); *A61K 39/12* (2013.01); *A61K 39/145* (2013.01); *A61K 47/26* (2013.01); *C12N 7/00* (2013.01); *A61K 2039/55505* (2013.01); *A61K 2039/55511* (2013.01); *C12N 2760/16034* (2013.01)

(58) Field of Classification Search
None
See application file for complete search history.

(56) References Cited

U.S. PATENT DOCUMENTS

| | | | | |
|---|---|---|---|---|
| 4,710,378 | A | * | 12/1987 | Ohtomo .............. C07K 14/005 424/227.1 |
| 6,284,282 | B1 | | 9/2001 | Maa et al. |
| 6,316,006 | B1 | | 11/2001 | Worsham et al. |
| 6,387,665 | B1 | | 5/2002 | Ivins et al. |
| 6,890,512 | B2 | | 5/2005 | Roser et al. |
| 7,201,912 | B2 | | 4/2007 | Park et al. |
| 7,223,741 | B2 | | 5/2007 | Krieg |
| 7,261,900 | B2 | | 8/2007 | Leppla et al. |
| 7,438,909 | B2 | | 10/2008 | Morrow et al. |
| 7,442,373 | B2 | | 10/2008 | Morrow et al. |
| 8,778,359 | B2 | | 7/2014 | Kaisheva |
| 2003/0162167 | A1 | | 8/2003 | Houghton et al. |
| 2004/0028695 | A1 | * | 2/2004 | Park ...................... C07K 14/32 424/190.1 |
| 2005/0276756 | A1 | | 12/2005 | Hoo et al. |
| 2005/0281830 | A1 | | 12/2005 | Morrow et al. |
| 2006/0246079 | A1 | | 11/2006 | Morrow et al. |
| 2006/0257426 | A1 | | 11/2006 | Baker et al. |
| 2007/0009520 | A1 | | 1/2007 | Yamaguchi et al. |
| 2008/0226729 | A1 | | 9/2008 | Sullivan et al. |
| 2009/0202553 | A1 | | 8/2009 | Morrow et al. |
| 2009/0232894 | A1 | * | 9/2009 | Chouvenc ............ A61K 9/1623 424/489 |
| 2010/0158951 | A1 | * | 6/2010 | Randolph ............... A61K 39/08 424/239.1 |
| 2010/0183675 | A1 | * | 7/2010 | Watkinson ............. A61K 39/07 424/246.1 |

(Continued)

FOREIGN PATENT DOCUMENTS

CN 1887275 A 1/2007
WO WO 2007/124090 A2 11/2007

(Continued)

OTHER PUBLICATIONS

Wolff et al. 2008 (Protection of aluminum hydroxide during lyophilization as an adjuvant for freeze-dried vaccines; Colloids and Surfaces A: Physiochem. Eng. Aspects 330: 116-126).*

(Continued)

*Primary Examiner* — Mary Maille Lyons

(74) *Attorney, Agent, or Firm* — Sterne, Kessler, Goldstein & Fox P.L.L.C.

(57) ABSTRACT

Vaccine antigen formulations that are stable after undergoing freeze and thaw conditions and methods of preparing the formulations are provided. Methods of using the formulations to prepare vaccine are also provided. Vaccines comprising the formulations are useful, for example, to protect against, inhibit or alleviate a disease or infection, such as related to anthrax infection.

15 Claims, 22 Drawing Sheets

Specification includes a Sequence Listing.

(56) References Cited

U.S. PATENT DOCUMENTS

| | | | |
|---|---|---|---|
| 2011/0212127 | A1 | 9/2011 | Drew et al. |
| 2011/0229507 | A1 | 9/2011 | Kaisheva |
| 2015/0023998 | A1 | 1/2015 | Kaisheva |
| 2015/0335752 | A1 | 11/2015 | Look et al. |

FOREIGN PATENT DOCUMENTS

| | | | |
|---|---|---|---|
| WO | WO 2008/079464 | A2 | 7/2008 |
| WO | WO-2010053610 | A2 | 5/2010 |
| WO | WO-2010084298 | A1 | 7/2010 |
| WO | WO-2012177970 | A1 | 12/2012 |
| WO | WO-2014004578 | A1 | 1/2014 |

OTHER PUBLICATIONS

Arias, M.A., et al., "Glucopyranosyl Lipid Adjuvant (GLA), a Synthetic TLR4 Agonist, Promotes Potent Systemic and Mucosal Responses to Intranasal Immunization with HIVgp140," PLoS One 7(7):e41144, Public Library of Science, United States (2012).

Bradley, K.A., et al., "Identification of the Cellular Receptor for Anthrax Toxin," Nature 414(6860):225-229, Nature Publishing Group, England (2001).

Chen, D., et al., "Thermostable Formulations of a Hepatitis B Vaccine and a Meningitis A Polysaccharide Conjugate Vaccine Produced by a Spray Drying Method," Vaccine 28(31):5093-5099, Elsevier Science, Netherlands (2010).

Diminsky, D., et al., "Physical, Chemical and Immunological Stability of Cho-Derived Hepatitis B Surface Antigen (HBsAg) Particles," Vaccine 18(1-2):3-17, Elsevier Science, Netherlands (1999).

D'Souza, A.J., et al., "Rapid Deamidation of Recombinant Protective Antigen When Adsorbed on Aluminum Hydroxide Gel Correlates with Reduced Potency of Vaccine," Journal of Pharmaceutical Sciences 102(2):454-461, Wiley, United States (2013).

GenBank, "Protective Antigen [Bacillus anthracis str. A0174]," Accession No. ZP_02937261.1, accessed at http://www.ncbi.nlm.nih.gov/protein/ZP_02937261.1?report=genpept, accessed on Jul. 9, 2015, 2 pages.

GenBank, "Protective Antigen [Bacillus anthracis str. A0389]," Accession No. ZP_02900013.1, accessed at http://www.ncbi.nlm.nih.gov/protein/ZP_02900013.1?report=genpept, accessed on Jul. 9, 2015, 2 pages.

GenBank, "Protective Antigen [Bacillus anthracis str. A0465]," Accession No. ZP_02880951.1, accessed at http://www.ncbi.nlm.nih.gov/protein/ZP_02880951.1?report=genpept.

GenBank, "Protective Antigen [Bacillus anthracis str. A2012]," Accession No. NP_652920.1, accessed at http://www.ncbi.nlm.nih.gov/protein/NP_652920.1?report=genpept, accessed on Jul. 10, 2015, 2 pages.

Hering, D., et al., "Validation of the Anthrax Lethal Toxin Neutralization Assay," Biologicals 32(1):17-27, Academic Press, England (2004).

International Search Report for Application No. PCT/US2013/047712, ISA/US, Alexandria, Virginia, United States, dated Nov. 26, 2013, 4 pages.

International Search Report for International Application No. PCT/US2014/072193, ISA/US, Alexandria, Virginia, United States, dated Apr. 2, 2015, 4 pages.

Leffel, E.K., et al., "Recombinant Protective Antigen Anthrax Vaccine Improves Survival when Administered as a Postexposure Prophylaxis Countermeasure with Antibiotic in the New Zealand White Rabbit Model of Inhalation Anthrax," Clinical and Vaccine Immunology 19(8):1158-1164, American Society for Microbiology, United States (2012).

Li, H., et al., "Standardized, Mathematical Model-Based and Validated in Vitro Analysis of Anthrax Lethal Toxin Neutralization," Journal of Immunological Methods 333(1-2):89-106, Elsevier, Netherlands (2008).

Maa, Y.F., et al., "Stabilization of Alum-Adjuvanted Vaccine Dry Powder Formulations: Mechanism and Application," Journal of Pharmaceutical Sciences 92(2):319-332, Wiley, United States (2003).

McKevitt, M.T., et al., "Effects of Endogenous D-Alanine Synthesis and Autoinhibition of Bacillus Anthracis Germination on In Vitro and In Vivo Infections," Infection and Immunity 75(12):5726-5734, American Society for Microbiology, United States (2007).

Nelson, C.M., et al., "Hepatitis B Vaccine Freezing in the Indonesian Cold Chain: Evidence and Solutions," Bulletin of the World Health Organization 82(2):99-105, World Health Organization, Switzerland (2004).

Omland, K.S., et al., "Interlaboratory Comparison of Results of an Anthrax Lethal Toxin Neutralization Assay for Assessment of Functional Antibodies in Multiple Species," Clinical and Vaccine Immunology 15(6):946-953, American Society for Microbiology, United States (2008).

Phipps, A.J., et al., "Rabbit and Nonhuman Primate Models of Toxin-Targeting Human Anthrax Vaccines," Microbiology and Molecular Biology Reviews 68(4):617-629, American Society for Microbiology, United States (2004).

Pittman, P.R., et al., "Patterns of Antibody Response in Humans to the Anthrax Vaccine Adsorbed (AVA) Primary (Six-Dose) Series," Vaccine 24(17):3654-3660, Elsevier Science,Netherlands (2006).

"Temperature Sensitivity of Vaccines," WHO publication WHO/IVB/06.10, Immunization, Vaccines and Biologicals, World Health Organization, Switzerland, Aug. 2006.

"The Effect of Freezing on the Appearance, Potency and Toxicity of Adsorbed and Unadsorbed DPT Vaccines," WHO Weekly Epidemiological Record 55:385-392, World Health Organization, Switzerland (1980).

Wang, S.H., et al., "Stable Dry Powder Formulation for Nasal Delivery of Anthrax Vaccine." Journal of Pharmaceutical Sciences 101(1):31-47, Wiley, United States (2012).

Wang, W. and Singh, M., "Selection of Adjuvants for Enhanced Vaccine Potency," World Journal of Vaccines 1:33-78, Scientific Research Publishers, China (2011).

Written Opinion for International Application No. PCT/US2014/072193, ISA/US, Alexandria, Virginia, United States, dated Apr. 2, 2015, 5 pages.

Wolff, L,. et al., "Protection of Aluminum hydroxide during lyophilisation as an adjuvant for freeze-dried vaccines," Colloids and surfaces A: Physiochemical and Engineering Aspects 330:116-126, Elsevier, Netherlands (2008).

Office Action dated Sep. 9, 2016, in U.S. Appl. No. 14/410,942, Look, Jee. et al., filed Dec. 23, 2014, 21 pages.

Office Action dated Sep. 4, 2015, in U.S. Appl. No. 14/323,811, Kaisheva, Elizabet, filed Jul. 3, 2014, 9 pages.

Office Action dated Jun. 7, 2016, in U.S. Appl. No. 14/323,811, Kaisheva, Elizabet, filed Jul. 3, 2014, 7 pages.

Ivins, B., et al., "Experimental anthrax vaccines: efficacy of adjuvants combined with protective antigen against an aerosol Bacillus anthracis spore challenge in guinea pigs," Vaccine 13(18):1779-1784, Elsevier, Great Britain (1995).

Singh, S., et al., "The osmoprotectants glycine and its methyl derivatives prevent the thermal inactivation of protective antigen of Bacillus anthracis," Biochemical and Biophysical Research Communications 216:559-564 (2004).

Vasconcelos, M.T.S.D., et al., "Electrochemical Evidence of Surfactant Activity of Hepes pH Buffer Which May Have Implications on Trace Metal Availability to Cultures in Vitro," Analytical Biochemistry 241: 248-253, Elsevier, Netherlands (1996).

* cited by examiner

Comparison of rPA102 vaccine before and after Freeze/Thaw rPA vaccine at 5 °C

After Freeze/thaw at -80 °C

Alum gel collapsed after freezing due to aggregation of alum particles

Regular Formulation
0.15mg/mL rPA, 1.5mg/mL Alum, 20mM Tris-HCl, pH 7.4

| Freeze/Thaw | Intact rPA102 | | Desorbed rPA102 | | |
|---|---|---|---|---|---|
| | Fluorescence (320/350) | In-vivo (MRPT)** | MLA | RP-HPLC (Purity) | SE-HPLC (%Monomer) |
| Before | 1.21 | 0.38 | 18% | 82.84 | 94.58 |
| After Freezing | 0.94* | 0.20*** | 2% | 74.95 | 79.8 |

* Indicating change in rPA102 protein structure after freezing, data from AD (AD12117 FD samples)
** Data from MRPT group
*** Statistical significant at 95% CI

- Freezing damages rPA102 vaccine
- Potency (MRPT) data correlates with physio-chemical and gel height (collapsed)

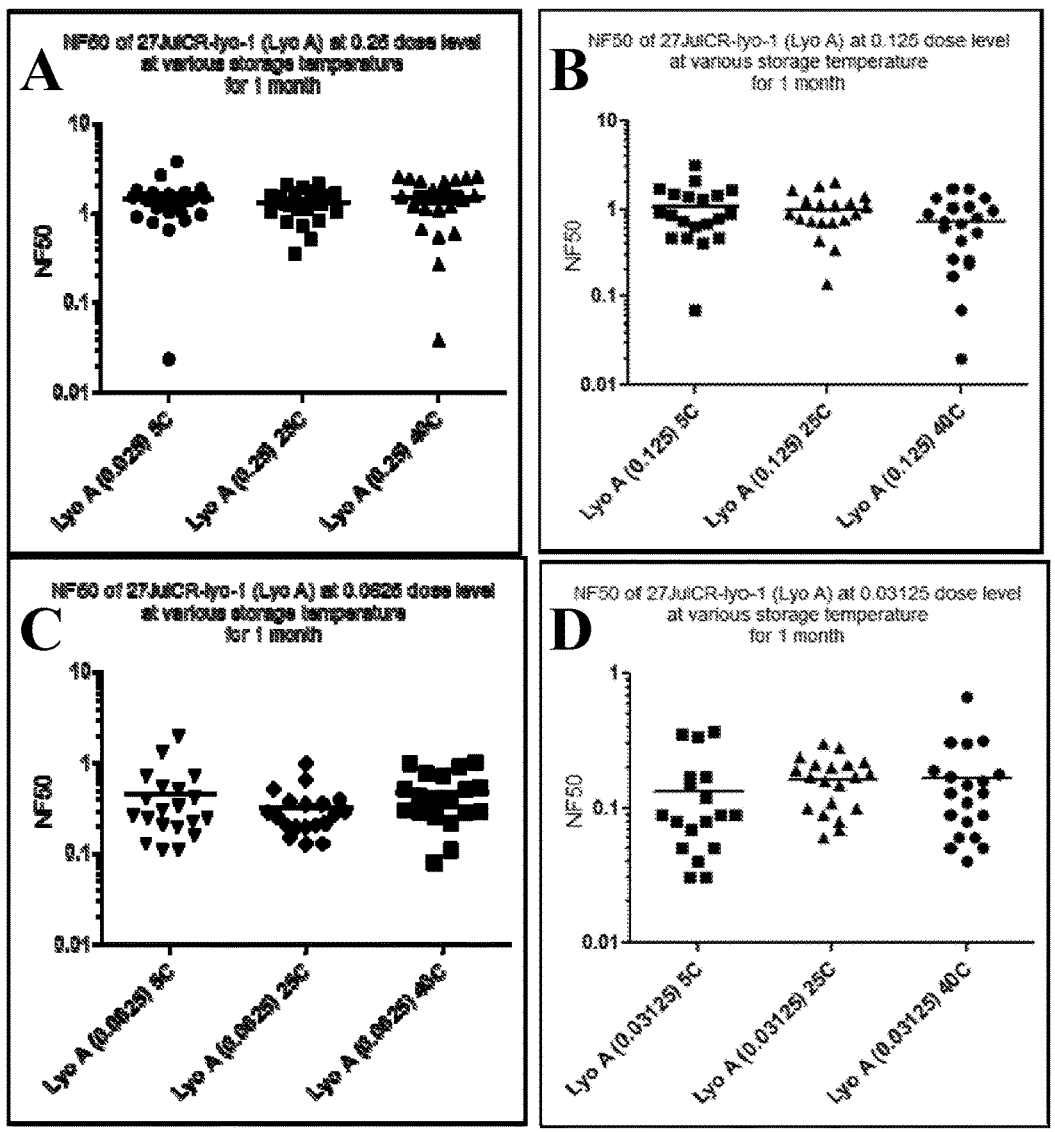
FIG. 17A-D

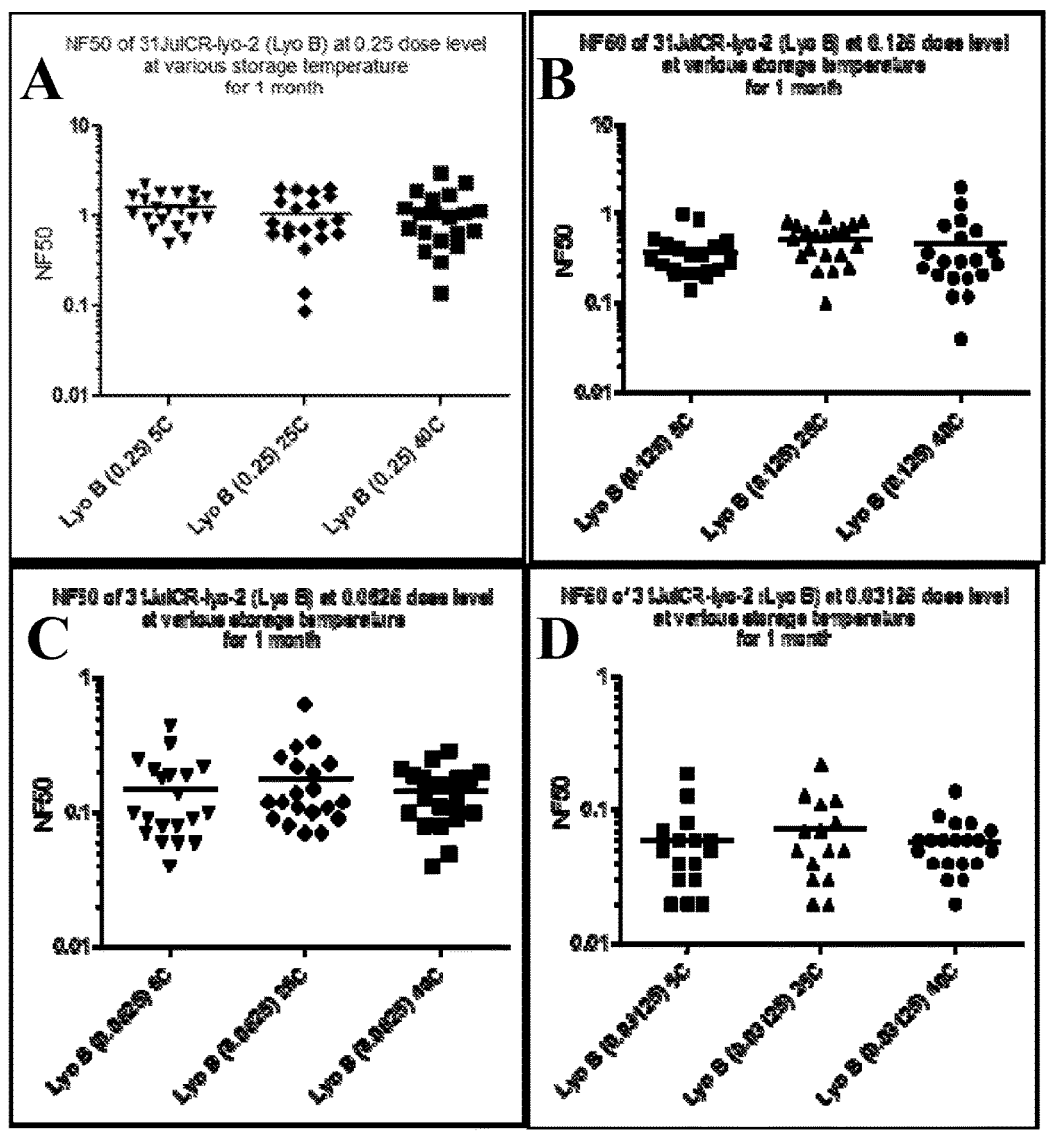
FIG. 18A-D

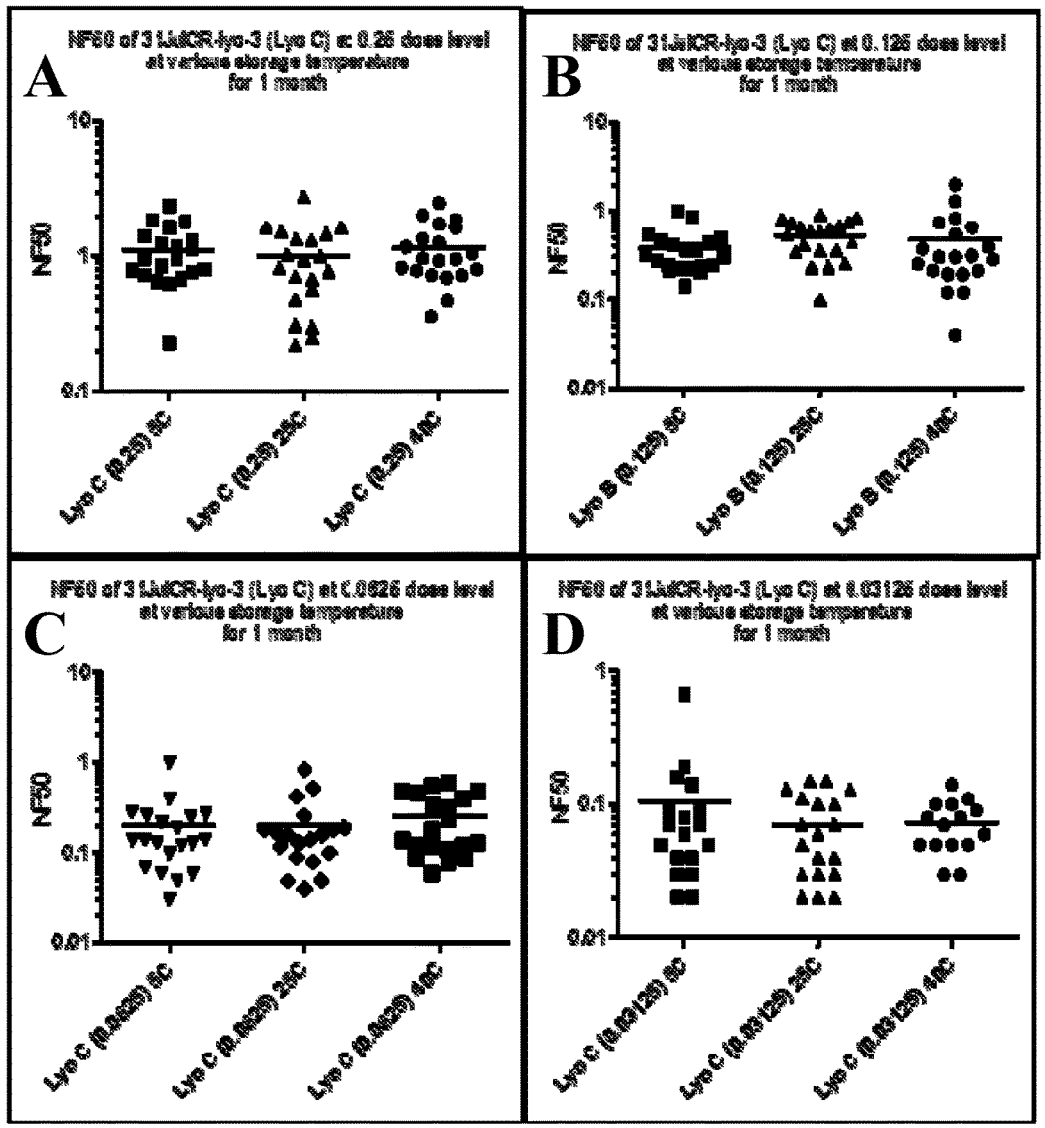
FIG. 19A-D

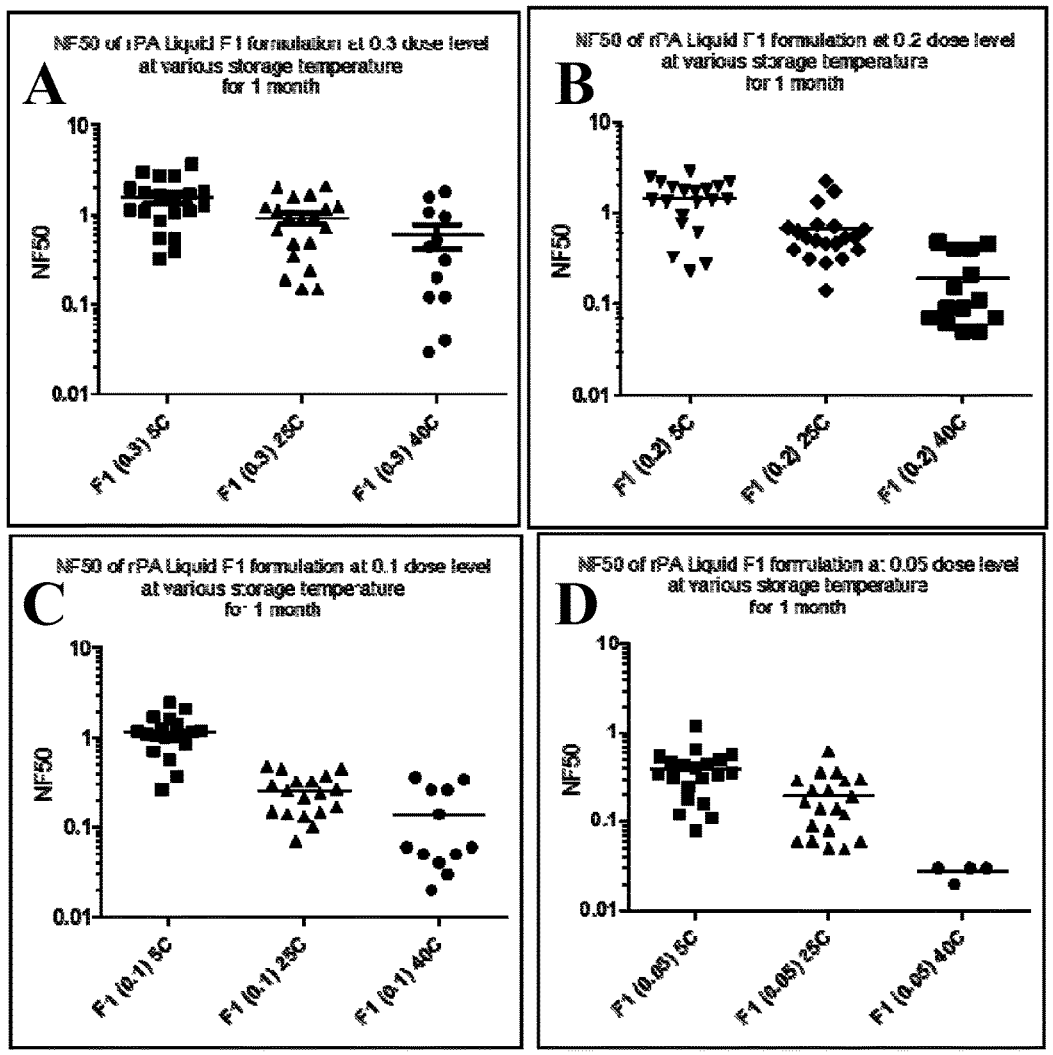
FIG. 20A-D

TEMPERATURE STABLE VACCINE FORMULATIONS

GOVERNMENT RIGHTS

This invention was made in part with government support under grant HHS0100201000059C. The government may have certain rights in this invention.

REFERENCE TO SEQUENCE LISTING SUBMITTED ELECTRONICALLY

The content of the electronically submitted sequence listing in ASCII text file (Name "2479_1250001_Sequence-Listing.txt"; Size: 13,068 bytes; and Date of Creation: Jun. 21, 2016) submitted via EFS-WEB is incorporated herein by reference in its entirety.

FIELD OF THE INVENTION

The present invention relates to temperature stable vaccine formulations containing an antigen adsorbed to an aluminum adjuvant and methods of preparing such formulations. The invention includes lyophilized and frozen vaccine formulations. The invention includes temperature stable vaccines, methods of making temperature stable vaccines and methods of use.

BACKGROUND OF THE INVENTION

Anthrax is a well-known infectious disease caused by a Gram-positive bacterium, Bacillus anthracis (B. anthracis). Among the three types of anthrax infection (cutaneous, gastrointestinal, and inhalation), cutaneous anthrax is the most common and is relatively easily treatable with various antibiotics. The other two types of anthrax infections are rare, but usually fatal even with aggressive anti-microbial therapy.

The major virulence factor, anthrax toxin, is composed of three proteins: protective antigen (PA, 83 kilo Dalton, kDa), edema factor (EF, 89 kDa), and lethal factor (LF, 90 kDa). The toxin components act in the binary combinations of PA+EF (edema toxin), and PA+LF (lethal toxin). PA is a cell receptor-binding protein and delivers the other two proteins (EF and LF) into the cytosol of infected cells.

The most effective known method for preventing anthrax is vaccination. The current and only FDA-approved anthrax vaccine in the United States (produced by Emergent Bio-Solutions Inc. under the trademark BIOTHRAX® (Anthrax Vaccine Adsorbed)) is produced from a sterile cell-free filtrate from an avirulent B. anthracis V770-NP1-R strain. The licensed anthrax vaccine is also called Anthrax Vaccine Adsorbed (or AVA). The vaccine primarily consists of PA, and aluminum hydroxide is used as an adjuvant. The vaccine was developed during the 1950s and 1960s and is licensed by the FDA to Emergent BioSolutions Inc. The vaccine shows less than 0.06% systemic reactions. The ability of the vaccine to elicit an immune response in humans is well-documented. The AVA vaccine is currently licensed for five doses over 18 months followed by annual boosts.

Although the AVA vaccine is effective and safe, new immunogenic compositions for preparing a vaccine that protects a subject against a lethal B. anthracis infection using recombinant technologies are under development. Because protective antigen (PA) is the common factor required for both the actions of LF and EF, it is often used to prepare vaccines for anthrax. Examples of PA vaccines in development include those disclosed in U.S. Pat. Nos. 6,316,006 and 6,387,665 and patent applications US 2010/0183675, US2011/0229507 and WO2010/053610.

Vaccines such as an AVA and PA typically contain at least one adjuvant to enhance a subject's immune response. Aluminum salt adjuvants, frequently referred to as alum, are currently the most widely used adjuvant for use in humans. Alum is usually aluminum hydroxide (also marketed as ALHYDROGEL® (aluminum hydroxide) or aluminum phosphate). AVA and the "next generation" Anthrax vaccines (such as recombinant PA) are formulated with aluminum hydroxide which binds the antigen.

Currently, vaccines containing alum require a cold chain. Cold chains have been established globally to keep vaccines at 2-8° C. during storage and distribution. Maintaining cold chains is expensive and difficult. In the event of a cold chain failure, vaccines can be exposed to higher or lower temperatures than intended. It is generally recommended that vaccines that contain alum be discarded if they undergo freeze/thaw processing during shipping and storage. Failure of a cold chain can occur in both industrialized and developing nations, and there are many reasons for cold chain failure, for instance, equipment failure, lack of resources or poor compliance. In many developing countries such as Indonesia, freezing temperatures were recorded in 75% of baseline shipments and freezing of freeze-sensitive is widespread. See *Hepatitis B vaccine freezing in the Indonesian cold chain: evidence and solutions. Bulletin of the World Health Organization* 2004; 82:99-105.

A vaccine that is dependent on a cold chain may also take longer to distribute to those in need in a timely manner. In the event of a bioterrorist event or other public health emergency, the ability to rapidly deliver vaccines and other medical countermeasures is critical. Eliminating dependence on the cold chain for distribution would lead to more prompt and efficient delivery of medical countermeasures in a variety of climates.

In order to avoid or minimalize cold chain requirements, many licensed vaccines are formulated as a dry powder composition that can be reconstituted immediately prior to administration. To date, all dry powder vaccines licensed for use in the US are produced through a lyophilization process. Lyophilization, also referred to as freeze drying, is a process that improves the long term stability of a vaccine. The process involves freezing the liquid vaccine formulation and subliming the frozen formulation under vacuum. Other technologies such as spray drying and foam drying have been developed with the aim of producing a stable, dry powder vaccine. These newer technologies produce dry powder vaccine material without the need for freezing and can be used with an alum containing vaccine. See, for instance, Chen et al., 2010, *Vaccine* 28:5093-5099. However, these newer technologies are still in their infancy and have yet to be used in the production of a licensed vaccine in the United States.

Freezing of vaccine compositions containing alum (either as part of the lyophilization process or to produce a frozen vaccine) generally induces aggregation of the aluminum particles and causes degradation of the antigen adsorbed onto the alum adjuvant resulting in potency loss. In addition, freezing causes reduction of the height of the settled aluminum gel (commonly referred to as gel collapse). See, for instance, "The effect of freezing on the appearance, potency and toxicity of adsorbed and unadsorbed DPT vaccines," 1980, *WHO Weekly Epidemiological Record* 55:385-92; "Temperature Sensitivity of Vaccines," August 2006, *WHO* publication WHO/IVB/06.10; Diminsky et al., 1999, *Vaccine* 18(1-2):3-17; Maa et al., 2003, *J Pharm Sci* 92(2):319-332.

Accordingly, there is a need to produce a vaccine that contains alum that can withstand freezing. Such a vaccine may be subjected to freezing as part of the manufacturing process (e.g., a lyophilized or frozen vaccine), shipping process or during storage. The present invention discloses novel formulations for the production of temperature stable vaccines containing alum.

SUMMARY OF THE INVENTION

The present invention provides vaccine formulations that contain alum and are capable of being frozen with little to no reduction of potency. In one embodiment, the frozen vaccine composition exhibits little to no alum gel collapse as a result of freezing.

In one embodiment, the vaccine or composition comprises at least 20% sugar which acts as a stabilizer. In one embodiment, the vaccine or composition comprises greater than 15%, greater than 20%, greater than 25%, or greater than 30% sugar. In some embodiments, the amount of sugar can be reduced without compromising potency if additional stabilizing agents such as amino acids and/or surfactants are added. For frozen and lyophilized vaccine formulations, potency can also be improved by increasing the freezing rate and by freezing suspended particles (as opposed to settled particles).

The invention includes frozen vaccine compositions, lyophilized vaccine compositions (which undergo freezing as part of the lyophilization process) and other vaccine formulations that are not susceptible to freeze/thaw conditions during shipping and storage.

Some embodiments of the invention include a composition for preparation of a lyophilized vaccine comprising at least one antigen adsorbed to an aluminum adjuvant and at least 20% (w/v) non-reducing sugar. Another embodiment includes a temperature stable liquid vaccine composition comprising at least one antigen adsorbed to an aluminum adjuvant and at least 20% (w/v) sugar. A further embodiment includes a composition comprising, prior to lyophilization, at least one antigen absorbed to an aluminum adjuvant and at least 20% (w/v) non-reducing sugar, wherein after reconstitution the non-reducing sugar is at least 6% (w/v). Compositions of the invention may further comprise a surfactant. In some embodiments composition of the invention comprises at least one antigen adsorbed to an aluminum adjuvant, a surfactant and at least 15% (w/v) sugar can be used for preparation of a lyophilized vaccine.

The invention also includes temperature stable liquid vaccine compositions comprising at least one antigen adsorbed to an aluminum adjuvant, a surfactant and at least 15% (w/v) sugar. In some embodiments, a composition further comprises at least one amino acid. Also included are stable liquid vaccine compositions comprising at least one antigen adsorbed to an aluminum adjuvant, a surfactant, an amino acid and at least 10% (w/v) sugar.

The invention further provides compositions for preparation of a lyophilized vaccine comprising at least one antigen adsorbed to an aluminum adjuvant, a surfactant, an amino acid and at least 10% (w/v) sugar.

The invention can be applied to numerous vaccines that contain an antigen adsorbed to an aluminum adjuvant. In one embodiment the vaccine is an anthrax vaccine such as rPA (recombinant PA) or Anthrax Vaccine Adsorbed.

The source of the protective antigen may vary. Thus, in some embodiments, a *B. anthracis* protective antigen protein is produced from an asporogenic *B. anthracis* bacterium. In some embodiments, an asporogenic *B. anthracis* bacterium is a ΔSterne-1(pPA102) CR4 strain of bacteria. In some embodiments, PA protein is expressed in other organisms such as *E. coli*.

In some embodiments, compositions of the invention may further comprise adjuvants (e.g., in addition to aluminum).

Some embodiments of the invention include methods of preparing a stable lyophilized vaccine, the method comprising (a) exchanging at least part of a liquid component of a first composition comprising at least one antigen adsorbed to an aluminum adjuvant with a second liquid component comprising a non-reducing sugar to create a second composition that comprises at least 20% (w/v) non-reducing sugar; and lyophilizing the second composition.

Some aspects of the invention include methods of preparing a stable lyophilized vaccine, the method comprising (a) exchanging at least part of a liquid component of a first composition comprising at least one antigen adsorbed to an aluminum adjuvant with a second liquid component comprising a non-reducing sugar and a surfactant to create a second composition that comprises at least 15% (w/v) non-reducing sugar; and (b) lyophilizing the second composition.

Some embodiments of the invention include methods of preparing a stable lyophilized vaccine, the method comprising (a) exchanging at least part of a liquid component of a first composition comprising at least one antigen adsorbed to an aluminum adjuvant with a second liquid component comprising a non-reducing sugar and a surfactant and an amino acid to create a second composition that comprises at least 10% (w/v) sugar; and (b) lyophilizing the second composition.

The present invention includes methods of preventing and treating an anthrax infection comprising administering to a subject a pharmaceutically effective amount of one of the vaccines of the invention. In another embodiment, the invention includes methods of inducing an immune response in a subject comprising administering to the subject a vaccine of the invention.

The present invention provides method for lyophilizing a vaccine comprising (i) freezing a composition of the invention and (ii) subjecting the frozen composition to sublimation.

BRIEF DESCRIPTION OF THE DRAWINGS

FIGS. 17A-D. Graphs showing the comparison of NF50 at dose level 0.25 (Panel A), 0.125 (Panel B), 0.0625 (Panel C) and 0.03125 (Panel D) for LyoA stored at 5, 25, and 40° C. for one month.

FIGS. 18A-D. Graphs showing the comparison of NF50 at dose level 0.25 (Panel A), 0.125 (Panel B), 0.0625 (Panel C) and 0.03125 (Panel D) for LyoB stored at 5, 25, and 40° C. for one month.

FIGS. 19A-D. Graphs showing the comparison of NF50 at dose level 0.25 (Panel A), 0.125 (Panel B), 0.0625 (Panel C) and 0.03125 (Panel D) for LyoC stored at 5, 25, and 40° C. for one month.

FIGS. 20A-D. Graphs showing the comparison of NF50 at dose level 0.25 (Panel A), 0.125 (Panel B), 0.0625 (Panel C) and 0.03125 (Panel D) for liquid rPA stored at 5, 25, and 40° C. for one month.

DETAILED DESCRIPTION

Figure 1:
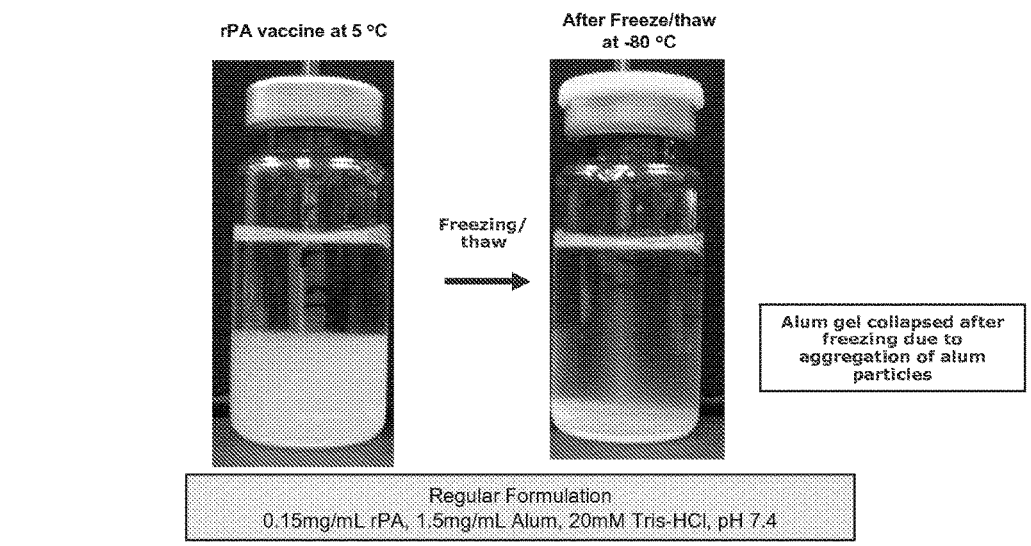
FIG. 1. A photograph of an rPA vaccine without a sugar stabilizer at 2°-8° C. compared to the same composition frozen at −80° C. and thawed.

For many years it has been believed that alum containing vaccines cannot be frozen. Accordingly, alum containing vaccines are not frozen or lyophilized (requires freezing), and alum-containing liquid vaccines are typically discarded if a break in the cold chain causes freezing. The inventors of the present invention made the exciting discovery that when a sugar such as trehalose or sucrose makes up about 20% (w/v) or more of an anthrax vaccine composition, the alum in the composition does not collapse as a result of freezing or thawing. Alum collapse is easy to identify and is associated with loss of vaccine potency and particle aggregation.

The inventors also identified additional stabilizing ingredients and process parameters that help prevent and reduce alum gel collapse. By adding amino acids to a formulation for instance, the amount of sugar required to prevent alum gel collapse can be reduced, e.g., to about 10% (w/v). Process changes that have a positive effect on alum gel height include freezing suspended particles (rather than settled particles) and increasing the freeze rate.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents defines a term that contradicts that term's definition in the application, the definition that appears in this application controls.

The use of the singular includes the plural unless specifically stated otherwise. The word "a" or "an" means "at least one" unless specifically stated otherwise. The use of "or" means "and/or" unless stated otherwise. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components comprising more than one unit unless specifically stated otherwise. The word "about" means within about 1 unit.

As used herein, Protective Antigen (PA) or recombinant Protective Antigen (rPA) is the component of anthrax toxin (approximately 83 kDa) that contains the receptor-binding and translocation domains. One example of a full length PA amino acid sequence is:

(SEQ ID NO: 1)
EVKQENRLLNESESSSQGLLGYYFSDLNFQAPMVVTSSTTGDLSIPSSEL

ENIPSENQYFQSAIWSGFIKVKKSDEYTFATSADNHVTMWVDDQEVINKA

SNSNKIRLEKGRLYQIKIQYQRENPTEKGLDFKLYWTDSQNKKEVISSDN

LQLPELKQKSSNSRKKRSTSAGPTVPDRDNDGIPDSLEVEGYTVDVKNKR

TFLSPWISNIHEKKGLTKYKSSPEKWSTASDPYSDFEKVTGRIDKNVSPE

ARHPLVAAYPIVHVDMENIILSKNEDQSTQNTDSQTRTISKNTSTSRTHT

-continued

SEVHGNAEVHASFFDIGGSVSAGFSNSNSSTVAIDHSLSLAGERTWAETM

GLNTADTARLNANIRYVNTGTAPIYNVLPTTSLVLGKNQTLATIKAKENQ

LSQILAPNNYYPSKNLAPIALNAQDDFSSTPITMNYNQFLELEKTKQLRL

DTDQVYGNIATYNFENGRVRVDTGSNWSEVLPQIQETTARIIFNGKDLNL

VERRIAAVNPSDPLETTKPDMTLKEALKIAFGFNEPNGNLQYQGKDITEF

DFNFDQQTSQNIKNQLAELNATNIYTVLDKIKLNAKMNILIRDKRFHYDR

NNIAVGADESVVKEAHREVINSSTEGLLLNIDKDIRKILSGYIVEIEDTE

GLKEVINDRYDMLNISSLRQDGKTFIDFKKYNDKLPLYISNPNYKVNVYA

VTKENTIINPSENGDTSTNGIKKILIFSKKGYEIG.

SEQ ID NO: 1 is the amino acid sequence of rPA102, e.g., expressed from plasmid pPA102. During secretion of rPA102 from *B. anthracis* ΔSterne-1(pPA102)CR4 into the extracellular space, the first 29 amino acids (the signal peptide) are removed yielding the mature rPA protein of 735 amino acids (82,674 Da). The mature rPA sequence is underlined (SEQ ID NO: 2).

The rPA102 amino acid sequence is but one example of one particular anthrax protein within the scope of the invention. Additional amino acid sequences of PA proteins, including native proteins, from various strains of anthrax are known in the art and include, for example, GenBank Accession Nos: NP_652920.1, ZP_02937261.1, ZP_02900013.1, ZP_02880951.1 which are incorporated by reference. Various fragments, mutations, and modifications in PA to reduce its toxicity or to improve its expression characteristics are also known, such as those described elsewhere in the specification, as are various fusion proteins. Those fragments, mutants, and fusion proteins are included in the term "PA" unless the context or text clearly indicates that those forms are excluded. Where indicated, PA fragments, mutants, and fusion proteins (whether with full length PA or a PA fragment) are those that elicit an antisera that is active in the toxin neutralization assay (TNA).

As used herein, "temperature stable," "stable" or "stability" refers to the stability of the alum gel and potency of a vaccine after a freeze/thaw cycle. A stable vaccine as used herein is a vaccine that exhibits no or little decrease in activity and/or potency and/or alum gel collapse and/or particle aggregation after a freeze/thaw cycle as compared to a comparable liquid vaccine that is kept between 2°-8° C. Stability can be measured using any one or more of the assays described herein, including the working examples, as well as assays known in the art that are used to measure activity, potency and/or peptide degradation.

In certain embodiments, the immunogenicity of an antigen or vaccine, e.g., protective antigen, can be measured by calculating 50% neutralization factor (NF50). The geometric mean of the NF50 (GeoMean or <NF50>gm) for vaccine formulation can be calculated based on the NF50 values from a given number of data points. In certain embodiments, the NF50 and/or GeoMean is determined by using serum samples from a standard Toxin Neutralization Assay (TNA) (Hering et al., Biologicals 32 (2004) 17-27; Omland et al., Clinical and Vaccine Immunology (2008) 946-953; and Li et al., Journal of Immunological Methods (2008) 333:89-106), e.g., serum from immunized mice or rabbits. The dilution of serum resulting in 50% neutralization of toxin is the "ED50". The neutralization capacity of each test serum in relation to that of a reference serum (50% neutralization factor, or NF50, also known as the neutralization ratio) is calculated from the quotient of the ED50 of the reference serum and the ED50 of the test serum, i.e., the neutralization factor, NF50 is calculated as follows:

$$NF50 = \frac{ED50_{sample}}{ED50_{reference}}$$

In certain embodiments, a T-test or one-way ANOVA can be used to compare the geometric mean of NF50 from different formulation at the 95% confidence level. In one embodiment, if the p value of the GeoMean NF50 is larger than 0.05, there is no significant difference in NF50 among the formulations. In another embodiment, if the p value is less than 0.05, the geometric mean NF50 among the formulations is significantly different from each other.

Neutralization factor (NF50) calculations from mouse potency assay experiments show that the NF50 values and thus potency correlate with alum gel collapse. Accordingly, stability can be assessed by observing and measuring the alum gel of a vaccine that has been frozen overnight at −80° C. and then allowed to thaw at room temperature. A stable vaccine will exhibit little to no alum gel collapse as compared to a control vaccine (same composition but stored at 2°-8° C.). Alum gel height can be measured and a % difference between the frozen/thawed sample and 2°-8° C. control can be determined. In one embodiment, a difference of about less than 1%, 2%, 3%, 5%, 8%, 10% or 12% indicates a stable vaccine.

Stability can also be assessed by assaying the composition after freezing for intact protein (e.g., rPA intact with alum) or, conversely, desorbed protein (e.g., rPA desorbed from alum. For instance, stability can be determined by assaying and characterizing free rPA102 (release) by ELISA; protein structure by, for instance, differential scanning calorimetry and intrinsic fluorescence; desorbed free protein by $A_{280}$; purity and backbone degradation by SDS-PAGE, SEC and or RP-HPLC; charge variation by IEX or isoelectric focusing; and biochemical activity by microphage lysis assay (MLA).

In one embodiment, a temperature stable vaccine is a vaccine that after being exposed to freeze/thaw conditions (e.g., frozen vaccine or lyophilized vaccine), exhibits potency that is the same or at least about 98%, at least about 95%, at least about 93%, at least about 90%, at least about 88% or at least about 85% the same as a comparable liquid vaccine stored at about 2°-8° C. In one embodiment, an anthrax mouse potency assay is used to determine whether a frozen or lyophilized vaccine is potent.

In some embodiments, a composition retains at least 80%, at least 90% or at least 95% immunogenicity after storage in lyophilized form for at least 1 month at 40° C.

The vaccines of the invention are temperature stable vaccines. The temperatures over which a formulation of the invention is stable are generally below about 30° C., but may be above 30° C., 35° C., 40° C., 45° C., or 50° C. In some embodiments, the formulation's stability is in reference to a temperature below about 25° C., about 20° C., about 15° C., about 10° C., about 8° C., about 5° C., about 4° C., or about 2° C. Thus, in some embodiments, the temperature is in the range of about 25° C. to about −10° C., about 20° C. to about −10° C., about 15° C. to about −10° C., about 10° C. to about −10° C., about 8° C. to about −10° C., about 5° C. to about −10° C., about 15° C. to about −5° C., about 10° C. to about −5° C., about 8° C. to about −5° C., and about 5° C. to about −5° C.

The Examples section describes various methods for determining stability. In some embodiments, a vaccine of the invention shows no statistically significant decrease in stability after freeze thaw as compared to the same sample but fresh and/or stored 5° C. In some embodiments, a vaccine of the invention shows no statistically significant decrease in stability, immunogenicity, potency or any combination thereof after storage at −80° C., −20° C., 25° C., 40° C. and/or 50° C. for 1, 2, 3, 4, 5, 6, 9 12, 18, 24, 30, 36, 42, 48, 54 or 60 months as compared to storage at 5° C. for the same time period.

In some embodiments, the stability of a composition is measured by microphage lysis assay (MLA), size exclusion chromatography (SEC-HPLC) and/or anion exchange chromatography (AEX-HPLC).

In some embodiments, a composition retains at least 80%, at least 90% or at least 95% purity after storage in lyophilized form for at least 4 months at 50° C.

The vaccine compositions of the invention contain an antigen which is adsorbed to an aluminium adjuvant (alum) and an amount of sugar necessary to stabilize the formulation. For instance, the vaccine formulations disclosed herein exhibit little to no reduction in potency after exposure to freeze/thaw conditions when compared to a similar liquid vaccine that has been maintained at between 2°-8° C. and/or exhibit little to no collapse of alum gel.

The aluminium adjuvant (alum) can be, for instance, aluminium hydroxide, aluminium phosphate or aluminium sulphate. In one embodiment, the adjuvant is aluminium hydroxide (e.g., ALHYDROGEL™). The amount of aluminium can vary quite a bit with apparently no effect on the stability of the alum gel (in other words, increasing the amount of alum in the composition does not appear to increase the likelihood that the alum gel will collapse). In one embodiment of the invention, the vaccine composition comprises about 1-10 mg/ml aluminium hydroxide. In another embodiment, the composition comprises about 1.5 to 5 mg/ml aluminium hydroxide. In another embodiment, the vaccine composition comprises about 1.5, 2, 2.5, 3, 3.5, 4, 4.5 or 5 mg/ml aluminium hydroxide.

It is believed that the stable vaccine compositions of the invention can be used to stabilize any antigen that is formulated with alum. For instance, the antigen can be a B. anthracis recombinant Protective Antigen (rPA) or a cell-free filtrate from an avirulent B. anthracis strain such as V770-NP1-R (e.g., anthrax vaccine adsorbed).

Methods of expressing B. anthracis proteins, including PA (as well as fragments, mutants, and fusion proteins) are described, for example in U.S. Pat. No. 7,201,912, to Park and Giri, U.S. Pat. No. 6,387,665 to Ivins et al., U.S. Pat. No. 6,316,006 to Worsham et al., and U.S. Pat. No. 7,261,900 to Leppla et al., each of which is incorporated by reference in its entirety. For example, as described in U.S. Pat. No. 7,201,912, pBP103 is an expression vector for full-length, wild-type rPA. The PA sequence from pBP103 is identical to that of wild-type PA.

Some embodiments of the invention include formulations comprising PA expressed in B. anthracis, including expression in either sporulating or non-sporulating strains of B. anthracis or both. For instance, the PA can be derived from non-sporulating B. anthracis strain ASterne-1 (pPA102)CR4 (i.e., rPA102). See, for instance, U.S. Pat. Nos. 6,316,006 and 6,387,665, both to Ivins et al., each of which is herein incorporated by reference in its entirety. Some compositions of the invention comprise a PA from the avirulent B. anthracis strain V770-NP1-R The formulations of the invention may also include B. anthracis PA expressed by a heterologous organism. For instance, the invention includes PA expressed in E. coli.

In addition, various PA fragments, mutants, and fusion proteins have also been described and can be used in the current formulations. For example, PA may be modified to lack a functional binding site, thereby preventing PA from binding to either Anthrax Toxin Receptor (ATR) (see Bradley, K. A., Nature (2001) 414:225-229) to which native PA binds, or to native LF. By way of example, a modification made within or near to amino acid residues 315-735 or within or near to residues 596-735 of Domain 4 may render PA incapable of binding to ATR. Alternatively (or in addition), the PA furin cleavage site "RKKR" (SEQ ID NO: 3), which in most full length PA sequences is found at or around residues 163-168, may be inactivated by deletion, insertion, or substitution within or near to the furin cleavage site. For example, all of the furin cleavage site residues of native PA may be deleted. Other mutant PAs include those in which the dipeptide Phe-Phe has been modified to render the PA resistant to chymotrypsin. A PA fragment or PA fusion protein may also be a PA mutant.

Specific examples of PA fragments include those in U.S. Pat. No. 7,201,912, for example, PA64 expressed by pBP111, PA47 expressed by pBP113, PA27 expressed by pBP115. Some of those fragments may also include mutations to, for example, eliminate the furin cleavage site RKKR (SEQ ID NO: 3) or the chymotrypsin sensitive site formed by the dipeptide sequence Phe-Phe (FF). In addition, fragments may include one or two additional amino acids at the N-terminus. Examples of fusion proteins involving PA include those in U.S. Pat. No. 7,201,912, for example the PA-LF fusion proteins expressed by plasmids pBP107, pBP108, and pBP109. The invention also includes formulations comprising a HIS-tag PA. When a fragment, mutant, or fusion protein is used, however, it is generally desirable that the fragment, mutant, or fusion protein elicit protective immunity to a challenge with, e.g., an $LD_{50}$, of anthrax spores of the Ames strain in one or more of mice, guinea pigs, or rabbits.

PA from a recombinant source and/or a non-recombinant source can be used and the stability of such preparations improved by the formulations of the invention.

In one embodiment, a vaccine composition comprises about 75 to 750 µg/ml, 100 to 500 µg/ml, 100 to 250 µg/ml, 100 to 750 µg/ml or 250 to 750 µg/ml of antigen, e.g., rPA. For instance, the invention includes a vaccine comprising about 150, 200, 250, 300, 350, 400, 450 and 500 µg/ml of antigen, e.g., rPA. In some embodiments, the vaccine comprises approximately 175 µg antigen (e.g., rPA) per 1500 µg aluminum hydroxide. In some embodiments, the vaccine comprises approximately 200 µg/mL antigen (e.g., rPA) and about 0.5 mg/mL aluminum hydroxide. In further embodiments, the vaccine comprises approximately 250 µg antigen (e.g., rPA) per 100 to 250 µg aluminum hydroxide. In some embodiments, an antigen is an Anthrax antigen such as protective antigen. In some embodiments, a protective antigen is at least about 80%, about 83%, about 85%, about 88%, about 90%, about 93%, about 95%, about 96%, about 97%, about 98%, or about 99% identity to the polypeptide of SEQ ID NO: 2. Some compositions of the invention comprise about 150-500 µg/ml protective antigen or about 150, 175, 200, 225, 250, 275, 300, 325, 400, 375, 400, 425, 450, 475 or 500 µg/ml protective antigen.

In some embodiments a composition of the invention contains about 0.5 to 1.5 mg/ml aluminum hydroxide. In some embodiments, a composition contains about 0.5 mg/ml or about 1.5 mg/ml aluminum hydroxide.

In some embodiments, an aluminum adjuvant is selected from the group consisting of aluminum hydroxide, aluminum phosphate and aluminum sulfate.

An anthrax vaccine of the invention, whether it be a vaccine comprising rPA or a cell-free filtrate from an avirulent *B. anthracis* strain, can be administered to a subject pre-exposure or post-exposure to *B. anthracis*. When administered post-exposure, the vaccine may be administered in conjunction with antibiotics.

In another embodiment, the antigen is a protein (e.g., recombinant) based antigen selected from the group consisting of hepatitis B protective antigens, *Clostridium botulinum* neurotoxin protein, Herpes Simplex Virus antigens, Influenza antigens, Congenital cytomegalovirus antigens, Tuberculosis antigens, HIV antigens, Diphtheria antigens, Tetanus antigens, Pertussis antigens, *Staphylococcus* enterotoxin B (SEB), and *Yersinia pestis* protective antigens and F1-V fusion protein. Antigens can be derived, for instance, from papillomavirus (e.g., HPV), influenza, a herpesvirus, a hepatitis virus (e.g., a hepatitis A virus, a hepatitis B virus, a hepatitis C virus), *Meningococcus* A, B and C, *Haemophilus* influenza type B (HIB), *Helicobacter pylori, Vibrio cholerae, Streptococcus* sp., *Staphylococcus* sp., *Clostridium botulinum, Bacillus anthracis* and *Yersinia pestis*. In some embodiments, a vaccine of the invention is a pneumococcal vaccine, a diphtheria-tetanus-acellular pertussis (DTaP) vaccine, a *haemophilus influenzae* type b vaccine, a Hib/Hep B vaccine, Hepatitis A vaccine, a Hepatitis B vaccine, a Hep A/Hep B vaccine, a DTaP/inactivated polio/Hep B vaccine, a DTaP/inactivated polio/Hib vaccine, a human papillomavirus (HPV) vaccine, a Japanese Encephalitis (JE) vaccine.

The vaccines of the present invention can withstand freezing overnight at −80° C. with little to no loss of potency or collapse of alum gel. The invention includes frozen liquid vaccines as well as lyophilized vaccines (also referred to herein as freeze dried vaccines). As disclosed herein, the lyophilization process includes the freezing of a liquid composition. The frozen composition is then subjected to sublimation under freezing. For the lyophilized vaccines, the disclosed vaccine components and amounts refer to the amounts used in the liquid composition that is then subjected to freezing and not necessarily the dried lyophilized cake or reconstituted vaccine. The final lyophilized vaccine cake (a dry composition) may contain different percentages of components due to the drying process.

The present invention provides method for lyophilizing a vaccine comprising (i) freezing a composition of the invention and (ii) subjecting the frozen composition to sublimation.

In one embodiment, the vaccine of the invention comprises about 20% or more of a glass forming agent such as sugar. In one embodiment, the glass-forming agent is a reducing sugar. In one embodiment, the vaccine comprises a non-reducing sugar such as trehalose or sucrose. In one embodiment, the glass forming agent is trehalose or sucrose. If the vaccine is lyophilized, it may be preferable to use no more than about 40% sugar, prior to lyophilization, so that the vaccine forms a cake-like composition. The vaccine may comprise about 15%, 16%, 17%, 18%, 19%, 20%, 21%, 22%, 23%, 24%, 25%, 26%, 27%, 28%, 29%, 30%, 35% or 40% sugar, e.g., prior to lyophilization. In one embodiment, the vaccine composition comprises about 10-40%, 10-35%, 10-30%, 10-25%, 10-20%, 35-40%, 30-40%, 25-40%, 20-40%, 15-40%, 20-30%, 20-25%, 25-30%, 25-35%, 21-40%, 21-35%, 21-30% 21-25% or greater than 10%, 15%, 20%, 21%, 22%, 23%, 24%, 25%, 26%, 27%, 28%, 29%, 30%, 31%, 32%, 33%, 34%, 35%, or 36% (w/v) sugar, e.g., prior to lyophilization. In some embodiments, a composition contains greater than about 15%, 16%, 17%, 18%, 19%, 20%, 21%, 22%, 23%, 24% and 25% (w/v) sugar, e.g., prior to lyophilization.

As disclosed herein, the inventors of the present invention have identified that alum vaccine compositions comprising at least about 20% trehalose or sucrose can withstand freeze/thaw conditions. When certain additional stabilizing agents are added (e.g., a surfactant and/or amino acid) and/or the process improvements disclosed herein are incorporated (e.g., increasing freeze rate, freezing of suspended particles), the amount of sugar can be reduced to about 15% (w/v) or even about 10% (w/v) without affecting potency of the vaccine.

In one embodiment of the invention, a vaccine composition comprising an antigen adsorbed to an aluminium adjuvant and a sugar (e.g., 15% w/v or more) also contains a solubilizing agent such as a surfactant, e.g., prior to lyophilization. In one embodiment, the surfactant is a non-ionic detergent such as polysorbate 80 (e.g., TWEEN® 80). In one embodiment, the vaccine composition comprises between about 0.001% and about 0.05% surfactant (such as polysorbate 80). In one embodiment, the composition comprises about 0.020%, about 0.025% or about 0.020% to 0.025% (w/v) surfactant (such as polysorbate 80). Other surfactants that can be used include, but are not limited to, polysorbate 20, pluronic L68, polyoxyethylene 9-10 nonyl phenol (e.g., TRITON™ N-101, octoxylnol 9), TRITON™ X-100, and sodium dexoycholte. In one embodiment, the surfactant is removed during the manufacturing process so that no surfactant is present in the final drug product. In one embodiment, a surfactant is present during freezing, e.g., of lyophilization process. In some embodiments, a formulation of the invention does not comprise a surfactant.

The inventors have found that the percentage of sugar may be reduced to as much as about 10% (w/v) with little to no effect on potency and/or little to no alum gel collapse if amino acids (for instance, alanine, arginine, glycine and proline) are added to the composition, e.g., prior to freezing and/or lyophilization. The amount of amino acid added to the vaccine composition can vary. In one embodiment, the vaccine composition comprises 0.5 to about 15% (w/v) of an amino acid or combination of amino acids. In one embodiment, the vaccine composition comprises about 2-10% (w/v) of an amino acid or combination of amino acids. In one embodiment of the invention, the vaccine comprises about 2% arginine or alanine. In another embodiment of the invention, the vaccine comprises about 10% glycine. Is some embodiments, a vaccine composition comprises about 2-10%, 2-8%, 2-6%, 2-4%, 2-3%, 3-10%, 5-10%, 7-10%, 2.5-5%, 3-5%, 3-7%, or 4-6% (w/v) of an amino acid or combination of amino acids. In some embodiments, two, three or more amino acids are present, such as selected from alanine, glycine, proline and/or arginine. In some embodiments, a composition contains about 0.5-4%, 1-4%, 1.5-4%, 2-4%, 2.5-4%, 3-4%, 3.5-4%, 0.5-1%, 0.5-1.5%, 0.5-2%, 0.5-2.5%, 0.5-3%, 0.5-3.5%, 0.5-4%, 1-3%, 1-2%, 2-3%, or 1.5-2.5% (w/v) alanine or arginine. In some embodiments, a composition contains about 2%, 1.75%, 2.25%, 2.5%, 2.75%, 3%, 3.25%, 3.5%, 3.75% or 4% (w/v) alanine or arginine. In some embodiments, a composition contains about 6-12%, 7-12%, 8-12%, 9-12%, 10-12%, 11-12%, 6-11%, 6-10%, 6-9%, 6-8%, 6-7%, 7-11%, 8-10%, 7-10%, 11-9%, 7- 8%, 8-9% or 9-10% (w/v) glycine. In some embodiment, a composition contains about 6%, 7%, 8%, 9%, 10%, 11% or 12% (w/v) glycine. In some embodiments, the recited concentration of amino acid is prior to freezing and/or lyophilization.

In some embodiments, a formulation does not comprise an amino acid(s) solution or does not contain an amino acid(s), other than the amino acids that are part of the polypeptide antigen.

In some embodiments, the formulation further comprises one or more additional ingredients. For example, the formulation may include one or more salts, such as sodium chloride, sodium phosphate, or a combination thereof. In general, each salt is present in the formulation at about 10 mM to about 200 mM.

The vaccine formulations may contain a buffer such as 20 mM TRIS-HCL. The pH of the formulation may also vary. In general, it is between about pH 6.2 to about pH 8.0. In one embodiment, the pH of the vaccine is about 7.4.

In another embodiment, the formulation further comprises a sugar alcohol such as sorbitol. In one embodiment, the formulation comprises 0.25% sorbitol.

In some embodiments, compositions and vaccine formulations of the invention may contain additional adjuvants, for instance, ImmunoStimulatory Sequences (ISS, CpG), and calcium phosphate. For ISS, protein samples are generally used at a final protein concentration 50 µg/ml. Other non-limiting examples of adjuvants include, but are not limited to: CGP7909 (e.g., see U.S. Pat. No. 7,223,741, which is herein incorporated by reference in its entirety), CpG1018 (see, for instance, US 2010/0183675, which is herein incorporated by reference in its entirety), Glucopyranosyl Lipid Adjuvant (GLA), PolyI PolyC (PIPC), N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19840A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN 80 emulsion.

The invention includes compositions comprising the following formulations: 0.15 mg/mL antigen, 1.5 mg/mL aluminium, 20% trehalose, 2% alanine and 0.025% surfactant; 0.5 mg/mL antigen, 5 mg/mL aluminium, 20% trehalose, 2% alanine and 0.025% surfactant; 0.5 mg/mL antigen, 5 mg/mL aluminium, 20% trehalose, 1% sucrose, 2% alanine and 0.025% surfactant; and 0.5 mg/mL antigen, 5 mg/mL aluminium, 20% trehalose, 2% alanine and 0.025% surfactant. In some embodiments the antigens and/or surfactants in the these formulations are PA and TWEEN® 80, respectively. In some embodiments, a composition of the invention comprises 5 mM NaPi, pH 7.0 buffer or 20 mM Tris, pH 7.4. Other compositions included in the invention are described in the Examples.

Methods of the invention can be used to produce stable lyophilized vaccines. In some embodiments, a stable lyophilized vaccine can be produced from a liquid vaccine/composition (e.g., a commercially prepared vaccine) that contains at least one antigen adsorbed to an aluminum adjuvant by causing the liquid vaccine to contain (i) at least 20% (w/v) non-reducing sugar; (ii) a surfactant and at least 15% (w/v) sugar; (iii) an amino acid and at least 10% (w/v) sugar; or (iv) a surfactant, an amino acid and at least 10% (w/v) sugar. This may be accomplished by adding the respective compound(s) directly to the liquid vaccine. In some cases, this may not be practical because adding the respective compounds, such as sugar, to the required concentration may increase the osmolality of the composition to a level not acceptable for injection, administration or vaccination. This may also be accomplished by exchanging at least part of the liquid component of the liquid vaccine with a second liquid component that contains the respective compounds to create a second liquid vaccine/composition comprising (i) at least 20% (w/v) non-reducing sugar; (ii) a surfactant and at least 15% (w/v) sugar; (iii) an amino acid and at least 10% (w/v) sugar; or (iv) a surfactant, an amino acid and at least 10% (w/v) sugar and then lyophilizing the second liquid vaccine/composition. Any method may be used to exchange at least part the liquid component of the first composition to create the second composition that comprises (i) at least 20% (w/v) non-reducing sugar; (ii) a surfactant and at least 15% (w/v) sugar; (iii) an amino acid and at least 10% (w/v) sugar; or (iv) a surfactant, an amino acid and at least 10% (w/v) sugar. For example, this can be accomplished by centrifugation which pellets the at least one antigen adsorbed to an aluminum adjuvant and allows the liquid component to be removed or separated from the pellet. It can also be accomplished by filtering methods that allow the liquid component to pass through the filtration membrane, but not the at least one antigen adsorbed to an aluminum adjuvant. In some embodiments, this could be accomplished with, but not limited to, a centrifugation filter, a vacuum filter or a tangential flow filter. In some embodiments, a tangential flow filter with a small molecular cut off size, such as 3-30K, may be used, for example, to remove water, to retain any free antigen not bound to another component and/or retain the at least one antigen adsorbed to an aluminum adjuvant. A free antigen could be one not bound to an aluminum adjuvant.

If there is a significant amount of unbound or free antigens (e.g., not bound to an aluminum adjuvant) whose retention is desired or advantageous, it may be preferable to use techniques other than centrifugation such as tangential flow method. In some embodiments, a filter with a small molecular cut off size such as 3-30K is used. This can be used to reduce water or liquid content and small MW excipients but retain the larger molecular weight excipient(s) such as protein and/or bound antigen.

The second liquid component could be made from at least part of the original liquid component of the liquid vaccine. For example, once at least part of the original liquid component is separated or separable from the part with the antigen adsorbed to an aluminum adjuvant, one can add (i) a non-reducing sugar; (ii) a surfactant and a sugar; (iii) an amino acid and a sugar; or (iv) a surfactant, an amino acid and a sugar to the separated liquid component to create the second liquid component, so that once this second liquid component is added back to the part/component with the antigen adsorbed to an aluminum adjuvant a second composition that comprises (i) at least 20% (w/v) non-reducing sugar; (ii) a surfactant and at least 15% (w/v) sugar; (iii) an amino acid and at least 10% (w/v) sugar; or (iv) a surfactant, an amino acid and at least 10% (w/v) sugar is produced. This second composition can then be frozen, and optionally lyophilized to produce a stable lyophilized vaccine. These methods are particularly useful because they can be used in combination with methods already used to make liquid vaccines. For example, an anthrax vaccine, a pneumococcal vaccine, a diphtheria-tetanus-acellular pertussis (DTaP) vaccine, a *haemophilus influenzae* type b vaccine, a Hib/Hep B vaccine, Hepatitis A vaccine, a Hepatitis B vaccine, a Hep A/Hep B vaccine, a DTaP/inactivated polio/Hep B vaccine, a DTaP/inactivated polio/Hib vaccine, a human papillomavirus (HPV) vaccine or a Japanese Encephalitis (JE) vaccine may be converted to a lyophilized vaccine using methods of the invention.

Figure 22:
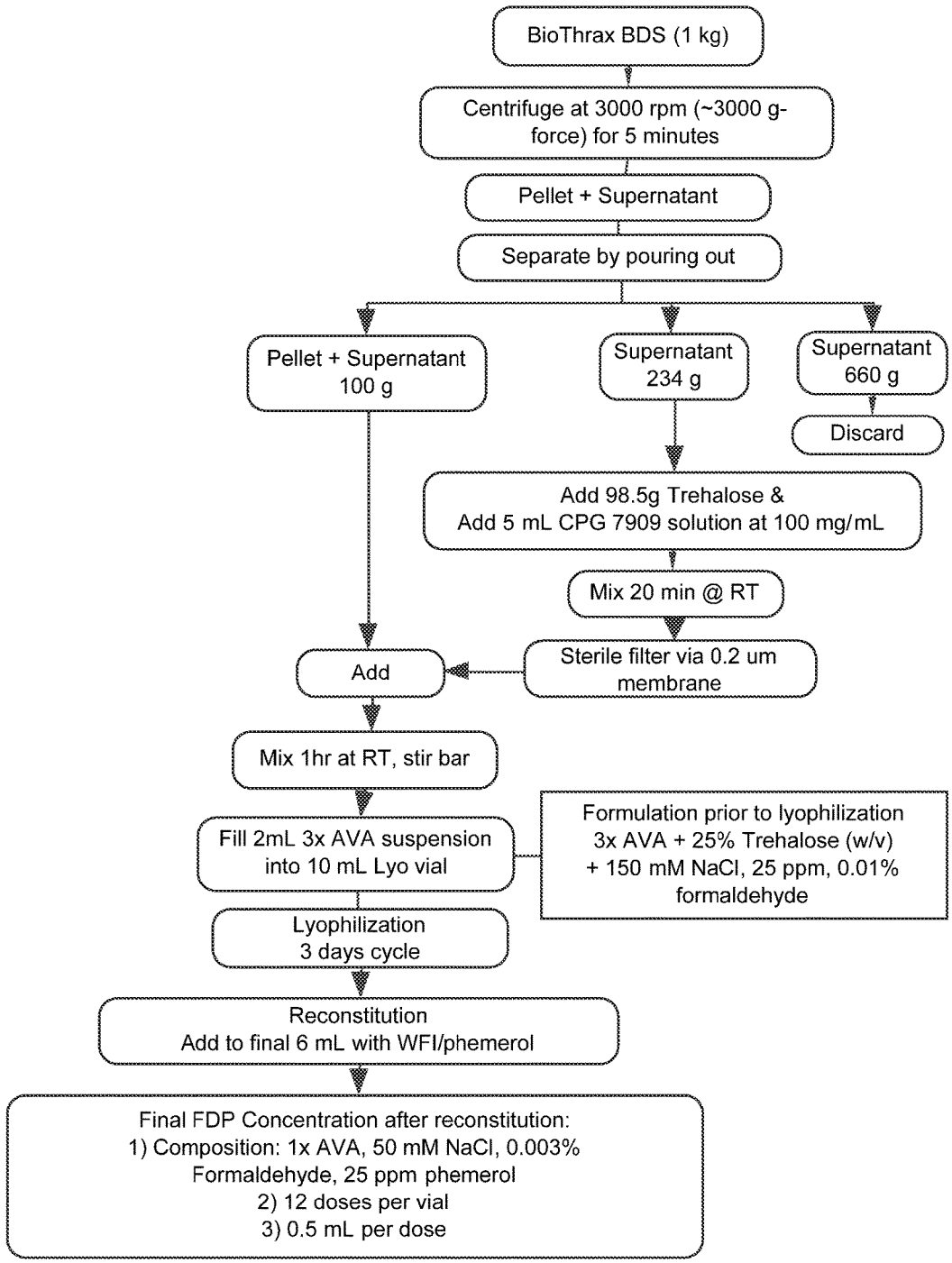
FIG. 22 shows an example of a process flow chart for lyophilizing a BIOTHRAX® based vaccine containing CPG 7909. BDS=bulk drug substance; g=grams; RT=room temperature; WFI=water for injection; AVA=Anthrax Vaccine Adsorbed.

A related method is demonstrated in Example 10, wherein a BIOTHRAX® liquid vaccine is converted to a lyophilized composition. The method is Example 10 can generally be used for other liquid vaccines. A flow chart for a method of the invention is shown in FIG. 22. While this flow chart is tailored to converting liquid BIOTHRAX® vaccine to a lyophilized vaccine, the methods in the flow chart can be adapted for any liquid vaccine comprising at least one antigen adsorbed to an aluminum adjuvant.

Some embodiments of the invention, include methods of preparing a stable lyophilized vaccine, the method comprising (a) exchanging at least part of a liquid component of a first composition comprising at least one antigen adsorbed to an aluminum adjuvant with a second liquid component comprising a non-reducing sugar to create a second composition that comprises (i) at least 20% (w/v) non-reducing sugar; (ii) a surfactant and at least 15% (w/v) sugar; (iii) an amino acid and at least 10% (w/v) sugar; or (iv) a surfactant, an amino acid and at least 10% (w/v) sugar is produced. The second composition can subsequently be frozen and/or lyophilized. In some embodiments, the at least one antigen adsorbed to an aluminum adjuvant is resuspended in the second liquid. In some embodiments, the exchanging comprises separating the liquid component of the first composition from the solid component of the first composition. In some embodiments, the exchanging comprises centrifuging the first composition and separating at least part of the liquid component of the first composition from the pelleted component of the first composition. Alternatively, the exchanging may comprise filtering the first composition to separate at least part of the liquid component of the first composition from the solid component of the first composition. In some embodiments, the second liquid component is created by adding the non-reducing sugar to at least a portion of the liquid component of the first composition. In some embodiments, the liquid component of the first composition is removed and replaced with a second liquid component to create a second composition that comprises at least 20% (w/v) non-reducing sugar. In some embodiments, the second liquid component further comprises a surfactant. The aluminum adjuvant may be, but is not limited to, aluminum hydroxide, aluminum phosphate, aluminum sulphate or aluminum potassium (e.g., aluminum potassium sulfate). In some embodiments, the non-reducing sugar is trehalose, sucrose, or a combination thereof. In some embodiments, the second composition contains about 20-40% (w/v) non-reducing and/or contains greater than about 20%, 21%, 22%, 23%, 24% or 25% (w/v) sugar. In some embodiments, the antigen is an Anthrax antigen, e.g., protective antigen and/or a cell-free filtrate from an avirulent *B. anthracis* strain such as V770-NP1-R. In some embodiments, the second composition comprises at least one amino acid, e.g., arginine, alanine, proline, glycine or any combination thereof.

The invention also includes lyophilized compositions, produced using the methods of the invention and any reconstituted compositions that are reconstituted from a lyophilized composition of the invention.

Vaccines of the invention can be prepared for use as injectables. The composition can be a liquid formulation that is temperature stable (e.g., can withstand a freeze/thaw cycle) or a frozen composition. The composition may also be used to produce a lyophilized dry powder vaccine which can be reconstituted, e.g., with a pharmaceutically acceptable carrier prior to administration. Vaccine administration is generally by conventional routes, for instance, intravenous, subcutaneous, intraperitoneal, or mucosal routes. The administration may be by parenteral injection, for example, a subcutaneous or intramuscular injection.

In some embodiments, a composition of the invention is subjected to freezing and followed by sublimation under vacuum to produce a lyophilized composition.

The term "reconstituted" or "reconstitution" refers to the restoration of a lyophilized form to a liquid form, e.g., by rehydration, of a substance previously altered for preservation and/or storage, e.g., the restoration to a liquid state of a lyophilized rPA formulation of the application that has been stored. A lyophilized composition of the present application can be reconstituted in any aqueous solution which produces a stable, aqueous solution suitable for administration. Such an aqueous solution includes, but is not limited to, sterile water, TE (Tris EDTA), phosphate buffered saline (PBS), Tris buffer or normal saline. A lyophilized sample can be reconstituted with a lower, the same or higher volume than was used to lyophilize the sample.

It should be understood that a dose of a reconstituted lyophilized vaccine formulation of the application can be determined in light of various relevant factors including the conditions to be treated, the chosen route of administration, the age, sex and body weight of the individual patient, and the severity of the patient's symptom, and can be administrated in a single dose, divided dose or multiple doses.

The vaccines are administered in a manner compatible with the dosage formulation, and in such amount as will be prophylactically and/or therapeutically effective. The quantity to be administered, which is generally in the range of 5 µg to 500 µg of antigen per dose, depends on the subject to be treated, capacity of the subject's immune system to synthesize antibodies, and the degree of protection desired. In one embodiment, the vaccine comprises at least about 10 µg PA, 25 µg PA, 50 µg PA, 75 µg PA, 100 µg PA, 125 µg PA, 150 µg PA, 200 µg PA, 225 µg PA, 250 µg, 275 µg, 300 µg PA. Precise amounts of antigen are dependent on the antigen to be delivered.

The vaccine may be given in a single dose schedule, or optionally in a multiple dose schedule. The vaccine composition may be administered, for instance, in a 0.5 mL dose. For pre-exposure prophylaxis, a multiple dose schedule is one in which a primary course of vaccination may be with 1-6 separate doses, followed by other doses given at subsequent time intervals to maintain and or reinforce the immune response, for example, at 1-4 months for a second dose, and if needed, a subsequent dose(s) after several months.

For post-exposure prophylaxis, the vaccine may also be administered according to a single dose or multiple dose regimen. For instance, in one embodiment, the vaccine is administered in 3 doses at times 0, 2 and 4 weeks post exposure. The dosage regimen will also, at least in part, be determined by the need of the individual, upon the judgment of the practitioner and/or upon results of testing, e.g., measuring levels of immune response to the vaccine/antigen(s) such as antibody levels and/or T-cell activity against the antigen(s).

In addition, the vaccine containing the immunogenic antigen(s) may be administered in conjunction with other immunoregulatory agents, for example, immunoglobulins, antibiotics, interleukins (e.g., IL-2, IL-12), and/or cytokines (e.g., IFN-beta, IFN-alpha).

In one embodiment, the vaccine is administered to a subject post-exposure to anthrax. In this embodiment, the vaccine may be administered in conjunction with an antibiotic. Antibiotics that may be administered with the vaccine include, but are not limited to, penicillin, doxycycline and ciprofloxacin.

The invention includes methods of treating (post-exposure prophylaxis) or preventing (pre-exposure prophylaxis) an anthrax infection comprising administering to a subject a pharmaceutically effective amount of a vaccine of the invention. In one embodiment, the anthrax infection is the result of inhaling anthrax (inhalation anthrax). As used herein, a pharmaceutically effective amount of a vaccine is an amount that induces an immune response. In one embodiment, a pharmaceutically effective amount of a vaccine is an amount comprising at least 25 μg PA. As used herein, a subject is a mammal such as a human.

The invention also provides methods of stimulating an immune response in a subject by administering to the subject an amount of a vaccine of the invention sufficient to stimulate an immune response. In one embodiment, immune stimulation is measured by increases in antibody titer that is specific for the antigen in the vaccine. In still other embodiments, immune stimulation is measured by an increased frequency in cytotoxic T lymphocytes specific for the antigen in the vaccine.

Also provided are methods of vaccinating a subject against a pathogen comprising administering a composition of the invention. Additionally provided are methods of vaccinating a subject against a pathogen comprising administering to a subject a pharmaceutical composition reconstituted from a lyophilized composition of the invention. The invention further includes methods of producing potent, alum based frozen vaccines comprising suspending a composition comprising at least about 10%, at least about 15%, at least about 20%, at least about 21%, at least about 25% or at least about 30% sugar and an antigen adsorbed to an aluminum adjuvant and freezing said composition at a rate sufficient to freeze the suspended composition before sedimentation occurs, e.g., flash freezing.

Some embodiments of the invention provide methods of preparing a stable lyophilized composition, comprising lyophilizing a composition of the invention, wherein the stability of the reconstituted lyophilized composition is measured by microphage lysis assay (MLA), size exclusion chromatography (SEC-HPLC) and/or anion exchange chromatography (AEX-HPLC).

For anthrax vaccines, the immunogenicity of the formulations can be tested as described in the various examples. For example, mice can be immunized with, for example, 10 μg, 20 μg, or more of rPA suspended in an adjuvant emulsion. Control mice are immunized with saline emulsified in adjuvant for use as negative controls. The mice are generally immunized, then bled at various intervals, e.g., day 0, day 21 and day 28 post-immunization. The serum is then analyzed for the presence of specific antibody, e.g., by ELISA, which can also be used to determine the titer of the antisera.

A mouse toxin-neutralizing antibody assay can also be used to determine if the anthrax vaccine formulations elicit protective antibodies. In this assay, mice immunized with an anthrax vaccine (e.g., containing rPA) are then challenged i.p. with 2 lethal doses of lethal toxin (PA and lethal factor (LF)). Four days after challenge, the mice are scored for survivors.

The rPA formulations can also be used to prepare compositions comprising neutralizing antibodies that immunoreact with the anthrax toxin. The resulting antisera can be used for the manufacture of a medicament for treating exposure to anthrax. In one embodiment of the invention, the antibody composition comprises a purified anti-PA antibody. By "purified," it is meant that the antibody is substantially free of other biological material with which it is naturally associated. Purified antibodies of the invention are at least 60% weight pure, at least 70% weight pure, at least 80% weight pure, at least 90% weight pure or at least 95% weight pure. The antisera, or antibodies purified from the antisera, can also be used as diagnostic agents to detect either PA fragments or native protein.

Frozen and lyophilized formulations of the invention can be manufactured with increased potency by increasing the freeze rate. In one embodiment the formulation is flash frozen.

Potency may also be increased by freezing suspended rather than settled compositions. Compositions can be suspended by gentle shaking and freezing (e.g., immediately).

The invention will be further clarified by the following examples, which are intended to be purely exemplary of the invention and in no way limiting.

Example 1: Freeze/Thaw of Liquid rPA and AVA Vaccines with and without Trehalose rPA102 vaccine formulations with and without trehalose were prepared as outlined in Table 1 below.

TABLE 1

Trehalose Formulations for Freeze/Thaw Assay

| Sample | rPA (mg/ml) | ALHYDROGEL (mg/ml) | Buffer | pH | Trehalose | Arginine | TWEEN 80 |
|---|---|---|---|---|---|---|---|
| rPA Control 1 | 0.15 | 1.5 | 20 mM | 7.4 | — | — | — |
| rPA Test 1 | | | TRIS-HCl | | 20% | 2% | 0.025% |

Figure 2:
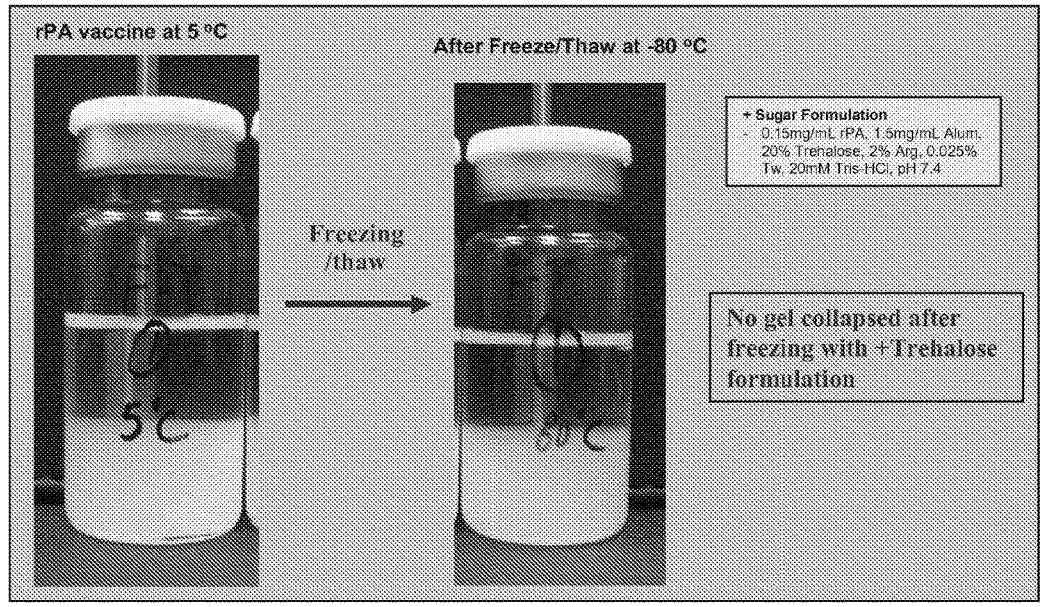
FIG. 2. A photograph of an rPA vaccine with 20% trehalose and 2% arginine at 2°-8° C. compared to the same composition frozen at −80° C. and thawed.

After compounding, each sample was divided into two 8 ml aliquots in 10 ml glass tubes. For each sample, after gentle mixing overnight, one tube was placed at −80° C. and the other tube was placed at 2-8° C. after gentle mixing overnight.

Samples stored at −80° C. overnight were thawed on the lab bench the next day for several hours (>3-4 hours) before observation and comparison to the 2-8° C. samples that were brought to room temperature. Samples were photographed and total liquid height and ALHYDROGEL™ (aluminum hydroxide) height were measured. Regular rPA102 vaccine was compared before and after freeze/thaw. FIG. 1 is a photograph comparing rPA Control 1 sample at 2-8° C. (labeled 5° C.) to the −80° C. sample after thaw. The photograph shows significant collapse of the alum gel in the rPA Control 1 sample subjected to freeze/thaw conditions. The level of sugar in a regular formulation that protected rPA102 from freeze/thaw stress was tested. As shown in FIG. 1, freezing damaged rPA102 vaccine, and the potency (MRPT) data correlated with physio-chemical and gel height (collapsed). FIG. 2 is a photograph comparing rPA Test 1 sample at 2-8° C. (labeled 5° C.) to the −80° C. sample after thaw. There is no noticeable collapse of the alum in the thawed rPA Test 1 sample. Table 2 provides an overview of the relative % alum height.

TABLE 2

Relative % Alum Height

| Formulation | 5° C. | −80° C. |
|---|---|---|
| rPA Control 1 | 100% | 32.6% |
| rPA Test 1 | 100% | 101.5% |

A similar freeze/thaw experiment was performed with a test composition containing 15% trehalose, 0.15 mg rPA/mL, 2% alanine, 0.025% polysorbate 80, 25 mM NaPi, pH 7.4 compared to a control formulation without 15% trehalose with similar result (data not shown).

A vial of BIOTHRAX® (Anthrax Vaccine Adsorbed), AVA, and a vial AVA+25% trehalose were placed in −80° C. after gentle mixing. A second vial of BIOTHRAX® and a second vial of AVA+25% trehalose were placed at 2°-8° C. overnight after gentle mixing. The next day, the −80° C. vials were allowed to thaw and all vials were inspected. The aluminum gel height appeared to be about the same for the BIOTHRAX® stored at 2°-8° C. and the two AVA samples containing 25% trehalose. The aluminum gel height was much lower for BIOTHRAX® stored at −80° C. (no trehalose). (Data not shown).

Example 2: Freeze/Thaw of Liquid rPA Vaccines with and without Sucrose rPA102 vaccine formulations with and without sucrose were prepared as outlined in Table 3 below.

TABLE 3

Sucrose Formulations for Freeze/Thaw Assay

| Sample | rPA (mg/ml) | ALHYDROGEL (mg/ml) | Buffer | pH | Sucrose |
|---|---|---|---|---|---|
| rPA Control 2 | 0.5 | 5 | 20 mM TRIS-HCL | 7.4 | — |
| rPA Test 2 | | | | | 10% |

After compounding, each sample was divided in to two 10 ml aliquots in 10 ml glass tubes. For each sample, one tube was placed at −80° C. after gentle mixing overnight and the other tube was placed at 2-8° C. after gentle mixing overnight.

Figure 3:
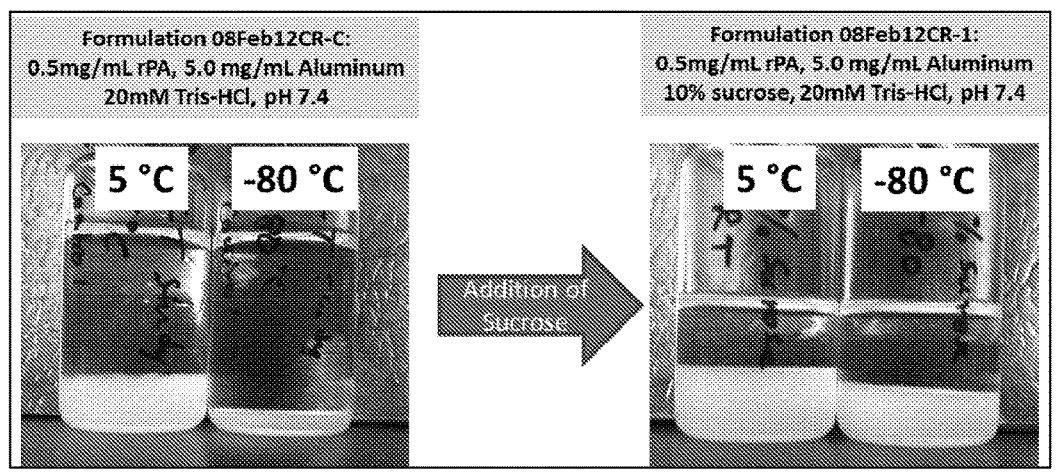
FIG. 3. Photographs of an rPA vaccine with and without sucrose at 2°-8° C. and at −80° C. followed by thawing.

Samples stored at −80° C. overnight were thawed on the lab bench the next day for 2-3 hours before observations were made. FIG. 3 contains a photograph of each formulation from 2-8° C. (labeled 5° C.) and −80° C. after both being brought to room temperature. As shown, gel collapse occurred in both −80° C. samples (rPA Control 2 and rPA Test 2) after thaw as compared to the samples that remained refrigerated at 2-8° C. However, the amount of gel collapse was visibly greater in the rPA Control 2 sample that did not include sucrose.

Example 3: In Vivo Mouse Potency Assay

Lyophilized vaccines were prepared as outlined in Table 4. Dried vaccines were reconstituted with water for injection to a final rPA concentration of 0.15 mg/ml (75 μg/0.5 ml dose) and then diluted in normal saline by 10-fold to yield a dose level of 0.1 (DL).

Female CD-1 mice at 5-8 weeks of age and weighing 20-25 grams each were used for this study. The 0.1 DL of the vaccine was injected (0.5 ml) IP into groups of 20 female CD-1 mice and sera were collected on day 28 for the assessment of their ability to neutralize anthrax LT cytotoxicity in the toxin neutralization assay (TNA) in mice.

TABLE 4

Lyophilized Formulations for Mouse Potency Assay

| Samples | Formulation |
|---|---|
| Lyophilized #1 | 10% trehalose, 0.5 mg/ml rPA, 5.0 mg/ml aluminum, 0.25% sorbitol, 75 mM NaCl, 1% arginine, 20 mM Tris-HCL, pH 7 |
| Lyophilized #2 | No sugar, 0.15 mg/ml rPA, 1.5 mg/ml aluminum, 20 mM Tris-HCl, pH 7.4 |
| Lyophilized #3 | 30% trehalose, 0.15 mg/ml rPA, 1.5 mg/ml aluminum, 2% arginine, 0.025% polysorbate 80, 20 mM Tris-HCl, pH 7.4 |
| Lyophilized #4 | 20% trehalose, 0.15 mg/ml rPA, 1.5 mg/ml aluminum, 10% glycine, 0.025% polysorbate 80, 20 mM Tris-HCl, pH 7.4 |

The immunogenicity of the rPA102 formulation was investigated by calculating Neutralization factor (NF50). The neutralization factor, NF50 is defined as follows:

$$NF50 = \frac{ED50_{sample}}{ED50_{reference}}$$

Where effective dose 50% (ED50) reference standard was prepared by using a qualified serum reference standard stored at or below −20° C.

The geometric mean (GeoMean) of the NF50 of each vaccine formulation was calculated based on 20 NF50 values from 20 mice. T-test or one-way ANOVA were used to compare the geometric mean of NF50 of each formulation at the 95% confidence level. If the p value of the geometric mean NF50 was larger than 0.05, there was no significant difference in NF50 (potency) among the formulations. If the p value was less than 0.05, the geometric mean NF50 of the formulations was significantly different from each other.

Figure 4:
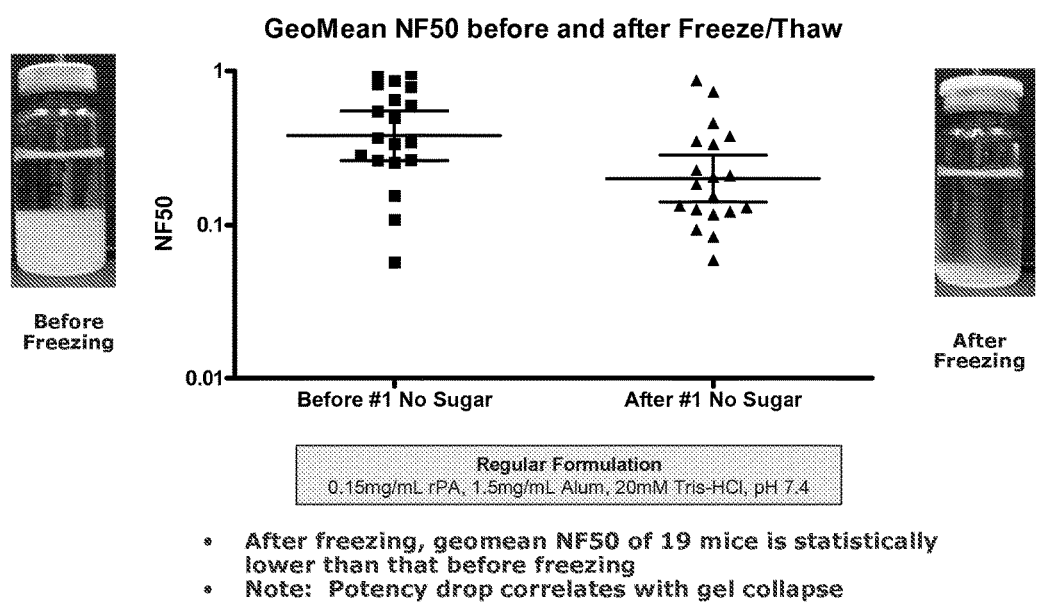
FIG. 4. A graph showing the GeoMean NF50 of a no sugar rPA formulation before and after freezing and photographs showing the collapse of the alum gel.

The control (lyophilized #2) was an rPA102 formulation without stabilizer (0.15 mg/ml rPA, 1.5 mg/ml aluminum, 20 mM Tris-HCL, pH 7.4). The effect of freezing on the GeoMean NF50 values from the relative mouse potency assay for the regular rPA102 formulation is shown in FIG. 4. The control formulation was susceptible to freeze/thaw damage with immunogenicity dropping significantly after the freezing process (FIG. 4). The drop in immunogenicity corresponded to the decrease in the height of the aluminum gel in the solution.

Figure 7:
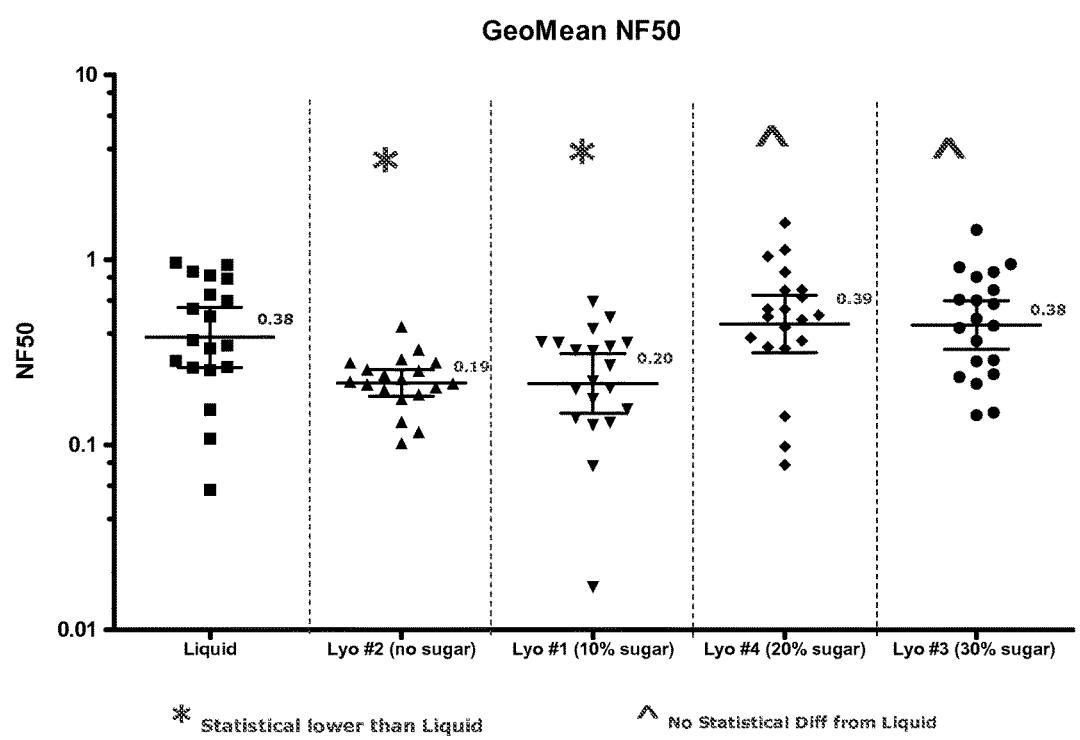
FIG. 7. A graph showing GeoMean NF50 for all lyophilized samples compared to a liquid control.

Lyophilized Samples #1 and 2 showed significantly lower immunogenic potency relative to Lyophilized Samples #3 and 4 (which contained 30% and 20% trehalose, respectively). The effect of sugar in the formulation on lyophilization of rPA102 vaccine was shown by GeoMean NF50 results in FIG. 7. Lyophilized Sample #1 (10% sugar) was not able to protect rPA102 from freeze-dry stress (see FIG. 7). These results showed that 20% and 30% sugar was able to protect rPA102 from lyophilization stress. The appearance of gel collapse correlated with potency loss.

Figure 5:
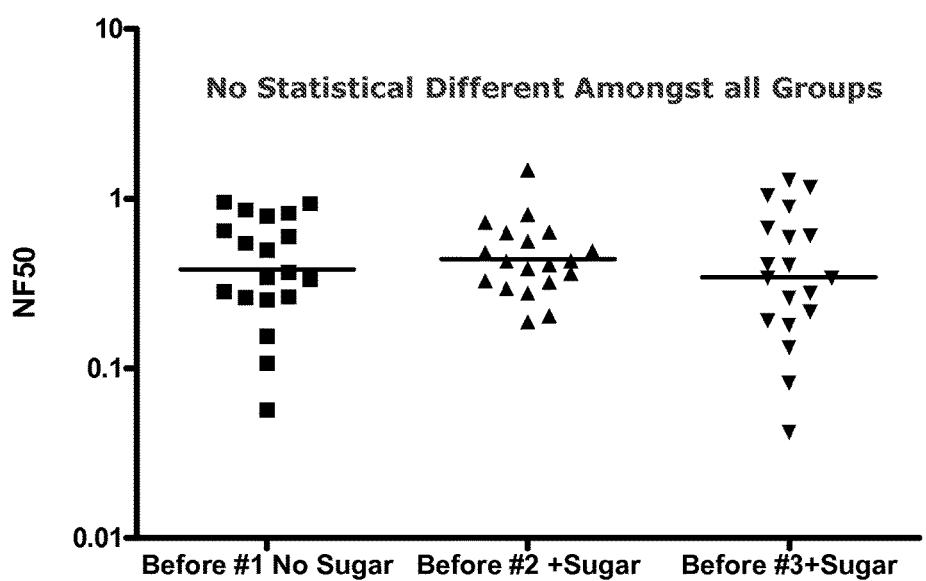
FIG. 5. A graph showing the GeoMean NF50 response of lyophilized samples with and without sugar that were not frozen.
Figure 6:
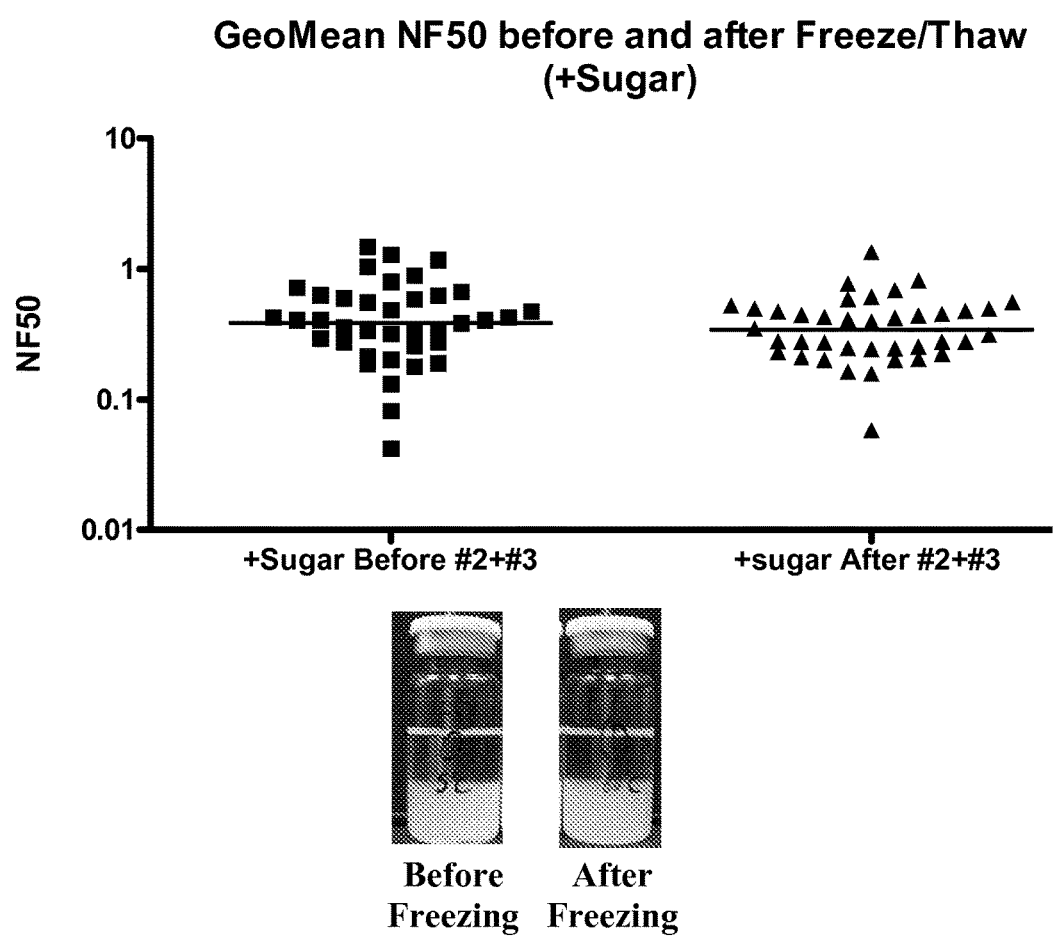
FIG. 6. A graph showing the GeoMean NF50 before and after freeze/thaw for an rPA composition containing 20% trehalose.

NF50 responses were determined from two more formulations that differ only by the absence or presence of trehalose: #1) 0.15 mg/mL rPA, 1.5 mg/mL alum, 2% arginine, 0.025% TWEEN 80 (polysorbate 80), 20 mM Tris-HCL, pH 7.4 and #2 & #3) 0.15 mg/mL rPA, 1.5 mg/mL alum, 20% trehalose, 2% arginine, 0.025% TWEEN 80 (polysorbate 80), 20 mM Tris-HCL, pH 7.4 and the effect of sugar before freezing on the GeoMean values for rPA102 is shown in FIG. 5. In FIG. 5 formulation groups #2 & #3 are just different vials of the same formulation. Adding trehalose had no impact on the immunogenicity of the formulation as demonstrated by no statistical change in NF50 for the two formulations (3 samples), with and without sugar and no freezing (FIG. 5). A comparison of GeoMean values before and after freezing of these trehalose containing formulations is shown in FIG. 6. There was no statistically significant change in immunogenicity (NF50) before and after freezing when this formulation was used (FIG. 6). In addition, there was no collapse of the alum gel (gel height maintained) after freezing with this formulation (photographs in FIG. 6). These results show that the tested formulations with 20% trehalose protected this rPA vaccine from freeze/thaw stress.

Example 4: Rabbit Immunogenicity and Stability Study

The immunogenicity of recombinant protective antigen (rPA) lyophilized vaccine formulations stored at 5 and 50° C. for 4 month was compared to Anthrax Vaccine Adsorbed (AVA) (BIOTHRAX®) using a toxin neutralizing antibody assay (TNA) in New Zealand White (NZW) rabbits. This rabbit immunogenicity study utilized a two immunization schedule (Day 0 and Day 28) and bleeds were taken on days −1 or 0, 14, 21, 28, 35, 42, 56 and 70.

The rPA lyophilized vaccine was prepared using the ingredients shown in Table 5. The ingredients of the final formulation were blended prior to lyophilization and after reconstitution as shown in Table 5. Briefly, 2 mL of the suspension was filled in a 10 mL glass vial. The lyophilization was performed using a VirTis AdVantage lyophilizer. After lyophilization, the vaccines were stored at 5 and 50° C.

TABLE 5

| rPA Formulation | | |
|---|---|---|
| Ingredients | Pre-lyophilization (2 mL suspension in 10 vial) | Post reconstitution by adding 6.11 mL water to final volume of 6.67 mL |
| rPA, mg/mL | 0.5 | 0.15 |
| Aluminum, mg/mL | 5 | 1.50 |
| % Trehalose | 25% | 7.5% |
| Sorbitol | 0.25% | 0.075% |
| TWEEN 80 | 0.03% | 0.0075% |
| Arginine | 1% | 0.30% |
| NaCl, mM | 75 | 22.5 |
| Tris-HCl, mM pH 7.4 | 20 | 6.0 |
| Volume, mL | 2 | 6.67 |

In particular, stock solutions were prepared and (except for TWEEN 80 and NaCl) pH adjusted to 7.4 using 0.1N NaOH and/or 0.1N HCl. After stock solutions were prepared, 150 mL of the following formulation blend was prepared in a 200 mL Nalgene bottle: 0.5 mg/mL rPA, 5.0 mg/mL aluminum, 30% Trehalose (w/v), 0.25% Sorbitol (w/v), 1% Arginine (w/v), 0.025% TWEEN 80, 75 mm NaCl, 20 mM Tris-HCl, pH 7.4, which was used to fill 10 mL vials with 2 mL of formulation blend.

After filling vials, the samples were dried using a VirTis AdVantage lyophilizer with the following program:

| Initial freezing: | | |
|---|---|---|
| Step | Process | Setting |
| Freeze | Freeze (° C.) | −60 |
| | Additional Freeze time (min) | 0 |
| | Condenser (° C.) | −80 |
| | Vacuum (mTorr) | 90 |

| Drying: | | | | |
|---|---|---|---|---|
| Step | Temp ° C. | Time (min) | R/H | Vac mTorr |
| 1 | −60 | 120 | H | 90 |
| 2 | −28 | 60 | R | |
| 3 | −28 | 1250 | H | |
| 4 | −28 | 550 | H | |
| 5 | 25 | 480 | R | |
| 6 | 25 | 600 | H | |
| 7 | 30 | 120 | R | |
| 8 | 30 | 300 | H | |
| 9 | 35 | 120 | R | |
| 10 | 35 | 300 | H | |
| 11 | 40 | 120 | R | |
| 12 | 40 | 300 | H | |
| 13 | 45 | 120 | R | |
| 14 | 45 | 255 | H | |

| Post-drying: | |
|---|---|
| Secondary Dry Set-Point Temperature | +65° C. |
| Post-Heat Settings | |
| Temperature (° C.) | +25 |
| Time (min) | 1250 |
| Vacuum (mTorr) | 1250 |

Vials were stored as described in Table 6. On the day of immunization, 6.11 mL sterile water for injection was added to each vial to reconstitute the lyophilized samples. The vials were mixed end over end until all formulation components were completely dissolved. Dilutions (1:4, 1:16 and 1:64) of each test and control article were prepared in sterile normal saline.

NZW rabbits were used for the present study. NZW rabbits are commonly used as an animal model for *Bacillus anthracis* disease to test for toxicity, immunogenicity and efficacy studies, and NZW rabbits are considered to be a well-characterized model since they have similar pathogenesis and clinical presentation as seen in humans (EK Leffel et al., Clin Vaccine Immunol. 19(18):1158-1164, 2012; AJ Phipps et al., Microbiol Mol Biol Rev. 68(4):617-29, 2004). Each group of NZW rabbit (10 per vaccine group) received a 0.5 mL intramuscular injection with the 1:4, 1:16 & 1:64 dilutions of a lyophilized rPA vaccine formulation or AVA on days 0 and 28. AVA (BIOTHRAX®) is a liquid anthrax vaccine that includes the 83 kDa protective antigen protein and is formulated with 1.2 mg/mL aluminum (added as aluminum hydroxide in 0.85% sodium chloride), 25 mg/mL benzethonium chloride and 100 mg/mL formaldehyde (added as preservatives).

Serum samples were collected at days −1 or 0, 14, 21, 28, 35, 42, 56 and prior to termination on day 70. The TNA assay was performed by using serum collected on day −1 or 0, 14, 35 and 42. Table 6 summarizes the study design.

TABLE 6

Rabbit Immunogenicity Study Design

| Group # | Tested Vaccine | Vaccine Dilution | Immunization Schedule (Study Days) | Dose Volume (mL) | Blood Collection* | # of Animals (Rabbits) |
|---|---|---|---|---|---|---|
| 1 | AVA | 1:4 | Day 0 and 28 | 0.5 mL | Prior to the day of dose initiation (Day −1 or 0) and on Days 14, 21, 28, 35, 42, 56 and 70 | 10 (5M/5F) |
| 2 | (positive | 1:16 | | | | |
| 3 | control) | 1:64 | | | | |
| 10 | rPA | 1:4 | | | | |
| 11 | Lyophilization | 1:16 | | | | |
| 12 | 5° C., 4 months | 1:64 | | | | |
| 13 | rPA | 1:4 | | | | |
| 14 | Lyophilization | 1:16 | | | | |
| 15 | 50° C., 4 months | 1:64 | | | | |

*Serum from Days −1 or 0, 14, 35 and 42 tested

The TNA assay is a functional test that evaluates the amount of antibody needed to inactivate the lethal *B. anthracis* toxin complex of LF and PA (lethal toxin, LT). The ability of test serum samples to neutralize lethal toxin in vitro was compared with that of a standard serum sample by using cytotoxicity as the endpoint of the assay (PR Pittman et al., Vaccine 24(17):3654-60, 2006).

Briefly, J774A.1 cells were cultured in flasks for 48 to 72 h in Dulbecco's modified Eagle media (DMEM) containing 4.5 g/liter d-glucose and supplemented with 10% heat-inactivated bovine serum, 2 mM L-glutamine, 1 mM sodium pyruvate, penicillin (50 U/ml), streptomycin (50 µg/ml), and 0.11 mM sodium bicarbonate. Cells were harvested and seeded in 96-well tissue culture plates at 30,000 cells/well, followed by 16 to 24 hour incubation. Serum samples were prepared in a separate 96-well microtiter plate at 2-fold dilutions for a total of seven dilutions per sample. The serum samples were then incubated with a constant concentration of LT (100 ng/ml PA and 80 ng/ml LF) for 1 hour. Then the serum sample with LT was added to the corresponding wells of the tissue culture plate containing the cells and incubated for four hours, after which 25 µl/well of 5 mg/ml of a tetrazolium salt, 3-(4,5-dimethylthiazolyl-2)-2,5-diphenyltetrazolium bromide (MTT), was added. After a 1-hour incubation, the cells were lysed by using 100 µl/well of acidified isopropanol (50% N, N-Dimethylformamide (with deionized water) and 20% SDS (200 g in 1 liter of 50% dimethylformamide)) with the pH adjusted to 4.7 using HCl. Assay plates were incubated for an additional 16-24 hour, absorbance was measured at 570 and 690 nm in which 690 optical density values were subtracted from 570 values using a calibrated Molecular Devices VersaMax Plate Reader. The ED50, which is the dose that produces a quantal effect in 50% of the population in optical density measurement, was determined using SoftMax Pro software (version 5.4.1, Sunnyvale, Calif.).

ED50 for the mouse reference serum (Lot # MS011211) was used to determine the NF50 values of the test serum samples and the positive control (NF50=ED50 Test/ED50 reference). The mouse reference standard was prepared by immunizing 300 mice with AVA vaccine containing CPG 7909 adjuvant. The serum from the 300 mice was collected, pooled and stored frozen at −80° C. as the reference standard. Tables 7A-C show a comparison of the average kinetic data (NF50) for lyophilized rPA stored at 5° C., lyophilized rPA stored at 50° C., and AVA control stored at 5° C. from serum samples at 14, 35 and 42 days, respectively.

TABLE 7A

Comparison of average kinetic data (NF50) at Day 14

| Sample Storage Dilution | rPA lyo 5° C. 1:4 | rPA lyo 50° C. 1:4 | AVA 5° C. 1:4 | rPA lyo 5° C. 1:16 | rPA lyo 50° C. 1:16 | AVA 5° C. 1:16 | rPA lyo 5° C. 1:64 | rPA lyo 50° C. 1:64 | AVA 5° C. 1:64 |
|---|---|---|---|---|---|---|---|---|---|
| Avg | 0.10 | 0.13 | 0.05 | NRS | NRS | NRS | 0.02 | 0.02 | NRS |
| Stdev | 0.07 | 0.08 | 0.02 | NRS | NRS | NRS | 0.01 | 0.01 | NRS |
| CV % | 0.72 | 61% | 50% | NRS | NRS | NRS | 31% | 26% | NRS |
| GeoMean | 0.07 | 0.11 | 0.04 | NRS | NRS | NRS | 0.02 | 0.02 | NRS |

TABLE 7B

Comparison of average kinetic data (NF50) at Day 35

| Sample Storage Dilution | rPA lyo 5° C. 1:4 | rPA lyo 50° C. 1:4 | AVA 5° C. 1:4 | rPA lyo 5° C. 1:16 | rPA lyo 50° C. 1:16 | AVA 5° C. 1:16 | rPA lyo 5° C. 1:64 | rPA lyo 50° C. 1:64 | AVA 5° C. 1:64 |
|---|---|---|---|---|---|---|---|---|---|
| Avg | 3.69 | 3.25 | 1.80 | 1.86 | 1.28 | 0.79 | 0.26 | 0.14 | 0.06 |
| Stdev | 2.19 | 1.47 | 0.85 | 0.82 | 0.99 | 0.46 | 0.25 | 0.11 | NRS |
| CV % | 59% | 45% | 47% | 44% | 78% | 59% | 96% | 77% | 0% |
| GeoMean | 3.14 | 2.98 | 1.61 | 1.70 | 0.94 | 0.67 | 0.16 | 0.10 | 0.06 |

TABLE 7C

Comparison of average kinetic data (NF50) at Day 42

| Sample Storage Dilution | rPA lyo 5° C. 1:4 | rPA lyo 50° C. 1:4 | AVA 5° C. 1:4 | rPA lyo 5° C. 1:16 | rPA lyo 50° C. 1:16 | AVA 5° C. 1:16 | rPA lyo 5° C. 1:64 | rPA lyo 50° C. 1:64 | AVA 5° C. 1:64 |
|---|---|---|---|---|---|---|---|---|---|
| Avg | 2.54 | 2.35 | 1.15 | 1.21 | 0.78 | 0.46 | 0.17 | 0.12 | 0.05 |
| Stdev | 1.74 | 1.18 | 0.60 | 0.67 | 0.60 | 0.26 | 0.17 | 0.08 | 0.04 |
| CV % | 68% | 50% | 52% | 56% | 77% | 56% | 97% | 64% | 75% |
| GeoMean | 2.07 | 2.13 | 1.01 | 1.08 | 0.57 | 0.40 | 0.11 | 0.10 | 0.04 |

Figure 8A:
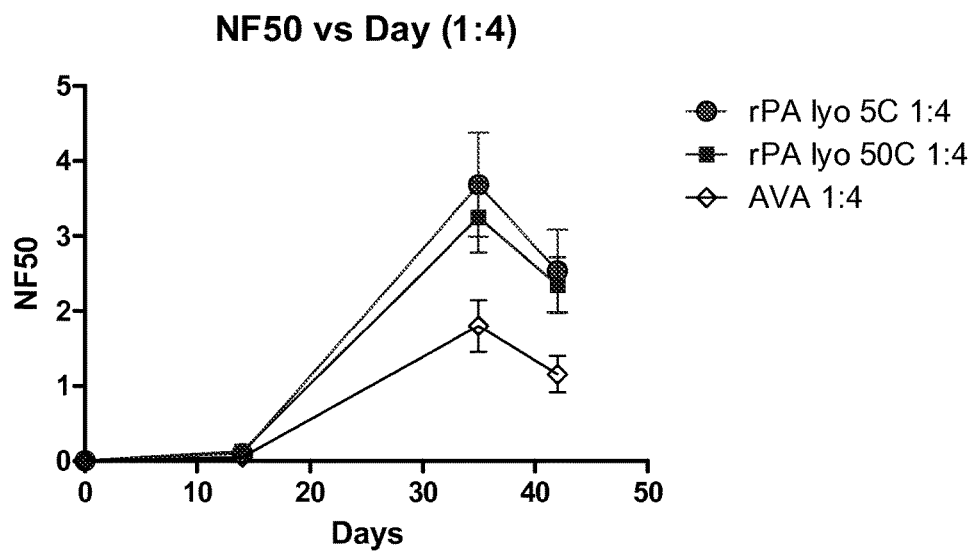
FIGS. 8A-B. A graph showing NF50 over time for lyophilized rPA at (A) 5° C. and 50° C. compared to AVA shown in linear NF50 scale and (B) 5° C. and 50° C. compared to AVA shown in log NF50 scale, each vaccine was at a 1:4 dilution.
Figure 8B:
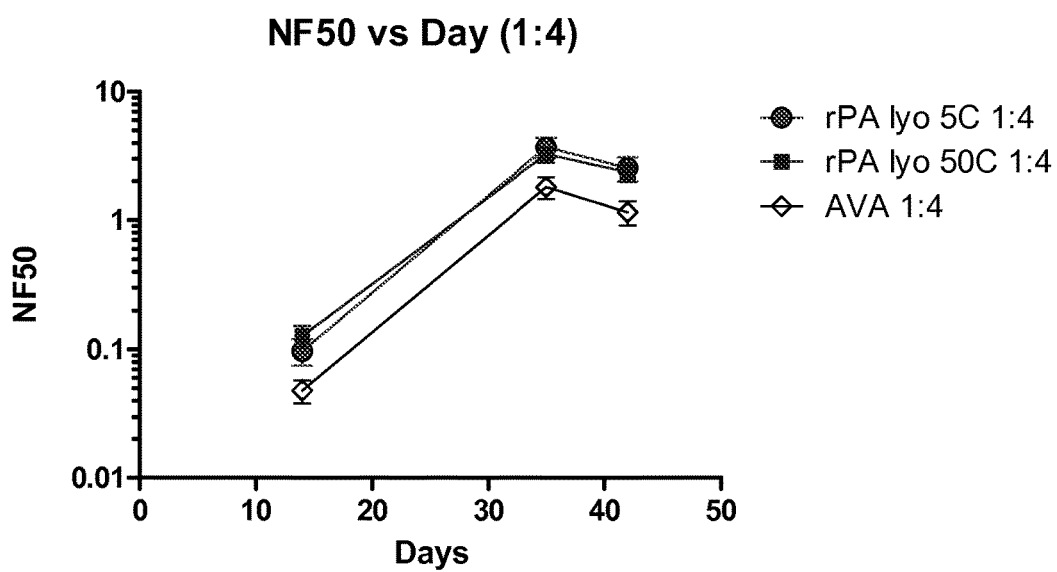
Figure 9A:
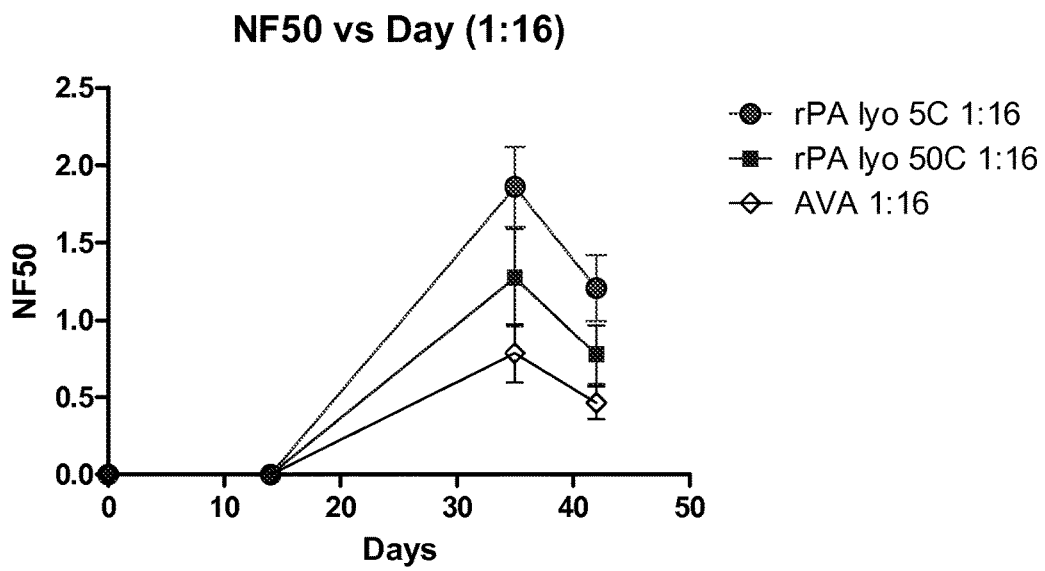
FIGS. 9A-B. A graph showing NF50 over time for lyophilized rPA at (A) 5° C. and 50° C. compared to AVA shown in linear NF50 scale and (B) 5° C. and 50° C. compared to AVA shown in log NF50 scale, each vaccine was at a 1:16 dilution.
Figure 9B:
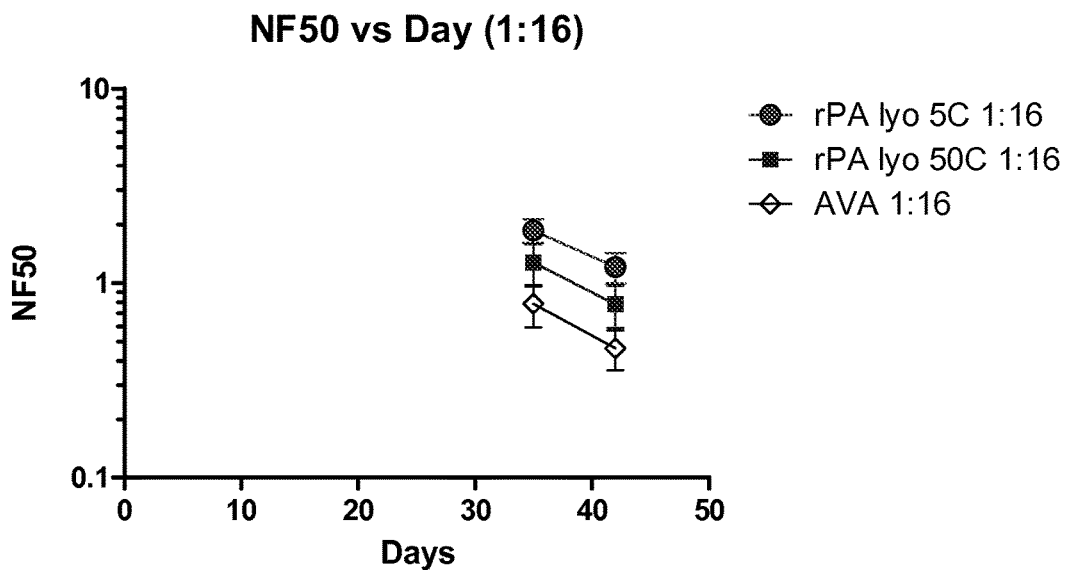
Figure 10A:
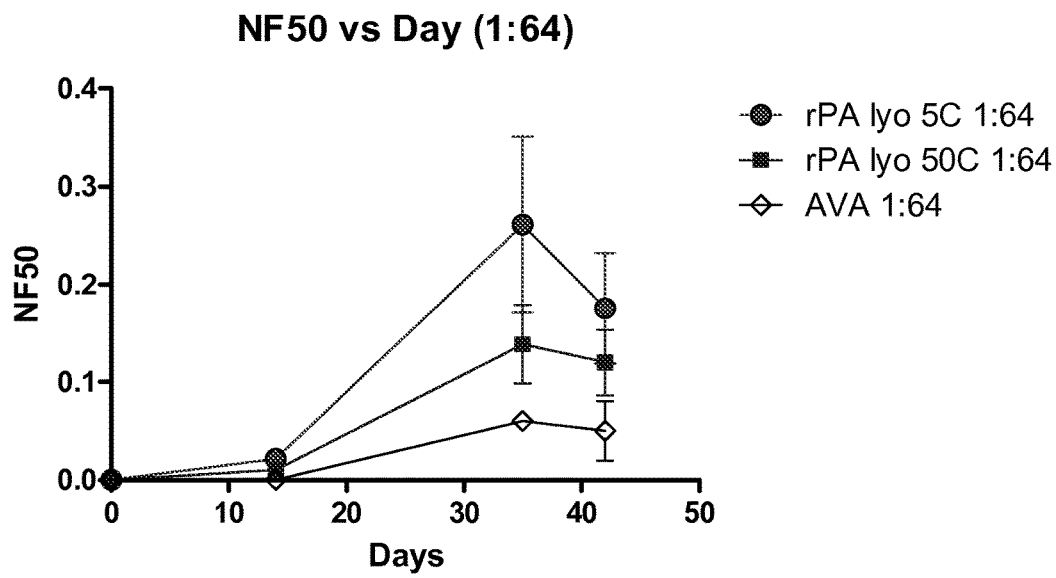
FIGS. 10A-B. A graph showing NF50 over time for lyophilized rPA at (A) 5° C. and 50° C. compared to AVA shown in linear NF50 scale and (B) 5° C. and 50° C. compared to AVA shown in log NF50 scale, each vaccine was at a 1:64 dilution.
Figure 10B:
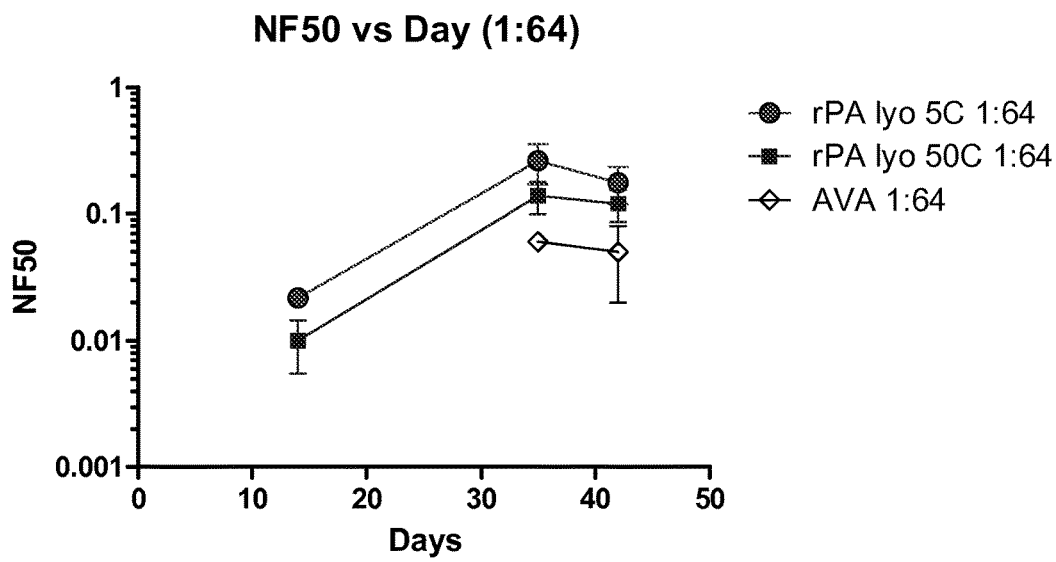
Figure 11A:
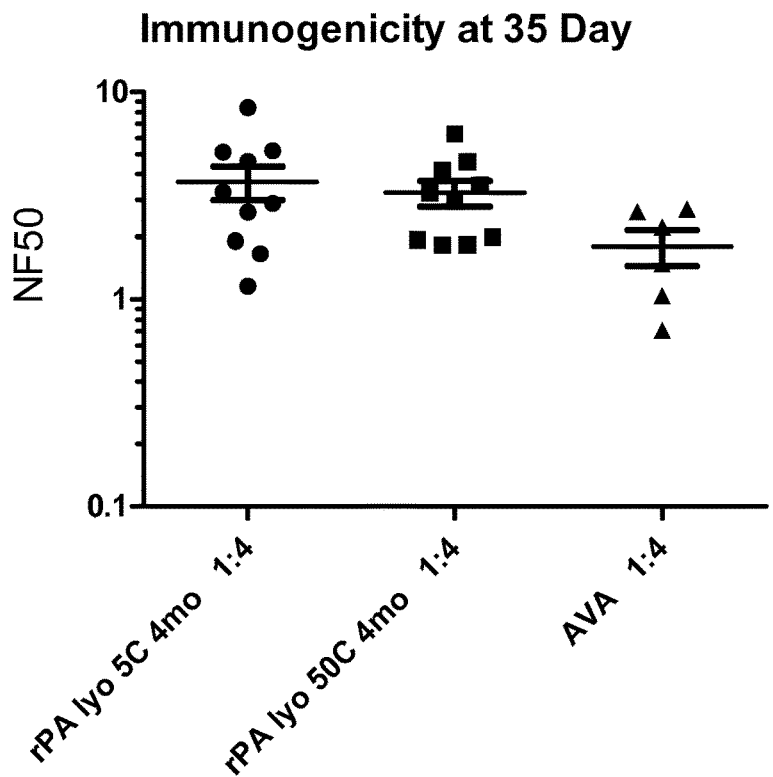
FIGS. 11A-B. A graph showing the comparison of NF50 at (A) day 35 and (B) day 42 for lyophilized rPA at 5° C. and 50° C. and AVA, each vaccine was at a 1:4 dilution.
Figure 11B:
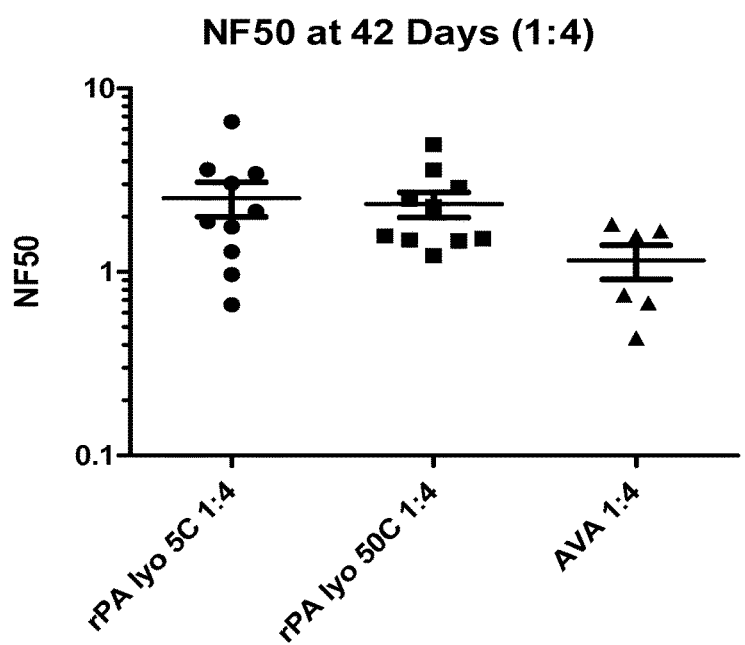
Figure 12A:
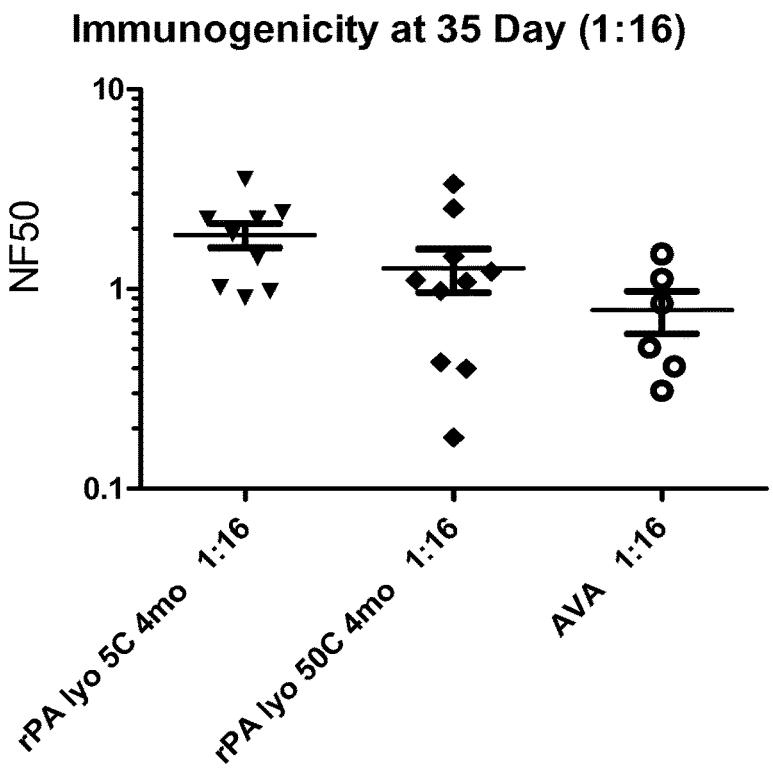
FIGS. 12A-B. A graph showing the comparison of NF50 at (A) day 35 and (B) day 42 for lyophilized rPA at 5° C. and 50° C. and AVA, each vaccine was at a 1:16 dilution.
Figure 12B:
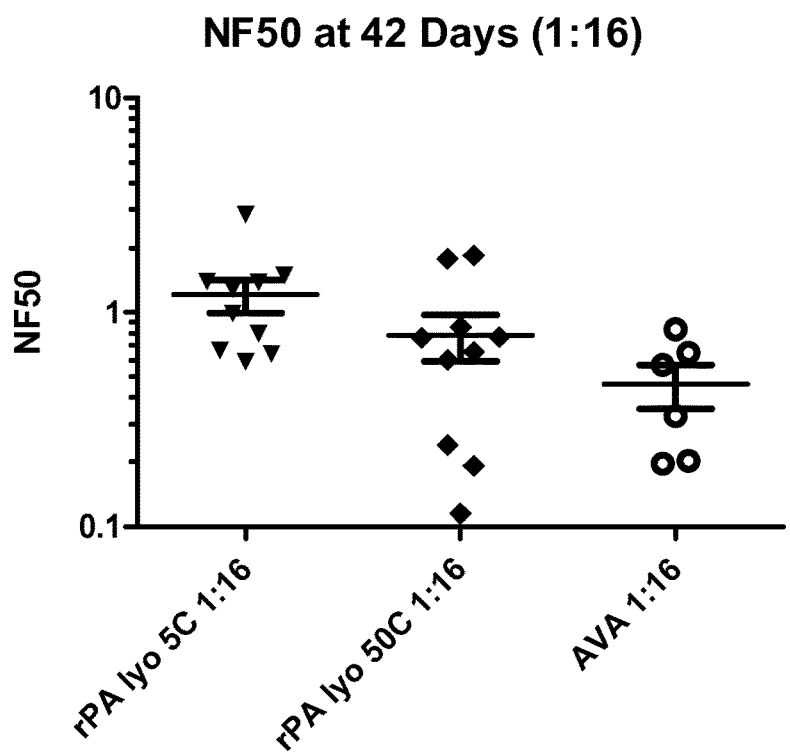
Figure 13A:
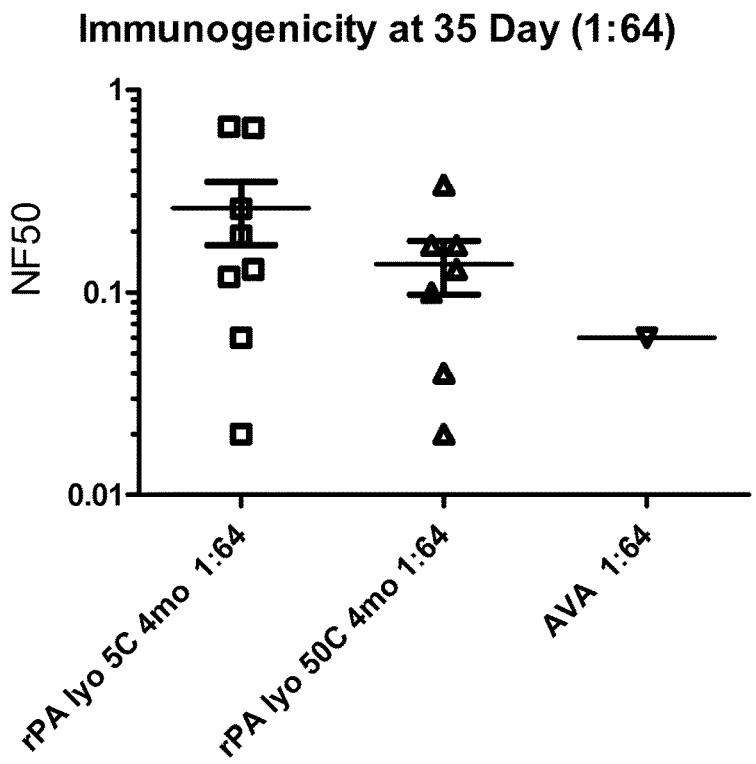
FIGS. 13A-B. A graph showing the comparison of NF50 at day 35 (A) day 35 and (B) day 42 for lyophilized rPA at 5° C. and 50° C. and AVA, each vaccine was at a 1:64 dilution.
Figure 13B:
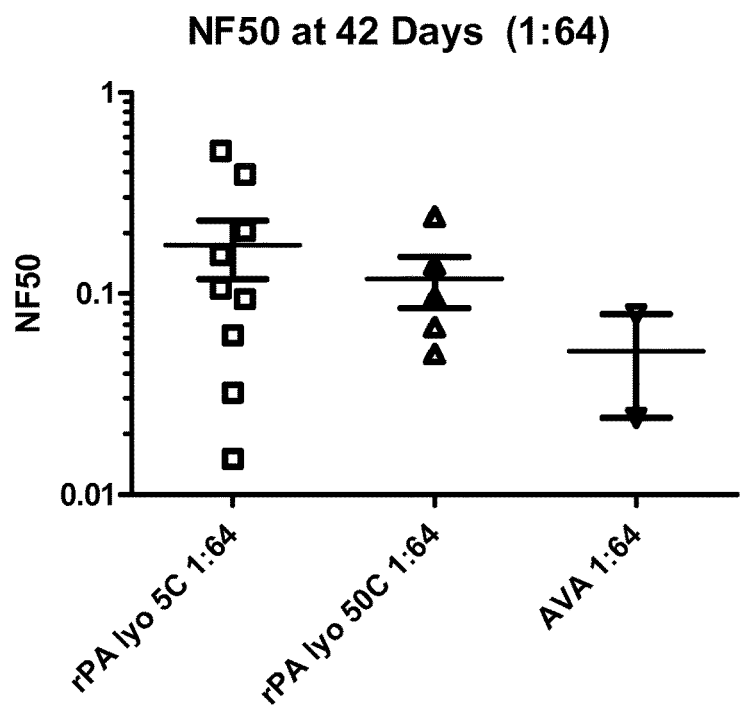

All animals tested negative for toxin neutralizing activity at day 0. <NF50> reached maximum levels at 35 days for all three tested vaccines at all three dose levels (FIGS. 8A-B, 9A-B, and 10A-B), showing that rPA had similar or better immunogenicity kinetic as AVA at all three doses. As shown in FIG. 8A-B, lyophilized rPA (1:4 dilution) stored at both 5 and 50° C. had a higher <NF50> than AVA (1:4 dilution). Similarly, at dilutions of 1:16 and 1:64, the lyophilized rPA had higher <NF50> than the comparable AVA dilution (see FIGS. 9A-B and 10A-B).

For the 1:4 dilutions at 35 days, the <NF50> geomean (gm) for lyophilized rPA stored at 5 and 50° C. was found to be 3.14 and 2.98, respectively; and the <NF50>gm of AVA at 1:4 dilution was 1.61. There was no statistical differences in <NF50>gm between the lyophilized rPA formulations (1:4) stored at 5° C. versus 50° C., p=0.82 (t.test). The <NF50>gm of the combined data (rPA lyo 5 and 50° C.) was found to be 3.06; and the combined <NF50>gm was statistical higher than that of the AVA reference (1.61), p=0.034 (t.test). At day 42 (1:4), there was no statistical different in <NF50>gm between rPA lyo stored at 5 versus 50° C. (2.07 and 2.13, respectively), p=0.92 (t.test); and the combined <NF50>gm was found to be 2.10. The combined <NF50>gm of 2.10 was statistically higher than that of AVA reference (1.01), p=0.028 (t.test).

For the 1:16 dilutions at day 35, the <NF50>gm for lyophilized rPA stored at 5 and 50° C. was found to be 1.70 and 0.94, respectively. There was no statistical differences in <NF50>gm between rPA lyo stored at 5 and 50° C., p=0.081 (t.test). The combined <NF50>gm was found to be 1.27, and there was no statistical difference in combined <NF50>gm for rPA lyo (5 and 50° C.) and that of AVA reference (0.67), p=0.064 (t.test). At day 42 (1:16), there was no statistical different in <NF50>gm between rPA lyo stored at 5 versus 50° C. (1.08 and 0.57, respectively), p=0.071 (t.test); and the combined <NF50>gm was found to be 0.78. The combined <NF50>gm of 0.78 was statistical higher than that of AVA reference (0.40), p=0.05 (t.test).

For the 1:64 dilutions at day 35, the <NF50>gm for lyophilized rPA stored at 5 and 50° C. were not statistically different (1.06 and 0.10, respectively), p=0.386 (t.test). The combined <NF50>gm was found to be 0.13 and the AVA reference was 0.06. At day 42 (1:64), there was no statistical different in <NF50>gm between rPA lyo stored at 5 and 50° C. (0.11 and 0.10, respectively), p=0.91 (t.test); and the combined <NF50>gm was found to be 0.11. There was no statistical difference between the combined <NF50>gm of 0.11 and the AVA reference (0.04), p=0.35 (t.test).

Geometric mean of NF50 (<NF50>gm) of lyophilized rPA stored at 5 and 50° C. compared to AVA at three dilutions (1:4, 1:16, and 1:64) at days 35 and 42 are shown in FIGS. 11A-B, 12A-B, and 13A-B.

At day 35, the <NF50>gm for the lyophilized rPA vaccine stored at 50° C. was found to be 2.98, 0.94 and 0.1 for doses 1:4, 1:16 and 1:64, respectively. The <NF50>gm of the lyophilized rPA vaccine stored at 5° C. were similar at day 35 (3.14, 1.7 and 0.16, respectively) with no statistically significant difference compared to 50° C. (alph=0.05). Similar results were found at day 42. These data demonstrated that the immunogenicity of the lyophilized rPA vaccine stored at 50° C. for 4 months was not significantly different from the lyophilized rPA vaccine stored at 5° C.

At day 35, the combined <NF50>gm (5° C. and 50° C.) was found to be 3.06, 1.27 and 0.1 at doses 1:4, 1:16 and 1:64, respectively; and the p values for the combined <NF50>gm compared to AVA at 1:4 and 1:16 were p=0.034 and p=0.064, respectively. The combined <NF50>gm was found to be non-inferior (statistical higher or no difference) to that of the AVA. Similar results are shown for day 42. At 42 days, the combined <NF50> values for 1:4, 1:16, and 1:64 were 2.10, 0.78, 0.11, respectively; and the p values for the combined <NF50>gm compared to AVA at 1:4, 1:16, and 1:64 were p=0.92, p=0.071, and p=0.91, respectively. These immunogenicity data show that the rPA lyophilized vaccine stored at 5° C. and 50° C. for 4 months was at least as immunogenic as the AVA vaccine.

In sum, these results show that the tested lyophilized formulation was capable of stabilizing the rPA vaccine for at least 4 months at 50° C. The data demonstrated that the rPA lyophilized formulation had superior thermal stability profile compared to AVA vaccine. Thus, the results showed that the rPA lyophilized formulation was effective for rPA anthrax vaccine storage, and the tested formulation was room temperature stable and able to circumvent a cold chain distribution.

Example 5: Guinea Pig Immunogenicity Study

A guinea pig immunogenicity study is outlined in Table 8.

TABLE 8

Guinea Pig Immunogenic

TABLE 8-continued

| Guinea Pig Immunogenicity Study Design | | | | |
|---|---|---|---|---|
| Vaccine | Pre-dilution | Dilution | GP Required (n) 315 to 385 g | Reported Results |
| | | 1/10 | 6 male + 6 female (12) | Survivors/Total |
| | | 1/25 | 6 male + 6 female (12) | Survivors/Total |
| rPA102 | None | 1/1.6 | 6 male + 6 female (12) | Survivors/Total |
| Fresh | | 1/4 | 6 male + 6 female (12) | Survivors/Total |
| | | 1/10 | 6 male + 6 female (12) | Survivors/Total |
| | | 1/25 | 6 male + 6 female (12) | Survivors/Total |
| rPA102 | None | 1/1.6 | 6 male + 6 female (12) | Survivors/Total |
| Liquid | | 1/4 | 6 male + 6 female (12) | Survivors/Total |
| 12-15 months at 5° C. | | 1/10 | 6 male + 6 female (12) | Survivors/Total |
| | | 1/25 | 6 male + 6 female (12) | Survivors/Total |
| rPA102 | None | 1/1.6 | 6 male + 6 female (12) | Survivors/Total |
| Lyophilized | | 1/4 | 6 male + 6 female (12) | Survivors/Total |
| 1 month at 40° C. | | 1/10 | 6 male + 6 female (12) | Survivors/Total |
| (then reconstituted) | | 1/25 | 6 male + 6 female (12) | Survivors/Total |
| | | Challenge Preparation | | |
| Colony Forming Units per 0.1 mL dose | | 40 | 4 male + 4 female (8) | Deaths/Total |
| Total number of vaccinated animals | | | 200 (100 males and 100 females) | |

Example 6: Immunogenicity and Physiochemical Stability in Mice

Three lyophilized rPA vaccine formulations were tested for immunogenicity and physiochemical stability compared to liquid rPA vaccine. The content and purity of rPA vaccines (physiochemical stability properties) were measured by macrophage lysis assay (MLA), size exclusion chromatography (SEC-HPLC), and anion exchange chromatography (AEX-HPLC). The immunogenicity of the rPA vaccines was evaluated by vaccinating CD-1 mice with four dose levels and testing the ability of the mice serum to neutralize anthrax toxin (NF50).

Liquid rPA Vaccine Formulation

Liquid rPA formulation (F1) was prepared under aseptic condition at 0.15 mg/mL rPA, 1.5 mg/mL alum, 2% Alanine, 0.01% TWEEN 80, 25 mM NaPi, pH 7.0. The samples for the stability assays contained 5 mL liquid suspension filled in 10 mL glass vial (10 doses per vial). The intended human dose is 75 µg rPA/750 µg alum per 0.5 mL with intramuscular injection.

Lyophilization rPA Vaccine Formulations

Three lyophilized rPA formulations were prepared. The final formulations, prior to lyophilization, are shown in Table 9. The first lot (lyoA) was formulated with 0.15 mg/mL rPA, 1.5 mg/mL alum, 20% Trehalose, 2% Ala, 0.025% Tw80 and 5 mM NaPi at pH 7.0. The second and third lots (lyoB and lyoC, respectively) contained 3.3× higher rPA and alum concentrations (0.5 mg/mL and 5.0 mg/mL, respectively) with slight variations in sugar, amino acid and buffer as indicated in Table 9.

TABLE 9

| Concentration of Final Formulation Blended Prior to Lyophilization | | | | | | | |
|---|---|---|---|---|---|---|---|
| Lot # | rPA (mg/mL) | Alum (mg/mL) | Sugar | Amino Acid | TWEEN 80 | Buffer | Liq-Lyo Vol, mL |
| LyoA | 0.15 | 1.5 | 20% Trehalose | 2% Alanine | 0.025% | 5 mM NaPi, pH 7.0 | 2 mL fill in 10 mL vials |
| LyoB | 0.5 | 5 | 20% Trehalose | 2% Alanine | 0.025% | 5 mM NaPi, pH 7.0 | 2 mL fill in 10 mL vials |
| LyoC | 0.5 | 5 | 20% Trehalose + 1% Sucrose | 2% Glycine | 0.025% | 20 mM Tris, pH 7.4 | 2 mL fill in 10 mL vials |

All three rPA lyophilized formulations were designed such that most rPA protein was bound to alum with little or no free rPA protein in the solution. 2 mL liquid suspension was filled into a 10 mL glass vial. Lyophilization was performed using FTS LYOSTAR® II with the following processing parameters.

| Initial freezing: | | |
|---|---|---|
| Step | Process | Setting |
| Freeze | Freeze (° C.) | −60 |
| | Additional Freeze time (min) | 0 |
| | Condenser (° C.) | −80 |
| | Vacuum (mTorr) | 90 |

| Drying: | | | | |
|---|---|---|---|---|
| Step | Temp ° C. | Time (min) | R/H | Vac mTorr |
| 1 | −60 | 120 | H | 90 |
| 2 | −28 | 60 | R | |

-continued

| Drying: | | | | |
|---|---|---|---|---|
| Step | Temp ° C. | Time (min) | R/H | Vac mTorr |
| 3 | −28 | 1250 | H | |
| 4 | −28 | 550 | H | |
| 5 | 25 | 480 | R | |
| 6 | 25 | 600 | H | |
| 7 | 30 | 120 | R | |
| 8 | 30 | 300 | H | |
| 9 | 35 | 120 | R | |
| 10 | 35 | 300 | H | |
| 11 | 40 | 120 | R | |
| 12 | 40 | 300 | H | |
| 13 | 45 | 120 | R | |
| 14 | 45 | 255 | H | |

| Post-drying: | |
|---|---|
| Secondary Dry Set-Point Temperature | +65° C. |
| Post-Heat Settings | |
| Temperature (° C.) | +25 |
| Time (min) | 1250 |
| Vacuum (mTorr) | 1250 |

Prior to vaccination and testing, the lyophilized samples were reconstituted with water for injection (WFI) to produce a final concentration of 0.15 mg/mL rPA and 1.5 mg/mL alum for all three formulations. The final concentration was accomplished by adding 1.55, 6.2 and 6.18 mL of WFI to vials of the first lot (LyoA), second lot (LyoB) and third lot (LyoC), respectively. The final suspension volume per vial for LyoA was 2.0 mL and for both lots LyoB and LyoC were 6.7 mL. The concentration of rPA vaccines after reconstitution are shown in Table 10.

The physiochemical properties of the rPA test vaccines were evaluated by a series of assays, i.e., MLA, SEC-HPLC and AEX-HPLC. All of these assays were performed using rPA proteins extracted from the alum. The extraction procedure utilized 200 mM potassium phosphate/0.01% Tw80/0.9% NaCl.

A rPA bulk drug substance (BDS) stored at −80° C. was used as a reference control. The BDS control was purified from a ΔSterne-1(pPA102)CR4 strain of *B. anthracis*, which was developed by the U.S. Army Medical Research Institute of Infectious Diseases (USAMRIID) as an asporogenic, non-toxigenic expression system for the production of rPA. The rPA BDS was purified and stored in 20 mM Tris, 0.9% NaCl, pH 7 under −80° C. frozen condition.

I. Macrophage Lysis Assay (MLA)

The in vitro macrophage lysis assay (MLA) was used to determine the cytotoxicity of rPA on the murine macrophage cell line J7774A.1. The MLA measures the activity of rPA and rLF toxin. The assay involves adding rPA protein to lethal factor protein (rLF) to form a lethal toxin complex, which caused pore formation with the cell membranes of the macrophages, leading to cell lysis.

The activity of the rPA lyophilized vaccines (using rPA desorbed from alum) was measured relative to a BDS reference standard and reported as a percentage of the reference standard. The percentage of cells surviving toxin challenge was determined. For example, 100% MLA activity of rPA vaccine would indicate there was no loss in the cytotoxicity activity of rPA adsorbed to alum and after lyophilized. In brief, microphage cells were seeded in a 96 well plate at $5\times10^4$ cells/well and the plate was placed in a $CO_2$ incubator overnight. The next day, 100 ul of serial diluted rPA test samples or rPA reference standard (starting rPA concentration was 800 ng/ml and then 1:2 diluted down to 0.8 ng/mL) was mixed with rLF (the rLF concentration was constant at 100 ng/ml) and added to the wells. Four hours later, 25 ul of MTT (3-(4,5-Dimethylthiazol-2-yl)-2,5-diphenyltetrazolium bromide) at 5 mg/mL was added to each well and the plate was incubated for 1.5 hours. After the 1.5 hour incubation, 100 ul of soluble solution (20% SDS in 50% dimethylformamide solution) was added to the wells and the plate was incubated at 37° C. overnight. The next day, the plate was read by a plate reader at 570 nm and OD readings were graphed with 4-parameter model using software (SoftMax). The ED50 value of the test sample rPA was then compared to that of the rPA reference standard, and their ratio was used to report relative activity of the rPA test sample. The accuracy of the assay was determined to be +/−30%.

TABLE 10

Concentration of lyophilized rPA vaccine after reconstitution

| Lot # | rPA (mg/mL) | Alum (mg/mL) | Sugar | Amino Acid | TWEEN 80 | NaCl | Buffer | Recons WFI Vol, mL | Final Vol, mL | # Doses/vial (0.5 mL/dose) |
|---|---|---|---|---|---|---|---|---|---|---|
| LyoA | 0.15 | 1.5 | 20% Trehalose | 2% Alanine | 0.025% | — | 5 mM NaPi, pH 7.0 | 1.55 | 2.0 | 4.0 |
| LyoB | 0.15 | 1.5 | 6% Trehalose | 0.6% Alanine | 0.075% | — | 1.5 mM NaPi, pH 7.0 | 6.2 | 6.7 | 13.3 |
| LyoC | 0.15 | 1.5 | 6% Trehalose + 0.3% Sucrose | 0.6% Glycine | 0.075% | — | 6 mM Tris, pH 7.4 | 6.18 | 6.7 | 13.3 |

The total number of doses per vial in lots LyoB and LyoC were higher than that of lot LyoA (13.3 vs 4.0). The manufacturing cost of a higher doses vial (such as 13.3 doses per vial) is significantly lower than that of a lower dose vial (e.g., 4 doses per vial). Thus, it was an economical preference to develop a formulation and process for producing higher dose vials.

Stability & Test Assays

The rPA liquid formulation (F1) was placed in a long term stability program at storage temperatures of 5, 25 and 40° C. The three rPA lyophilized lots (LyoA, LyoB, and LyoC) were placed in a long term stability program at storage temperatures of 5, 25, 40, and 50° C. The physiochemical tests were performed for both the liquid (F1) and lyophilized rPA vaccine formulations. Four (4) months of stability data for the samples were collected.

II. Size-Exclusion Chromatography (SEC-HPLC)

SEC-HPLC is a chromatographic technique used to separate proteins based on their molecular weight and size and it is commonly used to assess the stability of a protein in a formulation. A larger protein typically has a shorter retention time (elute out sooner) in a SEC-column than a smaller protein. Protein that is degraded (or fragmented) will become smaller in size and elute out of the chromatography later. Vice versa, aggregated protein will elute sooner. For example, an aggregated rPA protein that has increased in size would have a shorter retention time than the native rPA protein, and a degraded rPA protein (breakdown in size) would have a longer retention time.

SEC-HPLC is a common assay used to assess the physiochemical stability of a protein in a formulation. Compared to MLA, the SEC-HPLC is, in general, relatively more sensitive and quantitative with precision of less than 5% in % peak area and less than 0.1% in retention time within the same run.

The SEC-HPLC was performed using a TSK G3000SWXL column (Tosoh BioScience P/N M1182-05M) with a mobile phase of 50 mM sodium phosphate/250 mM potassium chloride at pH 7.4. An ultraviolet (UV) detector at 215 nm or fluorescence detector at 280 nm (excitation) and 335 nm (emission) were used for the detection.

III. Anion Exchange Chromatography (AEX-HPLC)

AEX-HPLC separates proteins based on their net electrostatic charge. In general, the assay involved injecting rPA protein solution into an HPLC equipped with an anion exchange column. The rPA protein was retained by the anion exchange (AEX) column (stationary phase) due to electrostatic interaction. The rPA protein was then eluted out by using mobile phase with gradually increased ionic strength (NaCl concentration). The ionic strength (or elution time) at which the rPA molecules eluted is related to its net charges.

The rPA molecule is known to be susceptible to degradation by deamidation mechanism (D'Souza, Journal of Pharmaceutical Sciences, 102(2):454-461, 2013) resulting in a change in net change. Deamidation increases the negative charge of the rPA protein due to the conversion of asparagine residues to aspartate (more negative). The deamidated rPA (typically referred to as the acidic species) elutes in higher ionic strength solution and has a longer elution time than the native rPA protein. The purity of the rPA was characterized by the % main peak.

The AEX-HPLC was performed using Hamilton PRP-X500 Anion Exchange Column (P/N 79641) using mobile phase A of 25 mM Tris at pH 8.0 and mobile phase B of 25 mM Tris, 0.5 M NaCl at pH 8.0. Similar to SEC-HPLC, UV or fluorescence detectors were used.

IV. Immunogenicity Test

Immunogenicity was evaluated using toxin neutralizing assay (TNA) (Hering et al., Biologicals 32 (2004) 17-27; Omland et al., Clinical and Vaccine Immunology (2008) 946-953; and Li et al., Journal of Immunological Methods (2008) 333:89-106. ED50 values for the mouse reference serum (prepared as described above) were used to determine the NF50 values of the test serum sample and the positive control. The first month stability data are reported herein.

For the in vivo immunogenicity test, 20 female CD-1 mice per group received a single 0.5 mL intraperitoneal (i.p.) injection of LyoA, LyoB, LyoC, or liquid rPA (F1). Four dilution dose levels were evaluated (1:4, 1:8, 1:16 and 1:32). The dilutions were prepared on the day of the vaccination with saline solution. Serum samples were obtained by cardiac bleeding at Day 28 after vaccination.

Physiochemical Stability Results

Table 11 summarizes the MLA, SEC-HPLC & AEX-HPLC results of the three lyophilized formulations stored at 4 months at 5, 25, 40 and 50° C. and the BDS reference control.

TABLE 11

Summary of physiochemical stability data at 4 months
4 months physiochemical stability data

| Name | Temp, ° C. | MLA % Relative to Reference | SEC % Purity, Main Peak | AEX % Purity, Main Peak |
|---|---|---|---|---|
| Ref BDS | −80 | 100 | 84.0 | 80.8 |
| lyoA | 5 | 116 | 85.8 | 87.1 |
|  | 25 | 102 | 85.5 | 86.6 |
|  | 40 | 107 | 83.1 | 84.7 |
| lyoB | 5 | 111 | 84.9 | 87.8 |
|  | 25 | 112 | 84.9 | 86.2 |
|  | 50 | 108 | 84.5 | 85.3 |
| lyoC | 5 | 117 | 84.7 | 87.5 |
|  | 25 | 123 | 84.8 | 84.5 |
|  | 50 | 104 | 84.7 | 70.5 |
| Ref BDS | −80 | 100 | 98.6 | 78.2 |
| Lip. rPA F1, 1 month | 5 | 98 | 95.3 | 65.5 |
|  | 25 | 65 | 91.4 | 25.6 |
|  | 40 | 0 | 0 | 0 |

Macrophage Lysis Assay Results

These MLA results show that there was no significant drop in rPA cytotoxicity for the three lyophilization formulations stored at 4 months at temperatures up to 40 and 50° C. when compared to the BDS reference control (within error variability of +/−30%).

Figure 14:
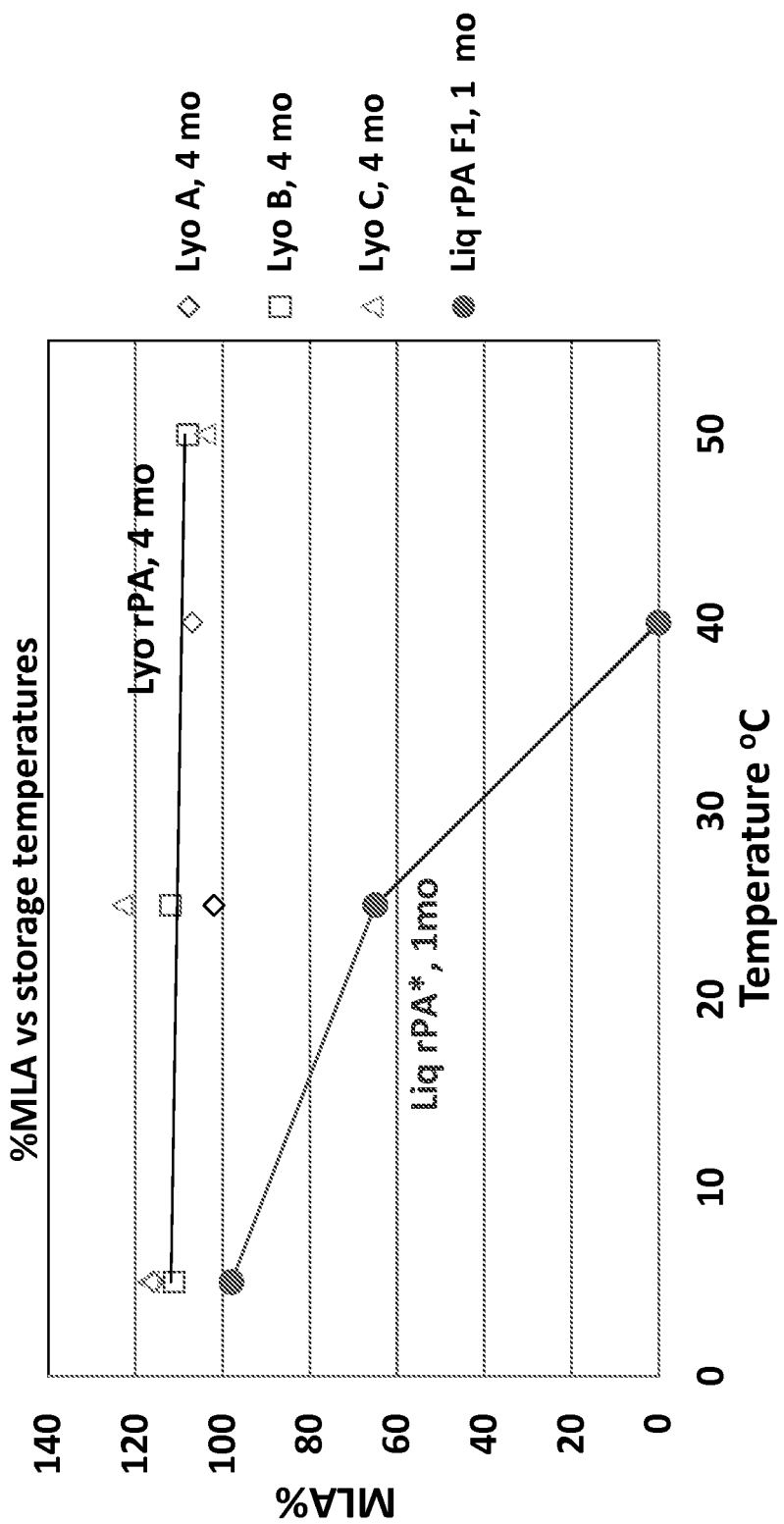
FIG. 14. A graph showing a comparison of the % MLA (microphage lysis assay) value for rPA liquid vaccine (Liq rPA F1) stored at one month versus lyophilized vaccines (LyoA, LyoB, and LyoC) stored at four months as a function of temperature.

In comparison, there is a significant drop in MLA value for the liquid rPA vaccine (F1) stored for one month at 5, 25 and 40° C. The MLA values were found to be 98%, 65% and 0% at 5, 25 and 40° C., respectively. FIG. 14 shows a comparison of the MLA % as a function of storage temperature for the three lyophilized lots stored for 4 months versus the rPA liquid lot (F1) stored for 1 month. These results show that the three lyophilized formulations maintained the MLA activity of the rPA vaccine for at least up to 4 months at 40 and 50° C., whereas the liquid rPA vaccine loss all it MLA activity after storage for 1 month at 40° C.

Size-Exclusion Chromatography (SEC-HPLC) Results

Figure 15A:
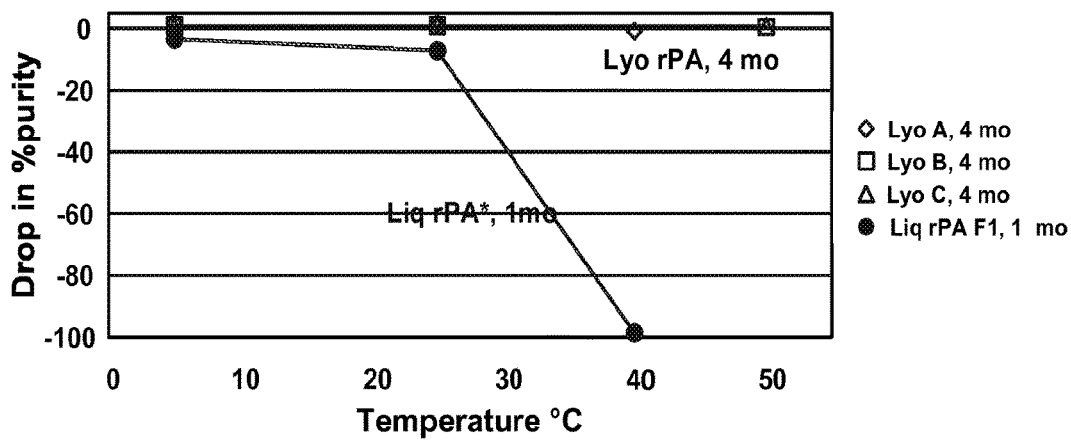
FIGS. 15A-B. (A) A graph showing the relative drop in SEC % purity over reference control as a function of storage temperature of three rPA lyophilized formulations (LyoA, LyoB, and LyoC) stored for four months compared to liquid rPA stored for one month. (B) Shows a typical size exclusion chromatography (SEC-HPLC) chromatograph of rPA BDS reference standard.
Figure 15B:
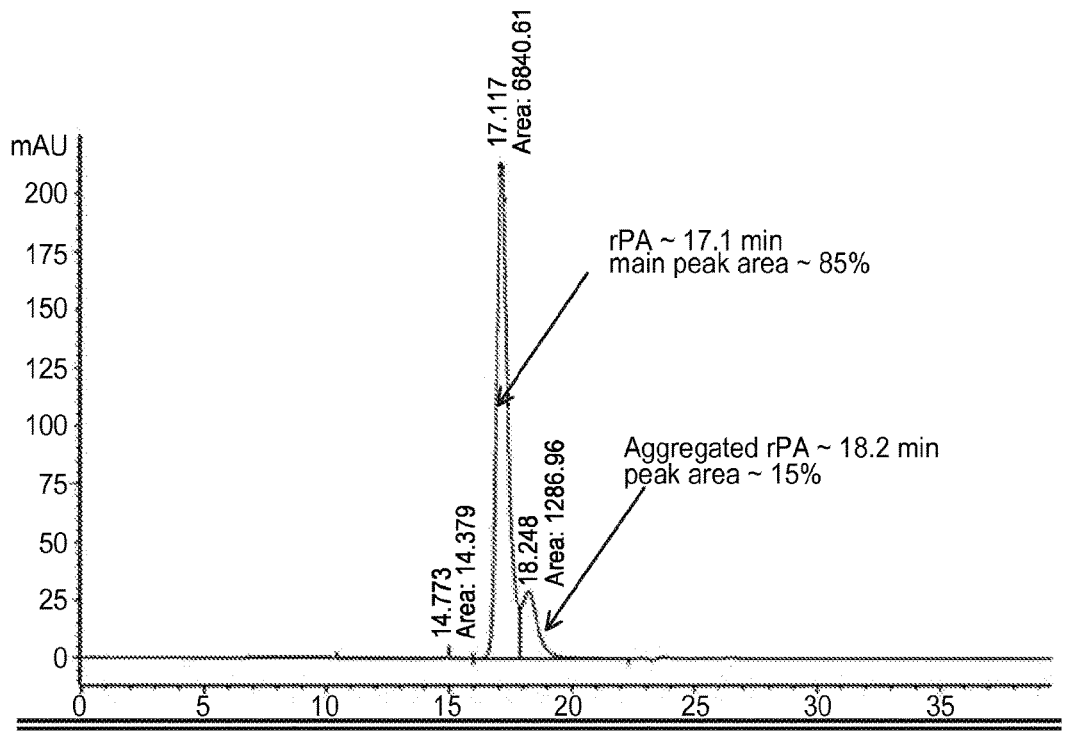

A typical SEC chromatograph of the rPA reference control (BDS) is shown in FIG. 15B. The percent peak area was calculated for each sample peak. The native rPA protein (monomer) eluted at 17.1 minutes with a % main peak area of 85%. The second peak eluted at 18.2 minutes and corresponds to the aggregated rPA molecule main peak area of ~15%. The % purity of rPA protein was determined by the % area of the 17.1 minutes elution peak. i.e., the purity of the rPA protein (% purity rPA)=the percent peak area of the rPA peak (corresponding to monomer rPA with retention time of ~17.1 min)/the total peak area).

The purity results for the LyoA, LyoB and LyoC were comparable to the purity results for the rPA reference BDS of 84.0% stored at −80° C., see Table 11. The SEC-HPLC data showed that there was no significant drop in purity compared to the reference control for all three lyophilized formulations stored at 4 months at all storage temperatures.

As a comparison, there was a significant drop in purity for the liquid rPA vaccine when stored at an accelerated temperature (25, 40, or 50° C.) for 1 month. The relative % purity of rPA of the liquid formulation dropped −3.3%, −7.2% and −98.6% at 5, 25 and 40° C., respectively.

The % purity of the BDS reference control were found to be 84.0% and 98.6% for the lyophilized and the liquid assays, respectively. The two tests were performed at different times. The difference in % purity of the reference control was not unusual. The difference could be due to varying SEC-column condition and sample preparation procedure. The relative % purity (over reference control) is typically used to compare the stability samples at different times and across different laboratories.

FIG. 15A shows the relative decrease of rPA SEC % purity (over BDS reference control) as a function of storage temperature for the three lyophilized formulation compared to the liquid formulation. The data demonstrated there was no change in SEC-purity for the lyophilized rPA vaccine stored for at least 4 months at 40 or 50° C., whereas the liquid rPA vaccine was completely degraded after 1 month storage at 40° C.

Anion Exchange Chromatography (AEX-HPLC) Results

Figure 16A:
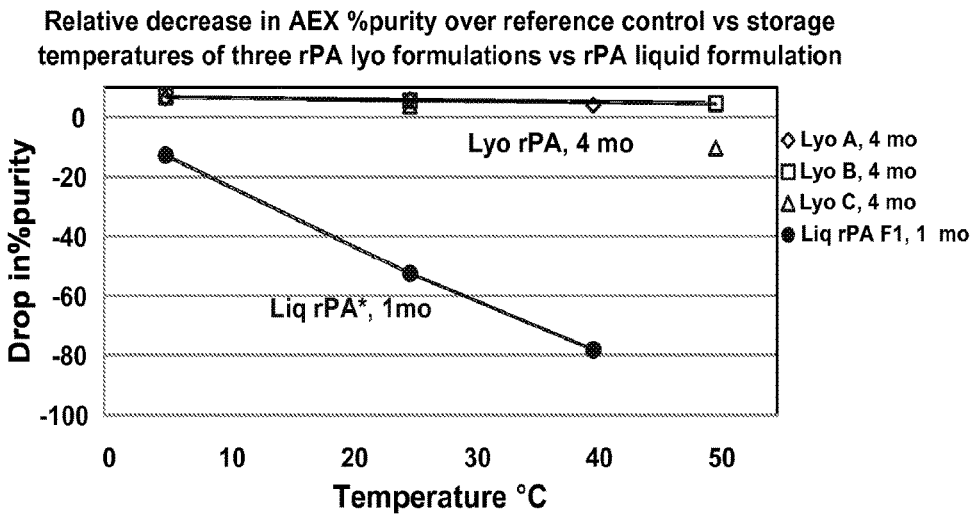
FIGS. 16A-B. (A) A graph showing the relative drop in % AEX purity as a function of storage temperature of three rPA lyophilized formulations (LyoA, LyoB, and LyoC) stored for four months compared to liquid rPA stored for one month. (B) Shows an anion exchange chromatography (AEX-HPLC) chromatographs of rPA BDS reference standard.
Figure 16B:
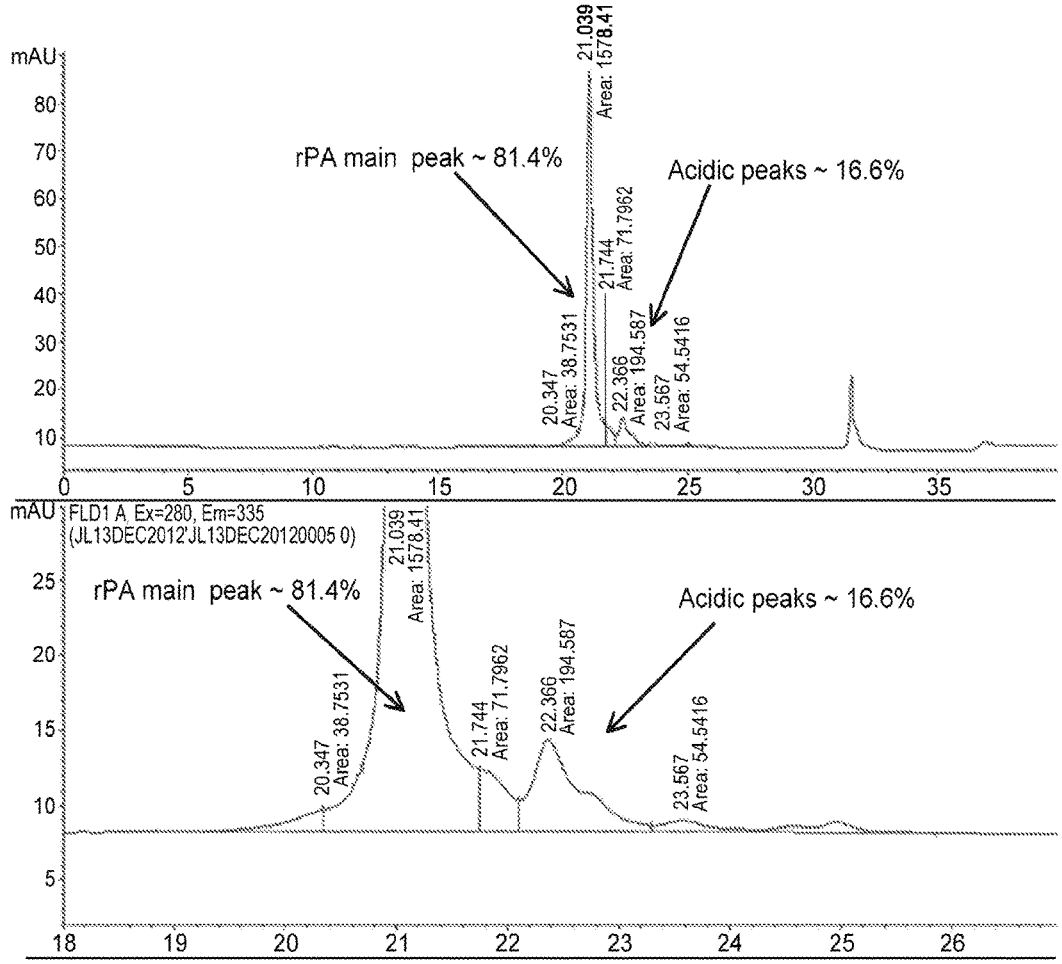

A typical AEX chromatograph for the rPA reference control (BDS) is shown in FIG. 16B. The purity of rPA was characterized by the % main peak area. The native rPA protein eluted at 21.0 minutes with a main peak of ~81.4%. The deamidated rPA (typically referred to acidic species) eluted between 21.7 and 22.4 minutes with an area of 16.6%. The % main peak area was calculated by first integrating the area under the curve of all peaks (except the buffer peak) and then the % main peak area corresponds to the rPA peak with retention time of 21.0 min, (i.e., % main peak area=peak area (RT=21.0 min)/Sum of all peak areas). Similar to SEC-HPLC, the purity of rPA was the same as % main peak area. The accuracy of the AEX assay was about 10-15%.

The AEX % purity of the first lyophilized lot (lyoA) stored for 4 months was found to be 87.1, 86.6, 84.7 at 5, 25 and 40° C., respectively. The AEX purity for the second lyophilized lot (lyoB) was 87.8%, 86.2% and 85.3% at 5, 25 and 50° C., respectively. The AEX % purity for the third lyophilized lot (lyoC) was 87.5%, 84.5% and 70.5% at 5, 25 and 50° C., respectively. These purity results for LyoA, LyoB, and LyoC were comparable to the purity of the rPA reference control (BDS) of 80.8%. There is no significant drop in purities over the reference control for all three lyophilized formulations after 4 months storage at all storage temperatures.

The AEX purity of the liquid rPA vaccine stored at 1 month was found to be 65.5%, 25.6% and 0% at 5, 25 and 40° C., respectively; and the AEX purity for rPA reference control (BDS) was 78.2% when used in the assay testing liquid rPA. The AEX purity results are summarized in Table 11.

As shown in FIG. 16A, there was a significant drop in the AEX-purity in the rPA liquid formulation (F1) at 5, 25 & 40° C. compared to the lyophilized formulations. The AEX-data demonstrated that there was no loss in purity of the lyophilized rPA vaccine stored for at least 4 months at 40 or 50° C.; whereas, the liquid vaccine was completely degraded at 1 month after storage at 40° C.

In Vivo Immunogenicity Results

The NF50 results in mice at dose levels 0.25, 0.125, 0.0625 and 0.03125 for the three lyophilized formulations stored for 1 month each were determined. FIGS. 17A-D, 18A-D, and 19A-D compares the NF50 data (n=20) across various temperatures (5, 25 and 40° C.) at their corresponding formulation and dose level.

The geometric mean of the NF50 (<NF50>gm) at 5, 25 and 40° C. for the four doses level of the three lyophilization formulations are summarized in Tables 12A-C.

TABLES 12A-C

GeoMean of NF50 (n = 20) for the three lyophilized formulations at 5, 25 & 40° C. at four dose levels (0.25, 0.125, 0.0625 & 0.03125)

| Dose Level | 5° C. | 25° C. | 40° C. | Are the <NF> gm significantly different among temperatures? (p < 0.050) ANOVA Test |
|---|---|---|---|---|
| 13A. <NF50> gm of Lyo A stored at 5, 25 and 40° C. at one month at four dose levels | | | | |
| 0.25 | 1.12 | 1.20 | 1.13 | No, p = 0.97 |
| 0.125 | 0.84 | 0.86 | 0.50 | No, p = 0.10 |
| 0.0625 | 0.33 | 0.28 | 0.39 | No, p = 0.36 |
| 0.03125 | 0.10 | 0.15 | 0.13 | No, p = 0.18 |
| 13B. <NF50> gm of Lyo B stored at 5, 25, 40 and 50° C. at one month at four dose levels | | | | |
| 0.25 | 1.16 | 0.81 | 0.86 | No, p = 0.22 |
| 0.125 | 0.33 | 0.46 | 0.32 | No, p = 0.20 |
| 0.0625 | 0.12 | 0.15 | 0.13 | No, p = 0.59 |
| 0.03125 | 0.05 | 0.06 | 0.05 | No, p = 0.78 |
| 13C. <NF50> gm of 31 Lyo C stored at 5, 25, 40 and 50° C. at one month at four dose levels | | | | |
| 0.25 | 0.98 | 0.80 | 1.02 | No, p = 0.37 |
| 0.125 | 0.43 | 0.45 | 0.46 | No, p = 0.94 |
| 0.0625 | 0.13 | 0.15 | 0.20 | No, p = 0.21 |
| 0.03125 | 0.07 | 0.06 | 0.07 | No, p = 0.78 |

For lot LyoA after storage for 1 month, the <NF50>gm were found to be 1.12, 1.20, and 1.13 at 5, 25 and 40° C. respectively at dose level 0.25. There was no statistically significant difference in the <NF50>gm among the three storage temperatures (5, 25 and 40° C.) at p=0.97. Similarly, it was also shown that there was no statistical difference in <NF50>gm among the various storage temperatures at the other tested dose levels (0.125, 0.0625 and 0.01315) for all three lyophilized formulations (LyoA, LyoB, and LyoC). The NF50 data demonstrated that there was no significant drop in immunogenicity for the three lyophilized formulations at 1 month up to 40° C.

In contrast, the liquid rPA formulation (F1) showed a significant drop in immunogenicity at the 25 and 40° C. storage temperatures at 1 month. Table 13 shows the <NF50>gm results for the rPA liquid formulation stored at 1 month at 5, 25 and 40° C.

TABLE 13

Geomean of NF50 of liquid rPA formulation F1 stored at 1 month at 5, 25 & 40° C. at four dose levels (0.3, 0.2, 0.1 & 0.05) <NF50> gm of Liquid rPA (F1) formulation stored at 5, 25 and 40° C. at one month at four dose levels

| Dose Level | 5° C. | 25° C. | 40° C. | Are the <NF> gm significantly different among temperatures? (p < 0.050) ANOVA Test |
|---|---|---|---|---|
| 0.3 | 1.26 | 0.69 | 0.30 | Yes, p = 0.0023 |
| 0.2 | 1.18 | 0.55 | 0.13 | Yes, p = <0.0001 |
| 0.1 | 1.03 | 0.22 | 0.09 | Yes, p = <0.0001 |
| 0.05 | 0.32 | 0.15 | 0.03 | Yes, p = 0.0010 |

At the 0.3 dose level, the <NF50>gm was found to be 1.26, 0.69 and 0.30 at 5, 25 and 40° C., respectively, and there was a statistically significant difference in all the <NF50>gm at p=0.0023. Similarly, at the lower dose levels of 0.2, 0.1 and 0.05, the <NF50>gm significantly dropped as the storage temperature increases (see FIG. 20A-D). The NF50 was found to decease significantly when the liquid vaccine was stored at 25° C. as compare to 5° C. at all four dose levels, and progressively more at 40° C.

In sum, the immunogenicity data demonstrated the superiority of the lyophilized rPA formulations over the liquid rPA formulation. The lyophilized formulations maintain their immunogenicity at 25 and 40° C. for at least 1 month, while the immunogenicity of the liquid formulation decreases significantly over similar storage conditions.

Like most liquid vaccines, liquid rPA vaccines were found to be unstable at accelerated storage temperatures (e.g., 25 and 40° C.). Liquid rPA vaccine lost its immunogenicity and key physiochemical properties when stored at 40° C. for 1 month. Similarly, the key physiochemical properties of the vaccine were also significantly degraded. The content and purity of vaccine as measured by macrophage lysis assay (MLA), size exclusion chromatography (SEC-HPLC) and anion exchange chromatography (AEX-HPLC) were found to significantly decrease at 25° C. and be undetectable at 40° C. for 1 month. Liquid rPA vaccine was known to be susceptible to deamidation reaction especially when it was adsorbed on aluminum and stored at accelerated temperature.

Three lyophilized formulations were manufactured as lot number: lyoA, lyoB and lyoC. These three new rPA lyophilization formulations had superior stability profile over the rPA liquid vaccines. There was no statistically significant change in purity in all key physiochemical assays (MLA, SEC-HPLC and AEX-HPLC) for all three lots of lyophilized formulations when stored at 4 month for temperatures up to 50° C. In addition, there is no significant drop in immunogenicity (NF50) when the lyophilized vaccines were stored at 1 month for up to 40° C. at four dose levels.

The results herein show that the lyophilized rPA formulations had superior physiochemical and immunological stability profiles over the liquid rPA formulation. The lyophilized formulations maintained all the key physiochemical properties tested by MLA, SEC and AEX at storage temperatures up to 50° C. and over the 4 month storage time period. The lyophilized formulations also maintained immunogenicity at storage temperatures up to 40° C. for at least 1 month. On the contrary, the liquid rPA formulation showed a complete loss of the physiochemical properties (MLA, SEC, and AEX) and a significant drop in immunogenicity after storage for 1 month at 40° C.

Example 7: Formulations and Lyophilization with Other Adjuvants

CPG 7909 Bulk Drug Substance (BDS) is packaged as a lyophilized powder in high density polyethylene (HDPE) bottles, heat sealed in multi-layer (mylar, foil) pouches, and stored at −20° C.±5° C.

Glucopyranosyl Lipid Adjuvant (GLA) was obtained from Avanti Polar Lipids, Inc. It was packaged in 2 mL amber glass vials containing 25 mg of lyophilized GLA powder and stored at −20° C.±5° C. GLA is described in Arias et al. (2012) PLoS ONE 7(7):e41144.

Bulk Drug Substance (BDS): 2.81 mg/mL rPA, 0.9% NaCl and buffered in 20 mM Tris-HCl at pH 7.4 was used. It was stored at −80° C. and thawed at 5° C. overnight prior to use.

PolyI PolyC (PIPC) was obtained from InviviGen in 20 mL glass vials as a lyophilized cake containing 50 mg of PIPC. It was stored at 5° C.

TABLE 14

Chemicals and Source

| Chemical Name | Source |
|---|---|
| Tris Hydrochloride, Ultrapure | Amresco |
| 2% ALHYDROGEL (10 mg/mL aluminum) | Brenntag |
| α,α-Trehalose dihydrate | Hayashibara Biochemicals |
| Sodium phosphate, monobasic, Anhydrous | Sigma Aldrich |
| Sodium phosphate, dibasic, hepta-hydrate | BDH |
| Polysorbate 80, N.F. | J. T. Baker |
| L-Alanine | EMD |

TABLE 15

Equipment/Materials

| Name | Source |
|---|---|
| VirTis AdVantage Plus Lyophilizer | SP Scientific |
| Wheaton Serum Vials, Borosilicated Glass | VWR |
| Slotted Rubber Stoppers for Lyo Vials | VWR |
| Flip-Off Crimp Seals | VWR |

Stock Solution Preparations

Two 60% (w/v) solutions of trehalose were prepared in 20 mM Tris and 5 mM NaPi buffers, separately, and were sterile filtered. A 10% (v/v) solution of Polysorbate80 was prepared in DI water and then sterile filtered. Two 12% (w/v) solutions of alanine were prepared in 20 mM Tris and 5 mM NaPi buffers, separately, and were sterile filtered.

One aluminum hydroxide stock solution was buffered by adding 7 mL of 1M Tris buffer, pH 7.4, to 343 mL of 2% AlOH (or 10 mg/mL aluminum) and was titrated to pH 7.4. A second aluminum hydroxide stock solution was buffered by adding 1.75 mL of 1M NaPi buffer, pH 7.0, to 348.25 mL of 2% AlOH and was titrated to pH 7.0. The dilution effect from the buffer addition and subsequent titration was not accounted for in either preparation.

Adjuvant Preparations

GLA adjuvant was prepared in 20 mM Tris-HCl buffer, pH 7.4 by adding 31.2 mg of powder into a 50 mL conical tube and adding 15.6 mL of buffer. The mixture was sonicated for a total of 60 seconds in 10 second intervals with 10 second rests in between to a maximum power of 15 W. A turbid mixture was obtained of 2 mg/mL GLA.

CPG 7909 stocks were prepared in 20 mM Tris, pH 7.4 or 5 mM NaPi, pH 7.0 buffers. In each preparation, about 200 mg of CPG 7909 powder were fully dissolved in a final volume of 10 mL. A clear solution was obtained for both preparations.

A 2 mg/mL stock solution of PIPC was prepared by dissolving a 50 mg lyophilized cake of PIPC in 25 mL of 5 mM NaPi buffer, pH 7.0. The mixture was sonicated for a total of 60 seconds in 10 second intervals with 10 second rests in between to a maximum power of 15 W. A clear solution with no visible particles was obtained.

Formulation Procedure for Blending

Table 16 shows the chemical composition of the prepared formulations:

TABLE 16

Formulation Blends for Liquid and Lyophilization

Chemical Composition

| Sample nos. | Study Group | rPA (mg/mL) | Alum (mg/mL) | Trehalos (%) | Tween 80 (%) | Adjuvant (mg/mL) | Alanine (%) | Tris-HCl Buffer (mM) | NaPi Buffer (mM) | Adjuvant pH Name | NaCl (residual) (mM) |
|---|---|---|---|---|---|---|---|---|---|---|---|
| 7-13 | CPG-Liq | 0.15 | 1.5 | 0 | 0.03 | 0.50 | 0 | 20 | 0 | 7.4 CPG | 8 |
| 14-20 | CPG-Lyo | 0.15 | 1.5 | 20 | 0.03 | 0.50 | 2 | 20 | 0 | 7.4 CPG | 8 |
| 34-39 | GLA-Liq | 0.15 | 1.5 | 0 | 0.03 | 0.50 | 0 | 20 | 0 | 7.4 GLA | 8 |
| 40-45 | GLA-Lyo | 0.15 | 1.5 | 20 | 0.03 | 0.50 | 2 | 20 | 0 | 7.4 GLA | 8 |
| 73-75 | PIPC/CPG-Liq | 0.15 | 1.5 | 0 | 0.03 | 0.50 | 0 | 1.1 | 5 | 7.0 PIPC + CPG | 8 |
| 76-81 | PIPC/CPG-LYO | 0.15 | 1.5 | 20 | 0.03 | 0.50 | 2 | 1.1 | 5 | 7.0 PIPC + CPG | 8 |

The formulation blends in Table 16 were prepared using buffered stock solutions as shown in Table 17.

TABLE 17

Stock/Excipient Volumes Used for Formulation Blend Preparations

Formulation Volumes Added (mL) Stock Solution

| Study Group | rPA Stock (mg/mL) 2.8 | AlOH Stock (mg/mL) 10 | Trehalose Stock (%) 60 | Tween 80 Stock (%) 10 | Alanine Stock (%) 12 | CpG Stock (mg/mL) 20 | GLA Stock (mg/mL) 2 | Poly(IC) Stock (mg/mL) 2 | NaPi Buffer (mM) 5 | Tris Buffer (mM) 20 | Final Volume (mL) |
|---|---|---|---|---|---|---|---|---|---|---|---|
| CPG-Liq | 0.86 | 2.40 | 0 | 0.040 | 0 | 0.40 | 0 | 0 | 0 | 12.30 | 16 |
| CPG-Lyo | 1.07 | 3.00 | 6.67 | 0.050 | 3.333 | 0.50 | 0 | 0 | 0 | 5.38 | 20 |
| GLA-Liq | 0.86 | 2.40 | 0 | 0.040 | 0 | 0 | 4.0 | 0 | 0 | 8.70 | 16 |
| GLA-Lyo | 1.07 | 3.00 | 6.67 | 0.050 | 3.333 | — | 5.0 | 0 | 0 | 0.88 | 20 |
| PIPC/CPG-Liq | 0.86 | 2.40 | 0 | 0.040 | 0 | 0.40 | 0 | 4.0 | 8.30 | 0 | 16 |
| PIPC/CPG-LYO | 1.07 | 3.00 | 6.67 | 0.050 | 3.333 | 0.50 | 0 | 5.0 | 0.38 | 0 | 20 |

The order of addition used for blending all excipients was as follows: aluminum hydroxide→trehalose→TWEEN 80→alanine→buffer→rPA→CPG or GLA adjuvant A final volume of 20 mL was prepared for samples 14-20, 40-45 and 76-81 for lyophilization. Blends were split into 10 mL glass vials in 2 mL aliquots and set aside for lyophilization.

Lyophilization Procedure

Samples were lyophilized using a VirTis Plus Freeze Dryer. A 73 hour cycle was employed and entered as described in Table 18.

TABLE 18

| Lyophilization Cycle | | | | | |
|---|---|---|---|---|---|
| # | Step | Temp (° C.) | Time (Hr) | Ramp/Hold | Vacuum (mTorr) |
| 1 | Thermal | −60 | fast | — | — |
| 2 | Treatment | −60 | 2 | H | |
| 3 | | −28 | 1 | R | |
| 4 | | −28 | 20 | H | |
| 5 | Extra Freezing | −28 | 10 | H | 20 |
| 6 | Primary | 25 | 8 | R | 20 |
| 7 | Drying | 25 | 10 | H | |
| 8 | | 30 | 1 | R | |
| 9 | | 30 | 5 | H | |
| 10 | Secondary | 35 | 1 | R | |
| 11 | Drying | 35 | 5 | H | |
| 12 | | 40 | 1 | R | |

TABLE 18-continued

| Lyophilization Cycle | | | | | |
|---|---|---|---|---|---|
| # | Step | Temp (° C.) | Time (Hr) | Ramp/Hold | Vacuum (mTorr) |
| 13 | | 40 | 4 | H | |
| 14 | | 45 | 1 | R | |
| 15 | | 45 | 4 | H | |
| | Post-Drying | 25 | — | — | 3000 |

Summary of Data

The immunological response of the six vaccines formulations was tested in mice (n=10) with one immunization using IP route. The serum was collected 28 days after immunization. TNA data at dose level=0.4 was determined as described in Example 3 and the results are summarized in Table 19.

The mean NF50 was found to be 53.6, 48.9, 69.9, 64.7, 89.4 and 77.3 for CPG-liq, CPG-lyo, GLA-liq, GLA-lyo, PIPC/CPG-liq and PIPC/CPG-lyo samples, respectively. There is no statistical different in the mean NF50 of the liquid versus the lyophilized formulations for CPG, GLA and PIPC/CPG. The data demonstrated the lyophilized formulation and process is capable of maintaining the immunogenicity, even in the presence and of other adjuvants.

TABLE 19

NF50 of liquid versus lyophilization formulations of
CPG, GLA and PIPC/CPG adjuvant containing vaccines

| n | CPG-Liq | CPG-Lyo | GLA-Liq | GLA-Lyo | PIPC/CPG-Liq | PIPC/CPG-Liq |
|---|---|---|---|---|---|---|
| | | | NF50 (DL = 0.4) | | | |
| 1 | 51.2 | 43.1 | 114.4 | 108.9 | 91.6 | 62.8 |
| 2 | 106.3 | 29.2 | 115.2 | 23.7 | 100.8 | 67.2 |
| 3 | 103.9 | 77.4 | 43.1 | 65.1 | 114.5 | 119.2 |
| 4 | 33.1 | 17.2 | 50.3 | 60.9 | 74.6 | 84.0 |
| 5 | 10.3 | 47.8 | 122.0 | 83.3 | 19.4 | 63.2 |
| 6 | 37.3 | 31.4 | 55.9 | 29.2 | 249.5 | 68.6 |
| 7 | 47.6 | 51.8 | 50.1 | 115.8 | 61.0 | 84.8 |
| 8 | 54.7 | 66.4 | 33.3 | 79.3 | 65.3 | 62.4 |
| 9 | 42.8 | 36.5 | 81.7 | 67.9 | 29.8 | 79.4 |
| 10 | 48.9 | 87.9 | 32.5 | 12.9 | 87.4 | 81.2 |
| Mean | 53.6 | 48.9 | 69.9 | 64.7 | 89.4 | 77.3 |
| Stdev | 29.9 | 22.5 | 35.5 | 34.6 | 63.6 | 17.3 |
| P value T-test | 0.695 | | 0.746 | | 0.573 | |
| | | | Log NF50 (DL = 0.4) | | | |
| 1 | 1.7 | 1.6 | 2.1 | 2.0 | 2.0 | 1.8 |
| 2 | 2.0 | 1.5 | 2.1 | 1.4 | 2.0 | 1.8 |
| 3 | 2.0 | 1.9 | 1.6 | 1.8 | 2.1 | 2.1 |
| 4 | 1.5 | 1.2 | 1.7 | 1.8 | 1.9 | 1.9 |
| 5 | 1.0 | 1.7 | 2.1 | 1.9 | 1.3 | 1.8 |
| 6 | 1.6 | 1.5 | 1.7 | 1.5 | 2.4 | 1.8 |
| 7 | 1.7 | 1.7 | 1.7 | 2.1 | 1.8 | 1.9 |
| 8 | 1.7 | 1.8 | 1.5 | 1.9 | 1.8 | 1.8 |
| 9 | 1.6 | 1.6 | 1.9 | 1.8 | 1.5 | 1.9 |
| 10 | 1.7 | 1.9 | 1.5 | 1.1 | 1.9 | 1.9 |
| Mean Log | 1.7 | 1.6 | 1.8 | 1.7 | 1.9 | 1.9 |
| GeoMean | 45.6 | 44.1 | 62.2 | 53.7 | 72.4 | 75.8 |
| Stdev | 0.3 | 0.2 | 0.2 | 0.3 | 0.3 | 0.1 |
| P value T-test | 0.898 | | 0.607 | | 0.849 | |

Example 8: Immunogenicity of Lyophilized rPA Vaccines

This Examples compares liquid vaccine freshly made vs lyophilized vaccine stored at 5 and 50° C. for 1 month and compares CPG formulations made in NaPi (pH 7.0) vs Citric (pH 5.5) buffers.
There are four formulation evaluated under this study:
rPA alum in NaPi (pH 7.0)
rPA alum+CPG in NaPi (pH 7.0)
rPA alum+CPG in Critic (pH 5.5)
rPA alum+GLA in Tris (pH 7.4)
Stock Solution Preparations
Three 60% (w/v) solutions of trehalose were prepared, one in 20 mM Tris (pH 7.4), a second in 5 mM NaPi buffers (pH 7.0), and a third in 20 mM Na-Citrate (pH 5.5). A 10% (v/v) solution of Polysorbate80 was prepared by mixing 10 mL of concentrated TWEEN 80 in 90 mL of DI water. Three 12% (w/v) solutions of alanine were prepared, one in 20 mM Tris (pH 7.4), a second in 5 mM NaPi buffers (pH 7.0), and a third in 20 mM Na-Citrate (pH 5.5) and all were sterile filtered.

Three aluminum hydroxide stock solutions were buffered by adding 1M buffers into the 2% AlOH. The resulting stocks were titrated to the desired pH to match the buffer in use. The dilution effect from the buffer addition and subsequent titration was not accounted for in any of the preparations.

TABLE 19

Formulations Prior to Lyophilization

| # | Buffer | Storage Condition | rPA mg/mL | Aluminum mg/mL | Trehal. % | Alanine % | CPG mg/mL | GLA mg/mL | TWEEN 80 (%) |
|---|---|---|---|---|---|---|---|---|---|
| 1 | 5 mM NaPI | Liquid Fresh | 0.5 | 5.0 | 20.0 | 2.0 | — | — | 0.025 |
| 2 | pH 7.0 | Lyo 5° C., 1 mo | | | | | | | |
| 3 | | Lyo 50° C., 1 mo | | | | | | | |
| 4 | 5 mM NaPI | Liquid Fresh | 0.45 | 4.5 | 20.0 | 2.0 | 1.5 | — | 0.025 |
| 5 | pH 7.0 | Lyo 5° C., 1 mo | | | | | | | |
| 6 | | Lyo 50° C., 1 mo | | | | | | | |
| 7 | Na-Citrate | Liquid Fresh | 0.45 | 4.5 | 20.0 | 2.0 | 1.5 | — | 0.025 |
| 8 | pH 5.5 | Lyo 5° C., 1 mo | | | | | | | |
| 9 | | Lyo 50° C., 1 mo | | | | | | | |
| 10 | 20 mM | Liquid Fresh | 0.45 | 4.5 | 20.0 | 0.0 | — | 0.30 | 0.025 |
| 11 | Tris-HCL | Lyo 5° C., 1 mo | | | | | | | |
| 12 | pH 7.4 | Lyo 50° C., 1 mo | | | | | | | |

Each formulation was blended and then lyophilized at 2 mL per vial, using the lyophilization process as described in Example 7.

TABLE 20

| | | Liquid Fresh or Reconstituted Concentrations | | | | | | |
|---|---|---|---|---|---|---|---|---|
| # | Buffer | Storage Condition | rPA mg/mL | Aluminum mg/mL | Trehal. % | Alanine % | CPG mg/mL | GLA mg/mL | TWEEN 80 (%) |
| 1 | 5 mM NaPI pH 7.0 | Liquid Fresh | 0.15 | 1.5 | 6.06 | 0.61 | 0 | 0 | .008 |
| 2 | | Lyo 5° C., 1 mo | | | | | | | |
| 3 | | Lyo 50° C., 1 mo | | | | | | | |
| 4 | 5 mM NaPI pH 7.0 | Liquid Fresh | 0.15 | 1.5 | 6.67 | 0.67 | .5 | 0 | .008 |
| 5 | | Lyo 5° C., 1 mo | | | | | | | |
| 6 | | Lyo 50° C., 1 mo | | | | | | | |
| 7 | Na-Citrate pH 5.5 | Liquid Fresh | 0.15 | 1.5 | 6.67 | 0.67 | .5 | 0 | .008 |
| 8 | | Lyo 5° C., 1 mo | | | | | | | |
| 9 | | Lyo 50° C., 1 mo | | | | | | | |
| 10 | 20 mM Tris-HCL pH 7.4 | Liquid Fresh | 0.15 | 1.5 | 6.67 | 0 | 0 | 0.1 | .008 |
| 11 | | Lyo 5° C., 1 mo | | | | | | | |
| 12 | | Lyo 50° C., 1 mo | | | | | | | |

Animal Model

Each animal receive 0.5 mL of 1/16 dilution of the listed formulations. 5 Female/5 Male Guinea pig per group (n=10). IM immunization was performed on Day 0 and Day 14. Blood collection was performed on day 14, 28 and 35. The TNA data at day 28 was analyzed and presented.

NF50 Data

Figure 21:
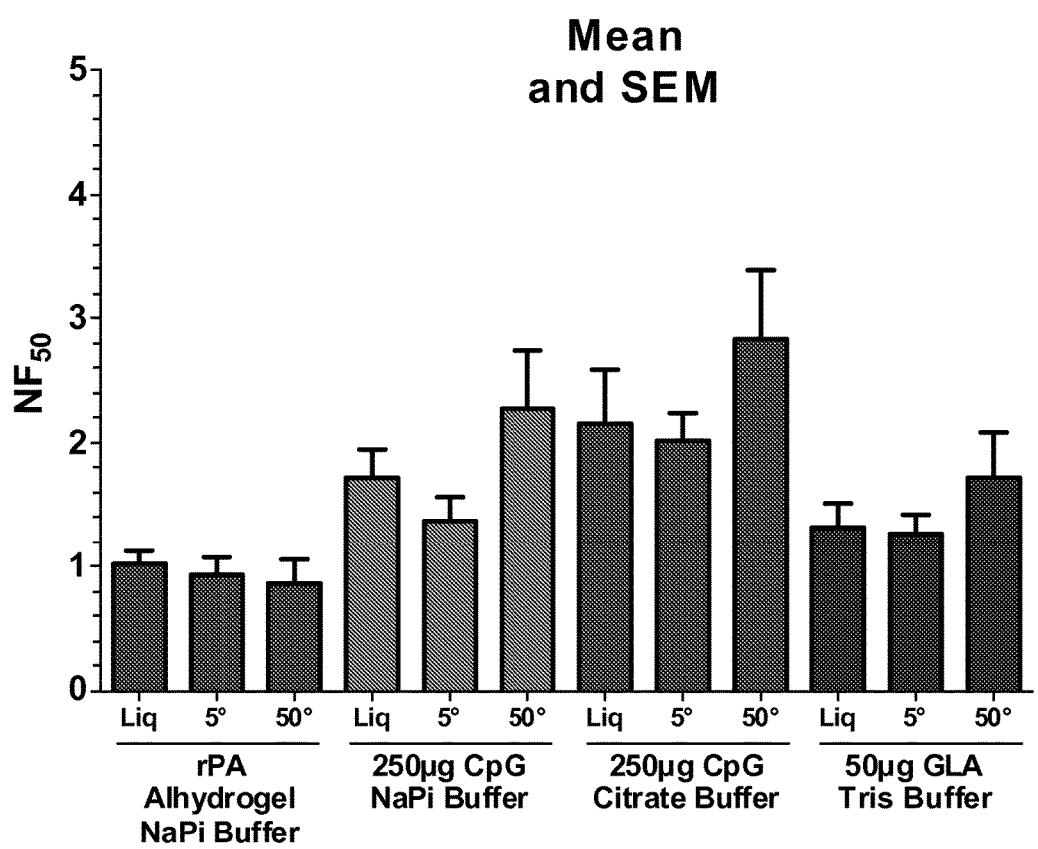
FIG. 21. A graph showing NF50 values and the standard deviation of mean for 12 formulations as described in Example 8.

FIG. 21 shows the NF50 and the standard deviation of mean of the 12 formulations.

Table 21 shows the numerical values of each mouse of the 12 formulations.

TABLE 21

| | NF50 and LogNF50 For Each Mouse For Each of the 12 Formulations. | | | | | |
|---|---|---|---|---|---|---|
| n | rPA Alhydrogel NaPi Liq | rPA Alhydrogel NaPi 5° C. | rPA Alhydrogel NaPi 50° C. | 250 µg CpG NaPi Liq | 250 µg CpG NaPi 5° C. | 250 µg CpG NaPi 50° C. |
| | NF50 (DL = 0.063) | | | | | |
| 1 | 1.4 | 0.9 | 1.0 | 2.9 | 0.9 | 4.8 |
| 2 | 1.1 | 0.7 | 0.4 | 2.5 | 2.1 | 1.9 |
| 3 | 1.0 | 1.8 | 1.5 | 1.2 | 0.8 | 5.1 |
| 4 | 0.6 | 1.0 | 1.0 | 1.8 | 1.9 | 2.6 |
| 5 | 1.1 | 1.3 | 2.0 | 2.4 | 2.6 | 1.8 |
| 6 | 1.3 | 1.4 | 0.2 | 1.7 | 1.0 | 1.5 |
| 7 | 1.3 | 1.0 | 0.8 | 1.9 | 1.4 | 1.4 |
| 8 | 0.7 | 0.4 | 0.2 | 0.9 | 1.4 | 1.1 |
| 9 | 0.4 | 0.5 | 1.0 | 0.8 | 0.6 | 1.9 |
| 10 | 1.3 | 0.5 | 0.5 | 1.2 | 0.8 | 0.6 |
| Mean | 1.0 | 0.9 | 0.9 | 1.7 | 1.4 | 2.3 |
| SD | 0.3 | 0.5 | 0.6 | 0.7 | 0.7 | 1.5 |
| % CV | 33.9 | 49.1 | 66.6 | 40.8 | 48.1 | 65.8 |
| P Value (ANOVA) | | 0.770 | | | 0.152 0.132 | |
| | Log NF50 (DL = 0.063) | | | | | |
| 1 | 0.15 | −0.03 | 0.00 | 0.46 | −0.03 | 0.68 |
| 2 | 0.04 | −0.19 | −0.44 | 0.39 | 0.31 | 0.29 |
| 3 | −0.02 | 0.26 | 0.17 | 0.09 | −0.08 | 0.71 |
| 4 | −0.20 | −0.01 | 0.00 | 0.25 | 0.29 | 0.41 |
| 5 | 0.06 | 0.10 | 0.31 | 0.38 | 0.42 | 0.26 |
| 6 | 0.11 | 0.14 | −0.74 | 0.24 | 0.01 | 0.19 |
| 7 | 0.12 | −0.02 | −0.09 | 0.27 | 0.15 | 0.16 |
| 8 | −0.13 | −0.41 | −0.61 | −0.05 | 0.13 | 0.04 |
| 9 | −0.45 | −0.34 | 0.01 | −0.11 | −0.21 | 0.27 |
| 10 | 0.11 | −0.30 | −0.27 | 0.08 | −0.11 | −0.24 |
| Mean Log | −0.02 | −0.08 | −0.17 | 0.20 | 0.09 | 0.28 |
| Geo Mean | 0.95 | 0.83 | 0.68 | 1.58 | 1.23 | 1.89 |
| SD | 0.19 | 0.22 | 0.34 | 0.19 | 0.21 | 0.28 |
| P Value (ANOVA) | | 0.472 | | | 0.201 0.210 | |

TABLE 21-continued

NF50 and LogNF50 For Each Mouse For Each of the 12 Formulations.

| n | 250 µg CpG Citrate Liq | 250 µg CpG Citrate 5° C. | 250 µg CpG Citrate 50° C. | 50 µg GLA Tris Liq | 50 µg GLA Tris 5° C. | 50 µg GLA Tris 50° C. |
|---|---|---|---|---|---|---|
| | | | NF50 (DL = 0.063) | | | |
| 1 | 1.5 | 1.9 | 2.3 | 1.1 | 2.2 | 2.4 |
| 2 | 4.6 | 2.4 | 3.3 | 2.3 | 0.8 | 2.4 |
| 3 | 3.0 | 2.8 | 4.3 | 2.1 | 1.2 | 1.8 |
| 4 | 4.2 | 2.9 | 4.2 | 1.7 | 2.0 | 4.2 |
| 5 | 0.9 | 1.6 | 2.8 | 1.4 | 0.8 | 2.1 |
| 6 | 1.5 | 1.3 | 1.9 | 1.4 | 1.2 | 0.5 |
| 7 | 0.8 | 2.7 | 6.3 | 0.9 | 0.9 | 1.6 |
| 8 | 1.5 | 0.9 | 1.2 | 1.3 | 1.1 | 0.6 |
| 9 | 1.5 | 2.3 | 1.5 | 0.6 | 1.1 | 1.1 |
| 10 | 2.0 | 1.2 | 0.6 | 0.4 | 1.3 | 0.4 |
| Mean | 2.2 | 2.0 | 2.8 | 1.3 | 1.3 | 1.7 |
| SD | 1.4 | 0.7 | 1.7 | 0.6 | 0.5 | 1.2 |
| % cv | 62.6 | 36.0 | 61.1 | 46.4 | 38.6 | 67.5 |
| P Value (ANOVA) | | 0.356 0.132 | | | 0.412 | |
| | | | Log NF50 (DL = 0.063) | | | |
| 1 | 0.19 | 0.28 | 0.36 | 0.03 | 0.35 | 0.38 |
| 2 | 0.67 | 0.38 | 0.52 | 0.36 | −0.12 | 0.38 |
| 3 | 0.47 | 0.45 | 0.63 | 0.32 | 0.09 | 0.26 |
| 4 | 0.63 | 0.47 | 0.63 | 0.24 | 0.30 | 0.62 |
| 5 | −0.07 | 0.22 | 0.45 | 0.13 | −0.12 | 0.33 |
| 6 | 0.19 | 0.12 | 0.27 | 0.16 | 0.09 | −0.35 |
| 7 | −0.12 | 0.43 | 0.80 | −0.06 | −0.03 | 0.21 |
| 8 | 0.19 | −0.07 | 0.06 | 0.12 | 0.06 | −0.22 |
| 9 | 0.19 | 0.37 | 0.19 | −0.22 | 0.04 | 0.04 |
| 10 | 0.29 | 0.09 | −0.23 | −0.40 | 0.10 | −0.36 |
| Mean Log | 0.26 | 0.27 | 0.37 | 0.07 | 0.08 | 0.13 |
| Geo Mean | 1.83 | 1.88 | 2.33 | 1.17 | 1.19 | 1.34 |
| SD | 0.26 | 0.18 | 0.31 | 0.24 | 0.15 | 0.3 |
| P Value (A NOVA) | | 0.603 0.210 | | | 0.847 | |

The NF50 data shows superior stability of the four lyophilized formulations. It also demonstrated the robustness of the formulations.

No statistical difference of NF50 mean and Geomean among liquid fresh, lyo (5 and 50° C. for 1 month) for all four formulations: (see Table 21)

No statistical difference of mean and geomean of NF50 between NaPi vs Citric buffer for rPA alum+CPG formulation. (see Table 21)

Example 9: Formulations with Influenza Antigen(s)

Formulations containing influenza antigen(s) are formulated using methods similar to the disclosed herein for rPA formulations, except for the presence of influenza antigen(s) and the absence of rPA antigens.

Examples of formulations containing influenza antigens are listed in Table 20.

TABLE 22

Examples of Formulations Containing Influenza Antigen for Lyophilization

| Formulation # | Influenza Antigen mg/ml | Alum mg/ml | Sugar | Amino Acid | TWEEN 80 | Liq. Lyoph. Vol. |
|---|---|---|---|---|---|---|
| 1 | 0.15 | 1.5 | 20% Trehalose | none | 0.025% | 2 mL |
| 2 | 0.15 | 1.5 | 30% Trehalose | none | 0.025% | 2 mL |
| 3 | 0.15 | 1.5 | 20% Trehalose | 2% Ala | 0.025% | 2 mL |
| 4 | 0.15 | 1.5 | 30% Trehalose | 2% Ala | 0.025% | 2 mL |
| 5 | 0.15 | 1.5 | 20% Trehalose | 2% Gly | 0.025% | 2 mL |
| 6 | 0.15 | 1.5 | 30% Trehalose | 2% Gly | 0.025% | 2 mL |
| 7 | 0.15 | 1.5 | 20% Trehalose | 2% Arg | 0.025% | 2 mL |
| 8 | 0.15 | 1.5 | 30% Trehalose | 2% Arg | 0.025% | 2 mL |
| 9 | 0.15 | 1.5 | 10% Trehalose | 2% Ala | 0.025% | 2 mL |
| 10 | 0.15 | 1.5 | 10% Trehalose | 2% Gly | 0.025% | 2 mL |
| 11 | 0.15 | 1.5 | 10% Trehalose | 2% Arg | 0.025% | 2 mL |
| 12 | 0.5 | 5 | 20% Trehalose | none | 0.025% | 2 mL |
| 13 | 0.5 | 5 | 30% Trehalose | none | 0.025% | 2 mL |
| 14 | 0.5 | 5 | 20% Trehalose | 2% Ala | 0.025% | 2 mL |
| 15 | 0.5 | 5 | 30% Trehalose | 2% Ala | 0.025% | 2 mL |
| 16 | 0.5 | 5 | 20% Trehalose | 2% Gly | 0.025% | 2 mL |

TABLE 22-continued

Examples of Formulations Containing Influenza Antigen for Lyophilization

| Formulation # | Influenza Antigen mg/ml | Alum mg/ml | Sugar | Amino Acid | TWEEN 80 | Liq. Lyoph. Vol. |
|---|---|---|---|---|---|---|
| 17 | 0.5 | 5 | 30% Trehalose | 2% Gly | 0.025% | 2 mL |
| 18 | 0.5 | 5 | 20% Trehalose | 2% Arg | 0.025% | 2 mL |
| 19 | 0.5 | 5 | 30% Trehalose | 2% Arg | 0.025% | 2 mL |
| 20 | 0.5 | 5 | 10% Trehalose | 2% Ala | 0.025% | 2 mL |
| 21 | 0.5 | 5 | 10% Trehalose | 2% Gly | 0.025% | 2 mL |
| 22 | 0.5 | 5 | 10% Trehalose | 2% Arg | 0.025% | 2 mL |

Two sets of formulations are made, one in 5 mM NaPi, pH 7.0 buffer or 20 mM Tris, pH 7.4 buffer. The influenza antigen is an influenza hemagglutinin. Formulations may also contain another adjuvant such as CPG at 0.5 mg/mL, PIPC at 0.5 mg/mL, GLA at 0.1 mg/Ml or a combination thereof.

Each formulation is lyophilized, 2 mL per vial, using the lyophilization process as described in Example 7.

Each formulation is tested in immunogenicity studies, stability studies and/or efficacy studies.

Example 10: Lyophilized Anthrax Vaccine Containing CPG 7909 Adjuvant

Material
1. BIOTHRAX® vaccine, stored at 5° C. and in a 4 L glass bottle
2. CPG 7909, Lyophilized powder
3. α,α-Trehalose dehydrate (Ferro Pfanstiehl)

Equipment
1. Sorvall LYNX 6000 Superspeed Centrifuge with Rotor-Fiberlite F9-6×1000 LEX (cat. No. 096-061075)
2. 1 L centrifugation bottle—(Nalgene, Cat. No. 3141-1006)
3. Ultra EL-85 Freeze dryer, Model 50L Ultra EL-85
4. Magnetic Stir Plate
5. Sterile Nalgene square media bottles (VWR product #16059-498 (1 L), 16059-496 (0.5 L))

Figure 23A:
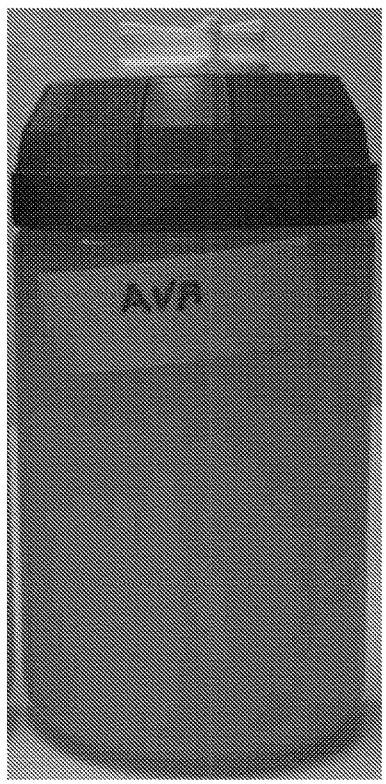
FIG. 23A-B shows a photograph of BIOTHRAX® vaccine before (FIG. 23A) and after centrifugation (FIG. 23B).
Figure 23B:
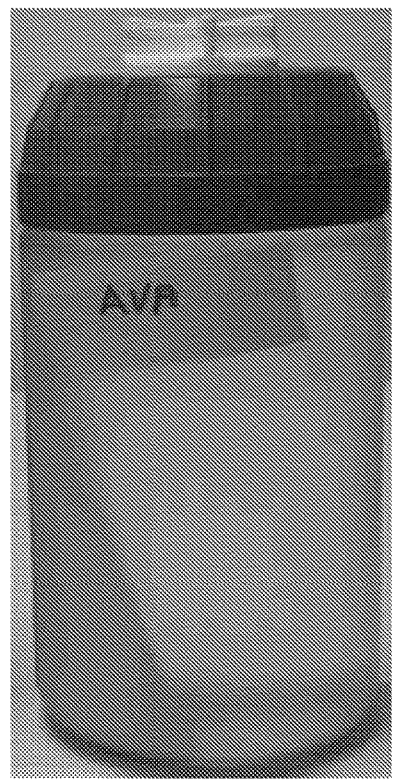
Figure 24A:
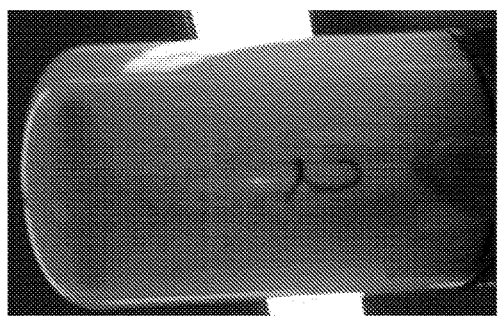
FIG. 24A-B shows photographs showing an anthrax based vaccine that contains trehalose and CPG 7909 before (FIG. 24A) and after a mixing process (FIG. 24B).
Figure 24B:
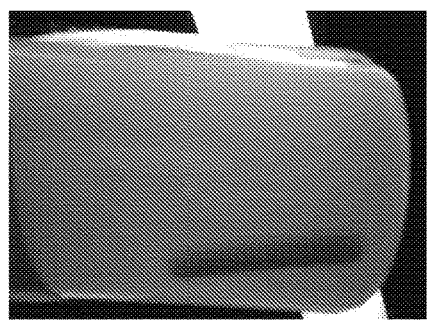

Procedure
1) FIG. 22 shows the overall flow diagram of the formulation processes used in this Example. The following provides a more detailed description of the formulation processes.
2) 1 kg of the BIOTHRAX® vaccine was transferred into the 1 L Nalgene bottle and placed inside the Sorvall LYNX 6000 Superspeed Centrifuge with Rotor-Fiberlite F9-6×1000 LEX. The centrifuge was set at 3000 rpm (or ~3000 g-force) for 5 minutes. FIG. 23 shows a photograph of the BIOTHRAX® vaccine before (FIG. 23A) and after centrifugation (FIG. 23B). After centrifugation a clear supernatant is seen next to the pellet and the pellet accumulates on the side of the bottle (FIG. 23B).
3) After centrifugation, the supernatant (900 grams) was removed by decanting on the side of the bottle opposite of the pellet to avoid disrupting the pellet.
4) The decanted portion was further divided by removing 234 g (~234 mL). The remaining ~666 mL was discarded.
5) To the 234 mL portion, 98.5 g of solid trehalose was added. A stir bar was added to the bottle and it was mixed on a magnetic stir plate at medium speed for 20 minutes. The trehalose completely dissolved within this time at room temperature. The stir bar was removed and the final volume was measured to be 292.5 mL.
6) 5 mL of CPG 7909 solution at 100 mg/mL was added to the trehalose-containing supernatant. The resulting solution was sterile filtered through a 0.2 μm membrane using a 500 mL Nalgene tissue culture filter unit.
7) The sterilized supernatant was then added to the pellet. After hand-shaking the pellet loose, a stir bar was added and the mixture was stirred at medium speed for 3 hours and the pellet was found to be dispersed visually. FIG. 24 shows photographs showing the mixture, before (FIG. 24A) and after the mixing process (FIG. 24B).
8) 2.36 mL of the dispersed suspension was added to each 10 mL glass vial. The filled vials were loaded in a lyophilizer: pilot Ultra EL-85 freeze-dryer with the lyophilization parameters shown in Table 16.
9) Lyophilization produced a lyophilized anthrax vaccine (derived from BIOTHRAX® vaccine) with CPG 7909 adjuvant.
10) Water for injection containing 17 ppm phemerol was used to reconstitute the lyophilized vaccine to produce a final volume of 6 mL suspension, equivalent to 12 doses of the vaccine per vial. Each dose consists of 0.5 mL which includes a dose of anthrax vaccine with 0.25 mg of CPG 7909. Phemerol is used as a preservative in this example.

TABLE 16

Lyophilization Parameters

| Steps | | Shelf setpoint (° C.) | Ramp rate (° C./min) | Hold time (hours) | Final freezing setpoint (° C.) | Extra freezing time (min) | Starting vacuum setpoint (mTorr) |
|---|---|---|---|---|---|---|---|
| Freezing | | −60 | 1 | 72 | −28 | 180 | 100 |
| Drying | 1 | −28 | 0 | 6 | N/A | | 100 |
| Steps | 2 | −28 | 0 | 6 | | | 40 |
| | 3 | −21 | 0 | 4 | | | 40 |
| | 4 | −21 | 0 | 12 | | | 20 |
| | 5 | −18 | 0 | 10 | | | 20 |
| | 6 | 25 | 0.2 | 10 | | | 20 |
| | 7 | 30 | 0.2 | 5 | | | 20 |
| | 8 | 35 | 0.2 | 3 | | | 20 |
| | 9 | 40 | 0.2 | 3 | | | 20 |
| | 10 | 45 | 0.2 | 2 | | | 20 |

Testing

The quality of the lyophilized vaccine was evaluated by measuring and comparing the particle size of the reconstituted vaccine to that of the BIOTHRAX® vaccine starting material (positive control) and the BIOTHRAX® vaccine frozen without trehalose (negative control).

Immunogenicity of anthrax vaccine containing an aluminum adjuvant, such as aluminum hydroxide, typically correlates to the particle size of the vaccine and as the median particle size, Dv50, increase beyond 10 um, significant loss of immunogenicity is observed (data not shown).

The particle size of reconstituted vaccine was measured by using Malvern MasterSizer 3000. The Dv50s were found to be 3.3, 4.2 and 13.7 um for BIOTHRAX® vaccine (positive control; same as starting material); the lyophilized anthrax vaccine containing CPG 7909 adjuvant and trehalose; and BIOTHRAX® vaccine frozen without trehalose (negative control). The data suggests that there is no significant change in particle size of the lyophilized vaccine containing CPG 7909 adjuvant and trehalose.

The lyophilized anthrax vaccine derived from BIOTHRAX® vaccine as described in this Example can be tested in the in vivo mouse potency assay described in Example 3; the rabbit immunogenicity and stability study described in Example 4; the guinea pig immunogenicity study described in Example 5 and 8; the mouse immunogenicity and physiochemical stability study in Example 6; an anthrax challenge model, such as an anthrax prophylaxis study in guinea pigs (e.g., as described in Example 11); or a combination thereof The methods described in this Example may also be carried out, but without the addition of CPG 7909 to create a lyophilized anthrax vaccine.

Example 11: General Use Anthrax Prophylaxis (GUP) Study in Guinea Pigs

Anthrax vaccines of the invention may be tested in an anthrax prophylaxis study in guinea pigs. An example of one such study is described here.

A study design is outlined in Table 17. Briefly, five groups of animals, Groups 1-5, (e.g., 24 mice per group), equal number males and females, are immunized intramuscularly (IM) on study days 0 and 28 with 0.5 mL of various dilutions of an anthrax vaccine as described in Table 17. Animals are challenged with a target dose of 200 LD50's of aerosolized anthrax spores on study day 70 and observed for morbidity and mortality for 21 days after challenge. Twelve (12) control animals (Group 6) will be administered with 0.5 mL of normal saline or vehicle under the same schedule.

While different sample sizes could be used, 24 animals per group should provide sufficient statistical power to detect a one standard unit change in the geometric mean TNA NF50 between two groups and to conclude whether the survival probability of Group is different from another group.

Study endpoints can include the following:
Death due to anthrax
TNA levels (ED50 and NF50)
Anti-PA IgG concentration (measured by ELISA)
Bacteremia
Time to death due to anthrax
Clinical observations
Necropsy and histopathology (as needed to confirm death due to anthrax)

TABLE 17

Study Design

| Group | No. of Animals | Vaccine | Vaccine Dilution | Immunization Schedule (Study Days) | Anthrax Challenge (Study Day) | Blood Collection Schedule (Days) |
|---|---|---|---|---|---|---|
| 1 | 24 | Test Vaccine | 1/32 | 0, 28 | 70 | −3, 28, 42, 69, 91 |
| 2 | 24 | Test Vaccine | 1/64 | | | |
| 3 | 24 | Test Vaccine | 1/96 | | | |
| 4 | 24 | Test Vaccine | 1/128 | | | |
| 5 | 24 | Test Vaccine | 1/256 | | | |
| 6 | 12 | Normal Saline | N/A | | | |
| Total | 252 | | | | | |

What is claimed is:

1. A method of preparing a stable lyophilized vaccine, the method comprising:
   (a) exchanging at least part of a liquid component of a first composition comprising at least one Anthrax antigen adsorbed to an aluminum adjuvant with a second liquid component comprising (i) a non-reducing sugar to create a second composition that comprises at least 20% (w/v) non-reducing sugar and 75 to 750 µg/ml Anthrax antigen, (ii) a non-reducing sugar and an amino acid to create a second composition that comprises at least 10% (w/v) non-reducing sugar and 75 to 750 µg/ml Anthrax antigen, or (iii) a non-reducing sugar and a surfactant to create a second composition that comprises at least 15% (w/v) non-reducing sugar and 75 to 750 µg/ml Anthrax antigen;

wherein the exchanging comprises (x) separating the liquid component of the first composition from a solid component of the first composition; (y) centrifuging the first composition and separating at least part of the liquid component of the first composition from a pelleted component of the first composition; or (z) filtering the first composition to separate at least part of the liquid component of the first composition from a solid component of the first composition;

wherein the second liquid component is prepared by adding the non-reducing sugar, the amino acid, and/or the surfactant of (i), (ii) or (iii) to at least a portion of the liquid component separated from the first composition according to (x), (y), or (z); and wherein the creation of the second composition comprises combining (1) the second liquid component and (2) the solid component or the pelleted component of the first composition; and (b) lyophilizing the second composition.

2. The method of claim 1, wherein the second liquid component comprising (i) or (ii) further comprises a surfactant.

3. The method of claim 1, wherein the exchanging comprises centrifuging the first composition and separating at least part of the liquid component of the first composition from the pelleted component of the first composition.

4. The method of claim 1, wherein the aluminum adjuvant is aluminum hydroxide, aluminum phosphate or aluminum sulfate.

5. The method of claim 4, wherein the first or second composition contains about 0.5 to about 1.5 mg/ml aluminum hydroxide.

6. The method of claim 1, wherein the surfactant is selected from the group consisting of polysorbate 80 and polysorbate 20.

7. The method of claim 1, wherein the non-reducing sugar is trehalose, sucrose, or a combination thereof.

8. The method of claim 1, wherein the second composition contains about 15-40% (w/v) non-reducing sugar.

9. The method of claim 1, wherein the Anthrax antigen is a protective antigen having at least about 80% identity to the polypeptide of SEQ ID NO: 2.

10. The method of claim 1, wherein the Anthrax antigen is a cell-free filtrate from an avirulent *B. anthracis* strain.

11. The method of claim 10, wherein the avirulent *B. anthracis* strain is V770-NP1-R.

12. The method of claim 1, wherein the first composition or second composition is an anthrax vaccine.

13. The method of claim 1 wherein the second composition comprises at least one amino acid.

14. The method of claim 13 wherein the at least one amino acid is selected from the group consisting of arginine, alanine, proline and glycine.

15. The method of claim 14, wherein the second composition contains alanine or arginine, at about 0.5-4% (w/v) or about 2% (w/v).

* * * * *

SEQUENCE LISTING

<160> NUMBER OF SEQ ID NOS: 3

<210> SEQ ID NO 1
<211> LENGTH: 735
<212> TYPE: PRT
<213> ORGANISM: Artificial Sequence
<220> FEATURE:
<223> OTHER INFORMATION: Synthetic polypeptide

<400> SEQUENCE: 1

```
Glu Val Lys Gln Glu Asn Arg Leu Leu Asn Glu Ser Glu Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
```

```
              355                 360                 365
Thr Gly Thr Ala Pro Ile Tyr Asn Val Leu Pro Thr Thr Ser Leu Val
              370                 375                 380
Leu Gly Lys Asn Gln Thr Leu Ala Thr Ile Lys Ala Lys Glu Asn Gln
385                 390                 395                 400
Leu Ser Gln Ile Leu Ala Pro Asn Asn Tyr Pro Ser Lys Asn Leu
              405                 410                 415
Ala Pro Ile Ala Leu Asn Ala Gln Asp Asp Phe Ser Thr Pro Ile
              420                 425                 430
Thr Met Asn Tyr Asn Gln Phe Leu Glu Leu Glu Lys Thr Lys Gln Leu
              435                 440                 445
Arg Leu Asp Thr Asp Gln Val Tyr Gly Asn Ile Ala Thr Tyr Asn Phe
              450                 455                 460
Glu Asn Gly Arg Val Arg Val Asp Thr Gly Ser Asn Trp Ser Glu Val
465                 470                 475                 480
Leu Pro Gln Ile Gln Glu Thr Thr Ala Arg Ile Ile Phe Asn Gly Lys
              485                 490                 495
Asp Leu Asn Leu Val Glu Arg Arg Ile Ala Ala Val Asn Pro Ser Asp
              500                 505                 510
Pro Leu Glu Thr Thr Lys Pro Asp Met Thr Leu Lys Glu Ala Leu Lys
              515                 520                 525
Ile Ala Phe Gly Phe Asn Glu Pro Asn Gly Asn Leu Gln Tyr Gln Gly
              530                 535                 540
Lys Asp Ile Thr Glu Phe Asp Phe Asn Phe Asp Gln Gln Thr Ser Gln
545                 550                 555                 560
Asn Ile Lys Asn Gln Leu Ala Glu Leu Asn Ala Thr Asn Ile Tyr Thr
              565                 570                 575
Val Leu Asp Lys Ile Lys Leu Asn Ala Lys Met Asn Ile Leu Ile Arg
              580                 585                 590
Asp Lys Arg Phe His Tyr Asp Arg Asn Asn Ile Ala Val Gly Ala Asp
              595                 600                 605
Glu Ser Val Val Lys Glu Ala His Arg Glu Val Ile Asn Ser Ser Thr
              610                 615                 620
Glu Gly Leu Leu Leu Asn Ile Asp Lys Asp Ile Arg Lys Ile Leu Ser
625                 630                 635                 640
Gly Tyr Ile Val Glu Ile Glu Asp Thr Glu Gly Leu Lys Glu Val Ile
              645                 650                 655
Asn Asp Arg Tyr Asp Met Leu Asn Ile Ser Ser Leu Arg Gln Asp Gly
              660                 665                 670
Lys Thr Phe Ile Asp Phe Lys Lys Tyr Asn Asp Lys Leu Pro Leu Tyr
              675                 680                 685
Ile Ser Asn Pro Asn Tyr Lys Val Asn Val Tyr Ala Val Thr Lys Glu
              690                 695                 700
Asn Thr Ile Ile Asn Pro Ser Glu Asn Gly Asp Thr Ser Thr Asn Gly
705                 710                 715                 720
Ile Lys Lys Ile Leu Ile Phe Ser Lys Lys Gly Tyr Glu Ile Gly
              725                 730                 735

<210> SEQ ID NO 2
<211> LENGTH: 706
<212> TYPE: PRT
<213> ORGANISM: Artificial Sequence
<220> FEATURE:
<223> OTHER INFORMATION: Synthetic polypeptide
```

<400> SEQUENCE: 2

```
Gln Ala Pro Met Val Val Thr Ser Ser Thr Gly Asp Leu Ser Ile
1               5                   10                  15

Pro Ser Ser Glu Leu Glu Asn Ile Pro Ser Glu Asn Gln Tyr Phe Gln
            20                  25                  30

Ser Ala Ile Trp Ser Gly Phe Ile Lys Val Lys Lys Ser Asp Glu Tyr
        35                  40                  45

Thr Phe Ala Thr Ser Ala Asp Asn His Val Thr Met Trp Val Asp Asp
    50                  55                  60

Gln Glu Val Ile Asn Lys Ala Ser Asn Ser Asn Lys Ile Arg Leu Glu
65                  70                  75                  80

Lys Gly Arg Leu Tyr Gln Ile Lys Ile Gln Tyr Gln Arg Glu Asn Pro
                85                  90                  95

Thr Glu Lys Gly Leu Asp Phe Lys Leu Tyr Trp Thr Ser Gln Asn
            100                 105                 110

Lys Lys Glu Val Ile Ser Ser Asp Asn Leu Gln Leu Pro Glu Leu Lys
        115                 120                 125

Gln Lys Ser Ser Asn Ser Arg Lys Lys Arg Ser Thr Ser Ala Gly Pro
    130                 135                 140

Thr Val Pro Asp Arg Asp Asn Asp Gly Ile Pro Asp Ser Leu Glu Val
145                 150                 155                 160

Glu Gly Tyr Thr Val Asp Val Lys Asn Lys Arg Thr Phe Leu Ser Pro
                165                 170                 175

Trp Ile Ser Asn Ile His Glu Lys Lys Gly Leu Thr Lys Tyr Lys Ser
            180                 185                 190

Ser Pro Glu Lys Trp Ser Thr Ala Ser Asp Pro Tyr Ser Asp Phe Glu
        195                 200                 205

Lys Val Thr Gly Arg Ile Asp Lys Asn Val Ser Pro Glu Ala Arg His
    210                 215                 220

Pro Leu Val Ala Ala Tyr Pro Ile Val His Val Asp Met Glu Asn Ile
225                 230                 235                 240

Ile Leu Ser Lys Asn Glu Asp Gln Ser Thr Gln Asn Thr Asp Ser Gln
                245                 250                 255

Thr Arg Thr Ile Ser Lys Asn Thr Ser Thr Ser Arg Thr His Thr Ser
            260                 265                 270

Glu Val His Gly Asn Ala Glu Val His Ala Ser Phe Phe Asp Ile Gly
        275                 280                 285

Gly Ser Val Ser Ala Gly Phe Ser Asn Ser Asn Ser Ser Thr Val Ala
    290                 295                 300

Ile Asp His Ser Leu Ser Leu Ala Gly Glu Arg Thr Trp Ala Glu Thr
305                 310                 315                 320

Met Gly Leu Asn Thr Ala Asp Thr Ala Arg Leu Asn Ala Asn Ile Arg
                325                 330                 335

Tyr Val Asn Thr Gly Thr Ala Pro Ile Tyr Asn Val Leu Pro Thr Thr
            340                 345                 350

Ser Leu Val Leu Gly Lys Asn Gln Thr Leu Ala Thr Ile Lys Ala Lys
        355                 360                 365

Glu Asn Gln Leu Ser Gln Ile Leu Ala Pro Asn Asn Tyr Tyr Pro Ser
    370                 375                 380

Lys Asn Leu Ala Pro Ile Ala Leu Asn Ala Gln Asp Asp Phe Ser Ser
385                 390                 395                 400

Thr Pro Ile Thr Met Asn Tyr Asn Gln Phe Leu Glu Leu Glu Lys Thr
                405                 410                 415
```

-continued

```
Lys Gln Leu Arg Leu Asp Thr Asp Gln Val Tyr Gly Asn Ile Ala Thr
                420                 425                 430

Tyr Asn Phe Glu Asn Gly Arg Val Arg Val Asp Thr Gly Ser Asn Trp
        435                 440                 445

Ser Glu Val Leu Pro Gln Ile Gln Glu Thr Thr Ala Arg Ile Ile Phe
    450                 455                 460

Asn Gly Lys Asp Leu Asn Leu Val Glu Arg Arg Ile Ala Ala Val Asn
465                 470                 475                 480

Pro Ser Asp Pro Leu Glu Thr Thr Lys Pro Asp Met Thr Leu Lys Glu
                485                 490                 495

Ala Leu Lys Ile Ala Phe Gly Phe Asn Glu Pro Asn Gly Asn Leu Gln
                500                 505                 510

Tyr Gln Gly Lys Asp Ile Thr Glu Phe Asp Phe Asn Phe Asp Gln Gln
                515                 520                 525

Thr Ser Gln Asn Ile Lys Asn Gln Leu Ala Glu Leu Asn Ala Thr Asn
    530                 535                 540

Ile Tyr Thr Val Leu Asp Lys Ile Lys Leu Asn Ala Lys Met Asn Ile
545                 550                 555                 560

Leu Ile Arg Asp Lys Arg Phe His Tyr Asp Arg Asn Asn Ile Ala Val
                565                 570                 575

Gly Ala Asp Glu Ser Val Val Lys Glu Ala His Arg Glu Val Ile Asn
                580                 585                 590

Ser Ser Thr Glu Gly Leu Leu Leu Asn Ile Asp Lys Asp Ile Arg Lys
            595                 600                 605

Ile Leu Ser Gly Tyr Ile Val Glu Ile Glu Asp Thr Glu Gly Leu Lys
                610                 615                 620

Glu Val Ile Asn Asp Arg Tyr Asp Met Leu Asn Ile Ser Ser Leu Arg
625                 630                 635                 640

Gln Asp Gly Lys Thr Phe Ile Asp Phe Lys Lys Tyr Asn Asp Lys Leu
                645                 650                 655

Pro Leu Tyr Ile Ser Asn Pro Asn Tyr Lys Val Asn Val Tyr Ala Val
                660                 665                 670

Thr Lys Glu Asn Thr Ile Ile Asn Pro Ser Glu Asn Gly Asp Thr Ser
                675                 680                 685

Thr Asn Gly Ile Lys Lys Ile Leu Ile Phe Ser Lys Lys Gly Tyr Glu
        690                 695                 700

Ile Gly
705

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Arg Lys Lys Arg
1
```